(12) United States Patent
Mogi et al.

(10) Patent No.: US 8,193,349 B2
(45) Date of Patent: Jun. 5, 2012

(54) 4-BENZYLAMINO-1-CARBOXYLACYL-PIPERIDINE DERIVATIVES AS CETP INHIBITORS

(75) Inventors: Muneto Mogi, Waltham, MA (US); Ken Yamada, Boston, MA (US); Kayo Yasoshima, Cambridge, MA (US); Toshio Kawanami, Boston, MA (US); Ichiro Umemura, Tsukuba (JP); Yuki Iwaki, Cambridge, MA (US); Hongbo Qin, Nagano (JP); Hidetomo Imase, Cambridge, MA (US)

(73) Assignee: Novartis AG, Basel (CH)

( * ) Notice: Subject to any disclaimer, the term of this patent is extended or adjusted under 35 U.S.C. 154(b) by 625 days.

(21) Appl. No.: 12/265,369

(22) Filed: Nov. 5, 2008

(65) Prior Publication Data

US 2009/0118287 A1 May 7, 2009

Related U.S. Application Data

(60) Provisional application No. 60/985,456, filed on Nov. 5, 2007.

(51) Int. Cl.
  C07D 401/14 (2006.01)
  C07D 413/14 (2006.01)
(52) U.S. Cl. ................................ 544/122; 544/331
(58) Field of Classification Search .................. None
  See application file for complete search history.

(56) References Cited

U.S. PATENT DOCUMENTS

| 2003/0096818 A1 | 5/2003 | Sikorski et al. |
| 2006/0135551 A1 | 6/2006 | Baruah et al. |
| 2006/0148830 A1 | 7/2006 | Terakado et al. |
| 2006/0270675 A1 | 11/2006 | Groneberg et al. |
| 2006/0270705 A1 | 11/2006 | Yonemori et al. |
| 2007/0010529 A1 | 1/2007 | Takahashi et al. |
| 2007/0032485 A1 | 2/2007 | Kubota et al. |
| 2007/0173526 A1 | 7/2007 | Bell et al. |
| 2009/0286790 A1 | 11/2009 | Imase et al. |
| 2009/0292125 A1 | 11/2009 | Okamoto et al. |

FOREIGN PATENT DOCUMENTS

| EP | 0987251 A | 3/2000 |
| JP | 2009/051827 A | 3/2009 |
| JP | 2009/051828 A | 3/2009 |
| WO | WO 00/17165 A1 | 3/2000 |
| WO | WO 00/42011 A1 | 7/2000 |
| WO | WO 01/98344 A2 | 12/2001 |
| WO | WO 02/20016 A1 | 3/2002 |
| WO | WO 03/011837 A1 | 2/2003 |
| WO | WO 2004/031118 A1 | 4/2004 |
| WO | WO 2004/101529 A1 | 11/2004 |
| WO | 2005/033082 A | 4/2005 |
| WO | WO 2005/044797 A1 | 5/2005 |
| WO | 2005/095409 A | 10/2005 |
| WO | WO 2005/097806 A1 | 10/2005 |
| WO | 2006/033002 A | 3/2006 |
| WO | 2006/134378 A | 12/2006 |
| WO | WO 2007/088999 A1 | 8/2007 |
| WO | 2007/107843 A1 | 9/2007 |
| WO | 2008/009435 A | 1/2008 |
| WO | WO 2009/071509 A1 | 6/2009 |
| WO | WO 2009/071701 A1 | 6/2009 |

OTHER PUBLICATIONS

Kallashi et al., 2-Arylbenzoxazoles as CETP inhibitors: Raising HDL-C in cynoCETP transgenic mice, 21 Bioorg. & Med. Chem. Letts. 558-561 (2011).*
Co-pending unpublished U.S. Appl. No. 12/745,105, filed May 27, 2010.
Weis R et al: "Synthesis of 2-substituted bamipine derivatives" Tetrahedron, Elsevier Science Publishers, Amsterdam, NL, vol. 59, No. 9, Feb. 24, 2003, pp. 1395-1402, XP004409938, ISSN: 0040-4020, p. 1395, "introduction"; p. 1397, compound 20a, b.
Vartanyan R S et al: "4-Anilides of 1-Substituted 2,5-Dimethylpiperidines: Synthesis and Analgesic Activity" Khimiko-Farmatsevticheskii Zhurnal, Moscow, RU, vol. 23, No. 5, 1989, pp. 562-565, XP002937455, ISSN: 0023-1134, p. 562, first paragraph; p. 562, compounds X I , V6.
N. S. Prostakov et al: "Benzylation of gamma-(N-aryl amino)piperidines by the Wallach Method" Khimiya Geterotsiklicheskikh Soedinenii, vol. 8, 1988, pp. 1078-1083, XP009078378, compounds VI to XII.
V. V . Kuznetsov et al: "I-Methyl(benzyl)-2,5-dimethyl-4-N-[aryl(alkyl)amino] piperidines and their N-acyl derivatives" Khimiya Geterotsiklicheskikh Soedinenii, vol. 7, 1987, pp. 949-953, XP009078377, compound XX.
E. E. Stashenko et al: "Mass-spectrometric study of ring-substituted secondary and tertiary gamma-aminopiperidines" Khimiya Geterotsiklicheskikh Soedinenii, vol. 3, 1990, pp. 380-387, XP009078379, compounds XII, XIV, XV, XVIII.

* cited by examiner

*Primary Examiner* — Janet Andres
*Assistant Examiner* — Timothy R Rozof
(74) *Attorney, Agent, or Firm* — Sophie Binet Cross

(57) ABSTRACT

The present invention provides a compound of formula (I):

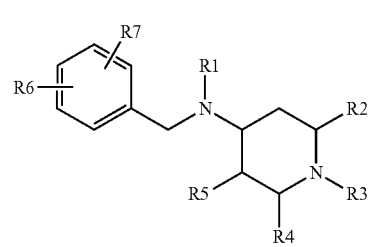

(I)

wherein the variants R1, R2, R3, R4, R5, R6, R7 are as defined herein, and wherein said compound is an inhibitor of CETP, and thus can be employed for the treatment of a disorder or disease mediated by CETP or responsive to the inhibition of CETP.

6 Claims, No Drawings

4-BENZYLAMINO-1-CARBOXYLACYL-PIPERIDINE DERIVATIVES AS CETP INHIBITORS

This application claims benefit under 35 U.S.C. §119(e) of U.S. Provisional Application No. 60/986,456, filed Nov. 5, 2007, the contents of which is incorporated herein by reference in its entirety.

The present invention related to novel compound of formula (I):

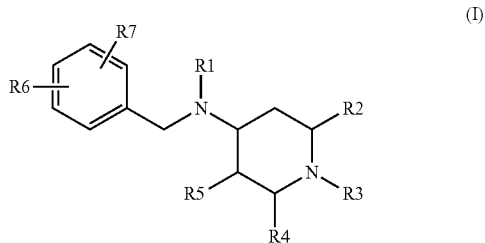

(I)

wherein,

R1 is cycloalkyl, heterocyclyl, aryl, alkyl-O—C(O)—, alkanoyl, or alkyl, wherein each cycloalkyl, heterocyclyl, or aryl is optionally substituted with one to three substituents selected from alkyl, aryl, haloalkyl, hydroxy, halogen, nitro, carboxy, thiol, cyano, HSO3-, cycloalkyl, alkenyl, alkoxy, cycloalkoxy, alkenyloxy, alkyl-O—C(O)—, alkanoyl, carbamoyl, alkyl-S—, alkyl-SO—, alkyl-SO2-, amino, mono- or di-substituted (alkyl, cycloalkyl, aryl and/or aryl-alkyl-) amino, H2N—SO2-, or heterocyclyl, and wherein each alkanoyl, alkyl-O—C(O)—, alkyl, alkoxy, or heterocyclyl is further optionally substituted with one to three substituents selected from hydroxy, alkyl, halogen, nitro, carboxy, thiol, cyano, HSO3-, cycloalkyl, alkenyl, alkoxy, cycloalkoxy, alkenyloxy, alkyl-O—C(O)—, alkanoyl, carbamoyl, alkyl-S—, alkyl-SO—, alkyl-SO2-, amino, mono- or di-substituted (alkyl, cycloalkyl, aryl and/or aryl-alkyl-)amino, H2N—SO2-, or heterocyclyl;

R2 is alkyl, cycloalkyl, cycloalkyl-alkyl-, or alkoxy, wherein each alkyl, cycloalkyl or alkoxy is optionally substituted with one to three substituents selected from alkyl, alkoxy or halogen;

R3 is HOC(O)—R9-C(O)— or HOC(O)—R9-O—C(O)—,

R9 is -alkyl-, -alkyl-cycloalkyl-, -heterocyclyl-, -alkyl-heterocyclyl-, -heterocyclyl-alkyl-, -alkyl-aryl-, -cycloalkyl-, -cycloalkyl-alkyl-, -aryl-, -aryl-alkyl- or -cycloalkyl-alkyl-; or, wherein each R9 is optionally substituted with one to three substituents selected from alkyl, hydroxy, halogen, nitro, carboxy, thiol, cyano, HSO3-, cycloalkyl, alkenyl, alkoxy, cycloalkoxy, alkenyloxy, alkyl-haloalkyl, carboxy, carboxyamide, acyl, alkanoyl, carbamimidoyl, alkyl-S—, alkyl-SO—, alkyl-SO2-, amino, H2N—SO2-, heterocyclyl;

R4 and R5 are independently hydrogen, alkyl, alkoxy, cycloalkyl, aryl, heteroaryl, aryl-alkyl-, cycloalkyl-alkyl-, oxo or heteroaryl-alkyl-, wherein each alkyl, cycloalkyl, aryl, heteroaryl, aryl-alkyl-, cycloalkyl-alkyl-, or heteroaryl-alkyl- is optionally substituted with one to three substituents selected from alkyl, hydroxy, halogen, haloalkyl, nitro, carboxy, thiol, cyano, HSO3-, cycloalkyl, alkenyl, alkoxy, cycloalkoxy, haloalkoxy, alkenyloxy, alkyl-O—C(O)—, alkanoyl, carbamimidoyl, alkyl-S—, alkyl-SO—, alkyl-SO2-, amino, mono- or di-substituted (alkyl, cycloalkyl, aryl and/or aryl-alkyl-) amino, H2N—SO2-, or heterocyclyl; with the proviso that R4 and R5 cannot be hydrogen simultaneously;

R6 and R7 are independently hydrogen, alkyl, haloalkyl, halogen, cyano, nitro, hydroxy, amino, dialkylamino, alkoxy, haloalkoxy; or or a pharmaceutically acceptable salt thereof; or an optical isomer thereof; or a mixture of optical isomers.

The present invention also relates to a process for the preparation of these compounds, to the use of these compounds and to pharmaceutical preparations containing such a compound I in free form or in the form of a pharmaceutically acceptable salt.

Extensive pharmacological investigations have shown that the compounds I and their pharmaceutically acceptable salts, for example, have pronounced selectivity in inhibiting CETP (cholesteryl ester transfer protein). CETP is involved in the metabolism of any lipoprotein in living organisms, and has a major role in the reverse cholesterol transfer system. Namely, CETP has drawn attention as a mechanism for preventing accumulation of cholesterol in peripheral cells and preventing arteriosclerosis. In fact, with regard to HDL having an important role in this reverse cholesterol transfer system, a number of epidemiological researches have shown that a decrease in CE (cholesteryl ester) of HDL in blood is one of the risk factors of coronary artery diseases. It has been also clarified that the CETP activity varies depending on the animal species, wherein arteriosclerosis due to cholesterol-loading is hardly induced in animals with lower activity, and in reverse, easily induced in animals with higher activity, and that hyper-HDL-emia and hypo-LDL (low density lipoprotein)-emia are induced in the case of CETP deficiency, thus rendering the development of arteriosclerosis difficult, which in turn led to the recognition of the significance of blood HDL, as well as significance of CETP that mediates transfer of CE in HDL into blood LDL. While many attempts have been made in recent years to develop a drug that inhibits such activity of CETP, a compound having a satisfactory activity has not been developed yet.

For purposes of interpreting this specification, the following definitions will apply and whenever appropriate, terms used in the singular will also include the plural and vice versa.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. When an alkyl group includes one or more unsaturated bonds, it can be referred to as an alkenyl (double bond) or an alkynyl (triple bond) group. If the alkyl group can be substituted, it is preferably substituted by 1, 2 or 3 substituents selected from hydroxy, halogen, nitro, carboxy, thiol, cyano, HSO3-, cycloalkyl, alkenyl, alkoxy, cycloalkoxy, alkenyloxy, alkoxycarbonyl, carbamimidoyl, alkyl-S—, alkyl-SO—, alkyl-SO2-, amino, H2N—SO2-, alkanoyl, or heterocyclyl, more preferably selected from hydroxy, halogen, nitro, carboxy, thiol, cyano, alkoxy, or amino.

The term "aryl" refers to monocyclic or bicyclic aromatic hydrocarbon groups having 6-20 carbon atoms in the ring portion. Preferably, the aryl is a (C6-C10) aryl. Non-limiting examples include phenyl, biphenyl, naphthyl or tetrahydronaphthyl, most preferably phenyl, each of which may optionally be substituted by 1-4 substituents, such as alkyl, haloalkyl such as trifluoromethyl, cycloalkyl, halogen, hydroxy, alkoxy, alkyl-C(O)—O—, aryl-O—, heteroaryl-O—, amino, acyl, thiol, alkyl-S—, aryl-S—, nitro, cyano, carboxy, alkyl-O—C(O)—, carbamoyl, alkyl-S(O)—, sulfonyl, sulfonamido, heterocyclyl, alkenyl, haloalkoxy, cycloalkoxy, alkenyloxy, alkoxycarbonyl, alkyl-SO—, alkyl-SO2-, amino, mono- or di-substituted (alkyl, cycloalkyl, aryl and/or aryl alkyl)amino or H2N—SO2.

Furthermore, the term "aryl" as used herein, refers to an aromatic substituent which can be a single aromatic ring, or multiple aromatic rings that are fused together, linked covalently, or linked to a common group such as a methylene or ethylene moiety. The common linking group also can be a carbonyl as in benzophenone or oxygen as in diphenylether or nitrogen as in diphenylamine.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-7, more preferably about 1-4 carbons.

As used herein, the term "acyl" refers to a group R—C(O)— of from 1 to 10 carbon atoms of a straight, branched, or cyclic configuration or a combination thereof, attached to the parent structure through carbonyl functionality. Such group can be saturated or unsaturated, and aliphatic or aromatic. Preferably, R in the acyl residue is alkyl, or alkoxy, or aryl, or heteroaryl. When R is alkyl then the moiety is referred to a alkanoyl. Also preferably, one or more carbons in the acyl residue may be replaced by nitrogen, oxygen or sulfur as long as the point of attachment to the parent remains at the carbonyl. Examples include but are not limited to, acetyl, benzoyl, propionyl, isobutyryl, t-butoxycarbonyl, benzyloxycarbonyl and the like. Lower acyl refers to acyl containing one to four carbons.

As used herein, the term "acylamino" refers to acyl-NH—, wherein "acyl" is defined herein. As used herein, the term "carbamoyl" refers to H$_2$NC(O)—, alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aryl-alkyl-NHC(O)—, alkyl(aryl-alkyl)-NC(O)— and the like.

As used herein, the term "sulfonyl" refers to R—SO$_2$—, wherein R is hydrogen, alkyl, aryl, hetereoaryl, aryl-alkyl, heteroaryl-alkyl, aryl-O—, heteroaryl-O—, alkoxy, aryloxy, cycloalkyl, or heterocyclyl.

As used herein, the term "sulfonamido" refers to alkyl-S(O)$_2$—NH—, aryl-S(O)$_2$—NH—, aryl-alkyl-S(O)$_2$—NH—, heteroaryl-S(O)$_2$—NH—, heteroaryl-alkyl-S(O)$_2$—NH—, alkyl-S(O)$_2$—N(alkyl)-, aryl-S(O)$_2$—N (alkyl)-, aryl-alkyl-S(O)$_2$—N(alkyl)-, heteroaryl-S(O)$_2$—N(alkyl)-, heteroaryl-alkyl-S(O)$_2$—N(alkyl)- and the like.

As used herein, the term "alkoxycarbonyl" or "alkyl-O—C(O)—" refers to alkoxy-C(O)—, wherein alkoxy is defined herein.

As used herein, the term "alkanoyl" refers to alkyl-C(O)—, wherein alkyl is defined herein.

As used herein, the term "alkenyl" refers to a straight or branched hydrocarbon group having 2 to 20 carbon atoms and that contains at least one double bonds. The alkenyl groups preferably have about 2 to 8 carbon atoms.

As used herein, the term "alkenyloxy" refers to alkenyl-O—, wherein alkenyl is defined herein.

As used herein, the term "cycloalkoxy" refers to cycloalkyl-O—, wherein cycloalkyl is defined herein.

As used herein, the term "heterocyclyl" or "heterocyclo" refers to an optionally substituted, fully saturated or unsaturated, aromatic or nonaromatic cyclic group, e.g., which is a 4- to 7-membered monocyclic, 7- to 12-membered bicyclic or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, triazolyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxoazepinyl, azepinyl, piperazinyl, piperidinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, 1,1,4-trioxo-1,2,5-thiadiazolidin-2-yl and the like.

Exemplary bicyclic heterocyclic groups include indolyl, dihydroidolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]-pyridinyl] or furo[2,3-b]pyridinyl), dihydroisoindolyl, 1,3-dioxo-1,3-dihydroisoindol-2-yl, dihydroquinazolinyl (such as 3,4-dihydro-4-oxo-quinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

When heterocyclyl is aromatic, this moiety is referred to as "heteroaryl".

As used herein, the term "heteroaryl" refers to a 5-14 membered monocyclic- or bicyclic- or fused polycyclic-ring system, having 1 to 8 heteroatoms selected from N, O or S. Preferably, the heteroaryl is a 5-10 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinolinyl, 1-, 3-, 4-, 5-, 6-, 7-, or 8-isoquinolinyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-2-, 3-, 4-, 5-, 6-, 7-, or 8-carbazolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroaryl groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

A heteroaryl group may be mono-, bi-, tri-, or polycyclic, preferably mono-, bi-, or tricyclic, more preferably mono- or bicyclic.

The term "heterocyclyl" further refers to heterocyclic groups as defined herein substituted with 1, 2 or 3 substituents selected from the groups consisting of the following: alkyl; haloalkyl, hydroxy (or protected hydroxy); halo; oxo, i.e., =O; amino, mono- or di-substituted (alkyl, cycloalkyl, aryl and/or aryl alkyl)amino such as alkylamino or dialkylamino; alkoxy; cycloalkyl; alkenyl; carboxy; heterocyclooxy, wherein heterocyclooxy denotes a heterocyclic group bonded through an oxygen bridge; alkyl-O—C(O)—; mercapto; HSO3; nitro; cyano; sulfamoyl or sulfonamido; aryl; alkyl-C(O)—O—; aryl-C(O)—O—; aryl-S—; cycloalkoxy; alkenyloxy; alkoxycarbonyl; aryloxy; carbamoyl; alkyl-S—; alkyl-SO—, alkyl-SO2-; formyl, i.e., HC(O)—; aryl-alkyl—; acyl such as alkanoyl; heterocyclyl and aryl substituted with alkyl, cycloalkyl, alkoxy, hydroxy, amino, alkyl-C(O)—NH—, alkylamino, dialkylamino or halogen.

As used herein, the term "cycloalkyl" refers to optionally substituted saturated or unsaturated monocyclic, bicyclic or tricyclic hydrocarbon groups of 3-12 carbon atoms, each of which may be substituted by one or more substituents, such as alkyl, halo, oxo, hydroxy, alkoxy, alkanoyl, acylamino, carbamoyl, alkyl-NH—, (alkyl)$_2$N—, thiol, alkylthio, nitro, cyano, carboxy, alkyl-O—C(O)—, sulfonyl, sulfonamido, sulfamoyl, heterocyclyl and the like. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

As used herein, the term "sulfamoyl" refers to H2NS(O)$_2$—, alkyl-NHS(O)$_2$—, (alkyl)$_2$NS(O)$_2$—, aryl-NHS(O)$_2$—, alkyl(aryl)-NS(O)$_2$—, (aryl)$_2$NS(O)$_2$—, heteroaryl-NHS(O)$_2$—, aryl-alkyl-NHS(O)$_2$—, heteroaryl-alkyl-NHS(O)$_2$— and the like.

As used herein, the term "aryloxy" refers to both an —O-aryl and an —O— heteroaryl group, wherein aryl and heteroaryl are defined herein.

As used herein, the term "halogen" or "halo" refers to fluoro, chloro, bromo, and iodo.

As used herein, the term "haloalkyl" refers to an alkyl as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Preferably, the polyhaloalkyl contains up to 12, 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

As used herein, the term "dialkylamino" refers to an to an amino group which is di-substituted by alkyl, whereby the alkyl can be the same or different, as defined herein. Preferably the dialkylamino can have the same alkyl substitutent. Non-limiting examples of dialkylamino include dimethylamino, diethylamino and diisopropylamino.

As used herein, the term "aryl alkyl" is interchangeable for "aryl-alkyl-", wherein aryl and alkyl are defined herein.

As used herein, the term "cycloalkyl-alkyl-" is interchangeable for "cycloalkyl alkyl", wherein cycloalkyl and alkyl are defined herein.

As used herein, the term "isomers" refers to different compounds that have the same molecular formula. Also as used herein, the term "an optical isomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the term "pharmaceutically acceptable salts" refers to salts that retain the biological effectiveness and properties of the compounds of this invention and, which are not biologically or otherwise undesirable. Non-limiting examples of the salts include non-toxic, inorganic and organic base or acid addition salts of compounds of the present invention. In many cases, the compounds of the present invention are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in Remington's Pharmaceutical Sciences, 20th ed., Mack Publishing Company, Easton, Pa., (1985), which is herein incorporated by reference.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The term "therapeutically effective amount" of a compound of the present invention refers to an amount of the compound of the present invention that will elicit the biological or medical response of a subject, or ameliorate symptoms, slow or delay disease progression, or prevent a disease, etc. In a preferred embodiment, the "effective amount" refers to the amount that inhibits or reduces expression or activity of CETP.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "a disorder" or "a disease" refers to any derangement or abnormality of function; a morbid physical or mental state. See Dorland's Illustrated Medical Dictionary, (W.B. Saunders Co. 27th ed. 1988).

As used herein, the term "inhibition" or "inhibiting" refers to the reduction or suppression of a given condition, symptom, or disorder, or disease, or a significant decrease in the baseline activity of a biological activity or process. Preferably, the condition or symptom or disorder or disease is mediated by CETP activity or responsive to the inhibition of CETP.

As used herein, the term "treating" or "treatment" of any disease or disorder refers in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context. Recitation of ranges of values herein are merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The following preferred embodiments of the moieties and symbols in formula I can be employed independently of each other to replace more general definitions and thus to define specially preferred embodiments of the invention, where the remaining definitions can be kept broad as defined in embodiments of the inventions defined above of below.

In one embodiment, the invention is related to a compound of formula I wherein
R1 is heterocyclyl, aryl, alkoxycarbonyl, alkanoyl, or alkyl, wherein each heterocyclyl or aryl is optionally substituted with one to three substituents selected from alkyl, haloalkyl, hydroxy, halogen, nitro, carboxy, thiol, cyano, HSO3-, cycloalkyl, alkenyl, alkoxy, cycloalkoxy, alkenyloxy, alkoxycarbonyl, carbamoyl, alkyl-S—, alkyl-SO—, alkyl-SO2-, amino, H2N—SO2-, alkanoyl, or heterocyclyl; and wherein each alkanoyl, alkoxycarbonyl, or alkyl is optionally substituted with one to three substituents selected from hydroxy, halogen, nitro, carboxy, thiol, cyano, HSO3-, cycloalkyl, alkenyl, alkoxy, cycloalkoxy, alkenyloxy, alkoxycarbonyl, carbamoyl, alkyl-S—, alkyl-SO—, alkyl-SO2-, amino, H2N—SO2-, alkanoyl, or heterocyclyl;

R2 is alkyl;
R3 is HO(O)C—R9-C(O)— or HO(O)C—R9-O—C(O)—,
R9 is -alkyl-, -alkyl-cycloalkyl-, -heterocyclyl-, -alkyl-heterocyclyl-, -heterocyclyl-alkyl-, -alkyl-aryl-, -cycloalkyl-, -cycloalkyl-alkyl-, -aryl-, -aryl-alkyl- or -cycloalkyl-alkyl-; or, wherein each R9 is optionally substituted with one to three substituents selected from alkyl, hydroxy, halogen, nitro, carboxy, thiol, cyano, HSO3-, cycloalkyl, alkenyl, alkoxy, cycloalkoxy, alkenyloxy, alkyl-haloalkyl, carboxy, carboxyamide, acyl, alkanoyl, carbamimidoyl, alkyl-S—, alkyl-SO—, alkyl-SO2-, amino, H2N—SO2-, heterocyclyl;
R4 or R5 are independently of each other hydrogen, alkyl, aryl-alkyl-, cycloalkyl-alkyl- or heteroaryl-alkyl-, wherein each aryl, cycloalkyl or heteroary is optionally substituted with one to three substituents selected from alkyl, haloalkyl, hydroxy, halogen, nitro, carboxy, thiol, cyano, HSO3-, cycloalkyl, alkenyl, alkoxy, haloalkoxy, cycloalkoxy, alkenyloxy, alkoxycarbonyl, alkyl-S—, alkyl-SO—, alkyl-SO2-, amino, mono- or di-substituted (alkyl, cycloalkyl, aryl and/or aryl-alkyl-) amino; H2N—SO2-, or alkanoyl;
R6 and R7 are independently hydrogen, alkyl, haloalkyl, halogen, cyano, nitro, hydroxy, dialkylamino or alkoxy; or
R6 is aryl or heteroaryl; or
a pharmaceutically acceptable salt thereof; or an optical isomer thereof; or a mixture of optical isomers.

Preferred Definitions for R1
Preferably, R1 is heterocyclyl, aryl, alkoxycarbonyl, alkanoyl, or alkyl, wherein each heterocyclyl or aryl is optionally substituted with one to three substituents selected from alkyl, haloalkyl, hydroxy, halogen, nitro, carboxy, thiol, cyano, HSO3-, cycloalkyl, alkenyl, alkoxy, cycloalkoxy, alkenyloxy, alkoxycarbonyl, carbamoyl, alkyl-S—, alkyl-SO—, alkyl-SO2-, amino, H2N—SO2-, alkanoyl, or heterocyclyl; and wherein each alkanoyl, alkoxycarbonyl, or alkyl is optionally substituted with one to three substituents selected from hydroxy, halogen, nitro, carboxy, thiol, cyano, HSO3-, cycloalkyl, alkenyl, alkoxy, cycloalkoxy, alkenyloxy, alkoxycarbonyl, carbamoyl, alkyl-S—, alkyl-SO—, alkyl-SO2-, amino, H2N—SO2-, alkanoyl, or heterocyclyl. More preferably, R1 is cycloalkyl, heterocyclyl, heteroaryl, alkanoyl or alkoxycarbonyl, wherein each heterocyclyl is optionally substituted with one to three substituents selected from alkyl, hydroxy, halogen, nitro, carboxy, thiol, cyano, HSO3-, cycloalkyl, alkenyl, alkoxy, cycloalkoxy, alkenyloxy, alkoxycarbonyl, carbamoyl, alkyl-S—, alkyl-SO—, alkyl-SO2-, amino, H2N—SO2-, alkanoyl, or heterocyclyl, more preferably alkyl, hydroxy, halogen, carboxy, alkoxy, amino, alkanoyl or heterocyclyl. Preferred examples for the heterocyclyl substituent of the heterocyclyl moiety for R1 is a 5- to 6-membered, preferably fully saturated ring containing at least one heteroatom selected from O, N or S, more preferably N, most preferably it is morpholinyl.

A preferred meaning of variable R1 is heteroaryl as preferably represented by formulae

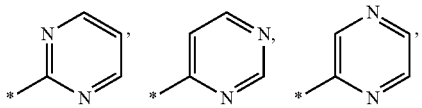

or pyridyl, especially which are each unsubstituted or substituted by C1-C4-alkyl, especially methyl or halo, aryl, heterocyclyl or heteroaryl. A preferred substituent for

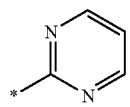

is morpholinyl, or pyrazole which is unsubstituted or substituted by C1-C4-alkyl.

Preferred Definitions for R2
Preferably, R2 is straight chain or branched C1-C6 alkyl as defined herein. Examples include methyl, ethyl, isopropyl, n-propyl, isobutyl, n-butyl or sec-butyl, more preferably ethyl or isobutyl, most preferably ethyl.

Preferred Definitions for R3
Preferably R3 is HO(O)C—R9-C(O)— or HO(O)C—R9-O—C(O)—.

Preferred Definitions for R9
Preferably R9 is -alkyl-, -alkyl-cycloalkyl-, -heterocyclyl-, -alkyl-heterocyclyl-, -heterocyclyl-alkyl-, -alkyl-aryl-, -cycloalkyl-, -cycloalkyl-alkyl-, -aryl-, -aryl-alkyl- or -cycloalkyl-alkyl-; or, wherein each R9 is optionally substituted with one to three substituents selected from alkyl, hydroxy, halogen, nitro, carboxy, thiol, cyano, HSO3-, cycloalkyl, alkenyl, alkoxy, cycloalkoxy, alkenyloxy, alkyl-haloalkyl, carboxy, carboxyamide, acyl, alkanoyl, carbamimidoyl, alkyl-S—, alkyl-SO—, alkyl-SO2-, amino, H2N—SO2-, heterocyclyl;

Most preferable is $C_{2-5}$alkyl, $C_{4-6}$cycloalkyl, —CH$_2$—$C_{4-6}$cycloalkyl, $C_{4-6}$cycloalkyl-CH$_2$—, $C_{5-6}$ aryl, $C_{4-6}$ heterocyclyl or $C_{5-6}$ heteroaryl. Most preferred are

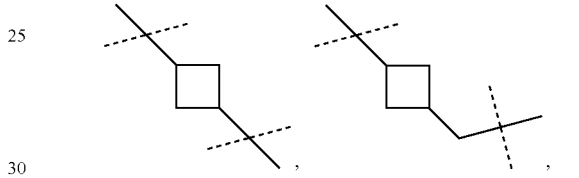

CH2C(CH3)2CH2CH2-,

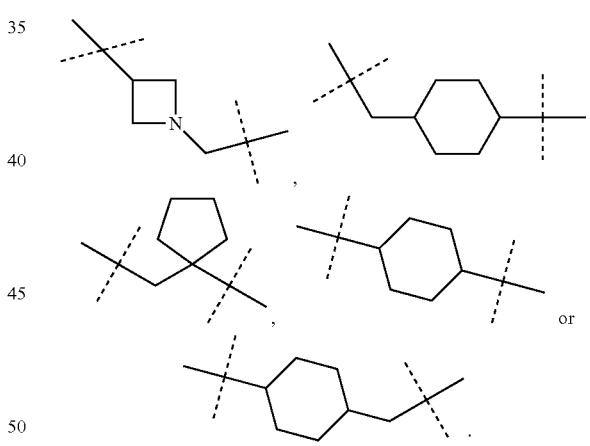

Preferred Definitions for R4 and R5
Preferably R4 or R5 are independently of each other hydrogen, alkyl, cycloalkyl, aryl, heteroaryl, aryl-alkyl-, cycloalkyl-alkyl- or heteroaryl-alkyl-, more preferably hydrogen, aryl-alkyl-, cycloalkyl-alkyl- or heteroaryl-alkyl-, wherein each alkyl, is optionally substituted with one to three substituents selected from hydroxy, halogen, nitro, carboxy, thiol, cyano, HSO3-, cycloalkyl, alkenyl, alkoxy, haloalkoxy, cycloalkoxy, alkenyloxy, alkoxycarbonyl, alkyl-S—, alkyl-SO—, alkyl-SO2-, amino, mono- or di-substituted (alkyl, cycloalkyl, aryl and/or aryl-alkyl-) amino; H2N—SO2-, or alkanoyl, and wherein each aryl, cycloalkyl or heteroaryl is optionally substituted with one to three substituents selected from alkyl, haloalkyl, hydroxy, halogen, nitro, carboxy, thiol, cyano, HSO3-, cycloalkyl, alkenyl, alkoxy, haloalkoxy, cycloalkoxy, alkenyloxy, alkoxycarbonyl, alkyl-S—, alkyl- SO—, alkyl-SO2-, amino, mono- or di-substituted (alkyl, cycloalkyl, aryl and/or aryl-alkyl-) amino; H2N—SO2-, or alkanoyl.

More preferably R4 or R5 are independently of each other hydrogen, benzyl, or cycloalkyl-CH2-, wherein each benzyl or cycloalkyl is optionally substituted with one to three substituents selected from alkyl, haloalkyl, hydroxy, halogen, nitro, carboxy, thiol, cyano, HSO3-, alkoxy, haloalkoxy, amino, mono- or di-substituted (alkyl, cycloalkyl, aryl and/or aryl-alkyl-) amino; H2N—SO2-, or alkanoyl.

In one embodiment, one of R4 and R5, preferably R5, is hydrogen and the other, preferably R4, is a group as defined herein other than hydrogen.

In another embodiment, both R4 and R5 are hydrogen.

Most preferably, R4 is ethyl or benzyl. It is also preferred that in this case R5 is hydrogen.

Preferred Definitions for R6 and R7

Preferably, R6 and R7 are independently hydrogen, alkyl, haloalkyl, halogen, or alkoxy.

More preferably, R6 and R7 are independently hydrogen, alkyl or haloalkyl, such as trifluoromethyl.

In one embodiment, one of R6 and R7 is hydrogen and the other is a group as defined herein other than hydrogen.

In another preferred embodiment, both R6 and R7 are the same and are as defined herein, most preferably trifluoromethyl.

The positions of R6 and R7 on the phenyl ring are preferably as follows:

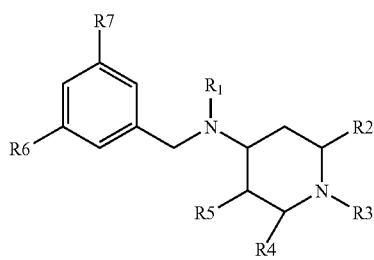

Any asymmetric carbon atom on the compounds of the present invention can be present in the (R)-, (S)- or (R,S)-configuration, preferably in the (R)- or (S)-configuration. Substituents at atoms with unsaturated bonds may, if possible, be present in cis-(Z)- or trans-(E)-form. Therefore, the compounds of the present invention can be in the form of one of the possible isomers or mixtures thereof, for example, as substantially pure geometric (cis or trans) isomers, diastereomers, optical isomers (antipodes), racemates or mixtures thereof.

Preferred isomers of the compound of the present invention can be represented by the following formula:

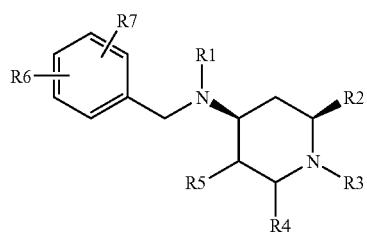

in particular:

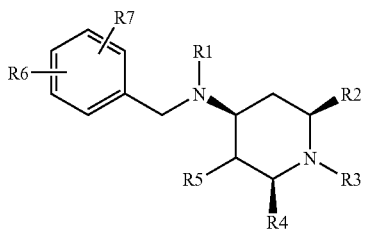

Any resulting mixtures of isomers can be separated on the basis of the physicochemical differences of the constituents, into the pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, the imidazolyl moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Finally, compounds of the present invention are either obtained in the free form, as a salt thereof, or as prodrug derivatives thereof.

When a basic group is present in the compounds of the present invention, the compounds can be converted into acid addition salts thereof, in particular, acid addition salts with the imidazolyl moiety of the structure, preferably pharmaceutically acceptable salts thereof. These are formed, with inorganic acids or organic acids. Suitable inorganic acids include but are not limited to, hydrochloric acid, sulfuric acid, a phosphoric or hydrohalic acid. Suitable organic acids include but are not limited to, carboxylic acids, such as (C1-C4) alkanecarboxylic acids which, for example, are unsubstituted or substituted by halogen, e.g., acetic acid, such as saturated or unsaturated dicarboxylic acids, e.g., oxalic, succinic, maleic or fumaric acid, such as hydroxycarboxylic acids, e.g., glycolic, lactic, malic, tartaric or citric acid, such as amino acids, e.g., aspartic or glutamic acid, organic sulfonic acids, such as (C1-C4)alkylsulfonic acids, e.g., methanesulfonic acid; or arylsulfonic acids which are unsubstituted or substituted, e.g., by halogen. Preferred are salts formed with hydrochloric acid, methanesulfonic acid and maleic acid.

When an acidic group is present in the compounds of the present invention, the compounds can be converted into salts with pharmaceutically acceptable bases. Such salts include alkali metal salts, like sodium, lithium and potassium salts; alkaline earth metal salts, like calcium and magnesium salts; ammonium salts with organic bases, e.g., trimethylamine salts, diethylamine salts, tris(hydroxymethyl)methylamine salts, dicyclohexylamine salts and N-methyl-D-glucamine salts; salts with amino acids like arginine, lysine and the like. Salts may be formed using conventional methods, advantageously in the presence of an ethereal or alcoholic solvent, such as a lower alkanol. From the solutions of the latter, the salts may be precipitated with ethers, e.g., diethyl ether.

Resulting salts may be converted into the free compounds by treatment with acids. These or other salts can also be used for purification of the compounds obtained.

When both a basic group and an acid group are present in the same molecule, the compounds of the present invention can also form internal salts.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See The Practice of Medicinal Chemistry, Ch. 31-32 (Ed. Wermuth, Academic Press, San Diego, Calif., 2001). Generally, bioprecursor prodrugs are compounds are inactive or have low activity compared to the corresponding active drug compound, that contains one or more protective groups and are converted to an active form by metabolism or solvolysis. Both the active drug form and any released metabolic products should have acceptably low toxicity. Typically, the formation of active drug compound involves a metabolic process or reaction that is one of the follow types:

1. Oxidative reactions, such as oxidation of alcohol, carbonyl, and acid functions, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-delakylation, oxidative O- and S-delakylation, oxidative deamination, as well as other oxidative reactions.
2. Reductive reactions, such as reduction of carbonyl groups, reduction of alcoholic groups and carbon-carbon double bonds, reduction of nitrogen-containing functions groups, and other reduction reactions.
3. Reactions without change in the state of oxidation, such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. See, Cheng et al., US20040077595, application Ser. No. 10/656, 838, incorporated herein by reference. Such carrier prodrugs are often advantageous for orally administered drugs. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxy groups with lipophilic carboxylic acids, or of carboxylic acid groups with alcohols, e.g., aliphatic alcohols. Wermuth, The Practice of Medicinal Chemistry, Ch. 31-32, Ed. Werriuth, Academic Press, San Diego, Calif., 2001.

Exemplary prodrugs are, e.g., esters of free carboxylic acids and S-acyl and O-acyl derivatives of thiols, alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, J. Med. Chem. 2503 (1989)). Moreover, drugs containing an acidic NH group, such as imidazole, imide, indole and the like, have been masked with N-acyloxymethyl groups (Bundgaard, Design of Prodrugs, Elsevier (1985)). Hydroxy groups have been masked as esters and ethers. EP 039,051 (Sloan and Little) discloses Mannich-base hydroxamic acid prodrugs, their preparation and use.

In view of the close relationship between the compounds, the compounds in the form of their salts and the pro-drugs, any reference to the compounds of the present invention is to be understood as referring also to the corresponding pro-drugs of the compounds of the present invention, as appropriate and expedient.

Furthermore, the compounds of the present invention, including their salts, can also be obtained in the form of their hydrates, or include other solvents used for their crystallization.

The compounds of the present invention have valuable pharmacological properties. The compounds of the present invention are useful as inhibitors for cholesteryl ester transfer protein (CETP). CETP is a 74 KD glycopeptide, it is secreted by the liver and is a key player in facilitating the transfer of lipids between the various lipoproteins in plasma. The primary function of CETP is to redistribute cholesteryl esters (CE) and triglycerides between lipoproteins. See Assmann, G et al., "HDL cholesterol and protective factors in atherosclerosis," Circulation, 109: 1118-1114 (2004). Because most triglycerides in plasma originate in VLDLs and most CEs are formed in HDL particles in the reaction catalyzed by lecithin: cholesterol acyltransferase, activity of CETP results in a net mass transfer of triglycerides from VLDLs to LDLs and HDLs and a net mass transfer of CEs from HDLs to VLDLs and LDLs. Thus, CETP potentially decreases HDL-C levels, increases LDL-cholesteryl (LDL-C) levels and reduces HDL and LDL particles size, and inhibition of CETP could be a therapeutic strategy for raising HDL-cholesteryl (HDL-C), have a favorable impact on the lipoprotein profile, and reduce the risk of cardiovascular diseases. Accordingly, the compounds of the present invention as CETP inhibitors are useful for the delay of progression and/or treatment of a disorder or disease that is mediated by CETP or responsive to inhibition of CETP. Disorders, conditions and diseases that can be treated with the compounds of the present invention include but are not limited to, hyperlipidemia, arteriosclerosis, atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorder, coronary heart disease, coronary artery disease, coronary vascular disease, angina, ischemia, heart ischemia, thrombosis, cardiac infarction such as myocardial infarction, stroke, peripheral vascular disease, reperfusion injury, angioplasty restenosis, hypertension, congestive heart failure, diabetes such as type II diabetes mellitus, diabetic vascular complications, obesity, infection or egg embryonation of schistosoma, or endotoxemia etc.

Additionally, the present invention provides:
  a compound of the present invention as described herein above for use as a medicament;
  the use of a compound of the present invention as described herein above for the preparation of a pharmaceutical composition for the delay of progression and/or treatment of a disorder or disease mediated by CETP, or responsive to inhibition of CETP.
  the use of a compound of the present invention as described herein above for the preparation of a pharmaceutical composition for the delay of progression and/or treatment of a disorder or disease selected from hyperlipidemia, arteriosclerosis, atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorder, coronary heart disease, coronary artery disease, coronary vascular disease, angina, ischemia, heart ischemia, thrombosis, cardiac infarction such as myocardial infarction, stroke, peripheral vascular disease, reperfusion injury, angioplasty restenosis, hypertension, congestive heart failure, diabetes such as type II diabetes mellitus, diabetic vascular complications, obesity or endotoxemia etc.

The compounds of formula (I) can be prepared by the procedures described in the following sections.

Generally, the compounds of formula (I) can be prepared according to the following general procedures and schemes. In all these Schemes the variants R1, R2, R3, R4, R5, R6, R7 and R8 have the meaning as set forth herein unless defined otherwise.

1. General Procedure A: Using Piperidinone A1

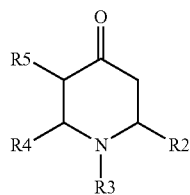

(A1)

Route AI when R4 and R5 are hydrogen:

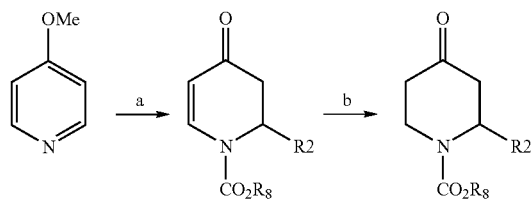

a-1: ClCO$_2$R8; then R$_2$Mx, or
a-2: ClCO$_2$Ph; then R$_2$Mx; then KOR8, or
a-3: For R8=t-Bu, a-2 or Boc$_2$O; then R2Mx wherein R8 is as defined herein e.g. t-Bu, Bn, 2,2,2-trichloroethyl, allyl, Mx is e.g. MgBr, MgI, MgCl, Li, also combination with ZnCl2.

In step b) standard conditions for 1,4-reductions may be employed, such as Mg, alcohol; CeCl3, NaBH4, or catalytic hydrogenation.

Route AII when R4 and R5 are hydrogen:

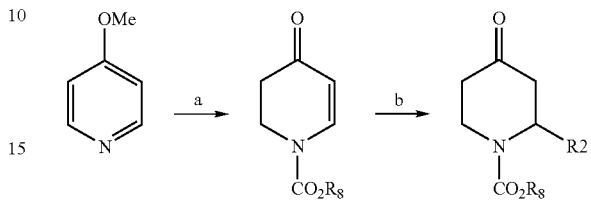

a-1: ClCO$_2$R8; then hydride agent, or
a-2: ClCO$_2$Ph; then hydride agent; then KOR8, or
a-3: For R8=t-Bu, a-2 or Boc$_2$O; then hydride agent wherein R8 is as defined herein e.g. t-Bu, Bn, 2,2,2-trichloroethyl, allyl. Suitable hydride agents that can be used are such as NaBH(OAc)$_3$, NaBH(CN)$_3$, NaBH4, or LiBH4, K(OiPr)BH NaB[CH(CH)CH]H, or NaAlH(OCHCHOCH).

In step b) standard conditions for 1,4-additions are employed such as R2MgX (X=halo), CuI or R22Zn, cat. Cu species.

Route AIII when R5 is hydrogen:

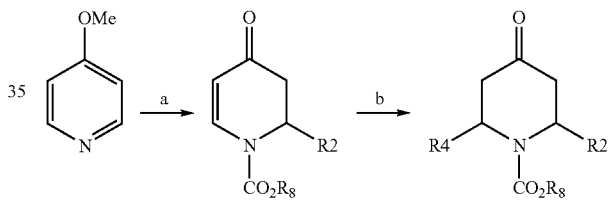

a-1: ClCO$_2$R8; then R$_2$Mx, or
a-2: ClCO$_2$Ph; then R$_2$Mx; then KOR8, or
a-3: For R8=t-Bu, a-2 or Boc$_2$O; then R2Mx wherein R$_8$ is as defined herein e.g. t-Bu, Bn, 2,2,2-trichloroethyl, allyl, Mx is e.g. MgBr, MgI, MgCl, Li, also combination with ZnCl2.

In step b) standard conditions for 1,4-additions are employed such as R4MgX (X=halo), CuI or R42Zn, cat. Cu species.

Route AIV when R5 is hydrogen:

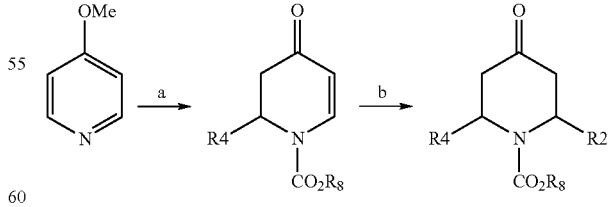

a-1: ClCO$_2$R8; then R4Mx, or
a-2: ClCO$_2$Ph; then R4Mx; then KOR8, or
a-3: For R8=t-Bu, a-2 or Boc$_2$O; then R4Mx wherein R8 is as defined herein e.g. t-Bu, Bn, 2,2,2-trichloroethyl, allyl, Mx is e.g. MgBr, MgI, MgCl, Li, also combination with ZnCl2.

In step b) standard conditions for 1,4-additions are employed such as R2MgX (X=halo), CuI or R22Zn, cat. Cu species.

Route AV when R4 is Hydrogen:

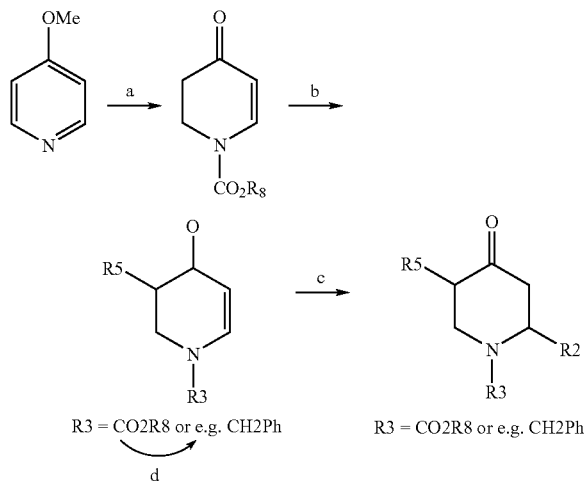

a-1: ClCO₂R8; then hydride agent, or
a-2: ClCO₂Ph; then hydride agent; then KOR8, or
a-3: For R₈=t-Bu, a-2 or Boc₂O; then hydride agent d
wherein R8 is as defined herein. Suitable hydride agents that can be used are such as NaBH(OAc)3, NaBH(CN)3, NaBH4, or LiBH4, K(OiPr)BH NaB[CH(CH)CH]H, or NaAlH (OCHCHOCH).

In step b) standard conditions for alkylations are employed, such as strong base and a halide LDA, R5X or LHMDS or KHMDS, R5X (X=halogen or OMs, OTs, OTf).

In step c) standard conditions for 1,4-additions are employed such as R2MgX (X=halo), CuI or R22Zn, cat. Cu species.

Conversion of R3 can be effected by standard functional group manipulation as well known in the art or as specifically described herein.

Route AVI when R4 is Hydrogen:

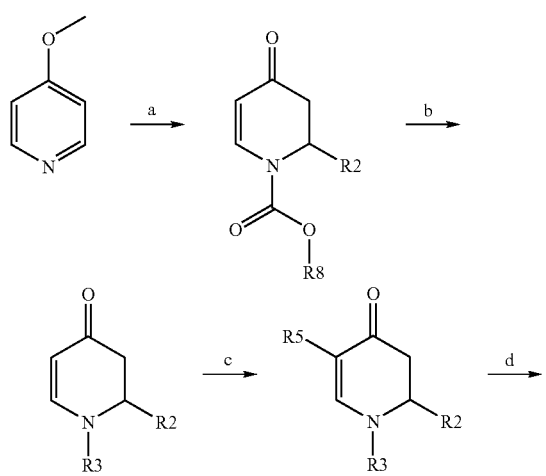

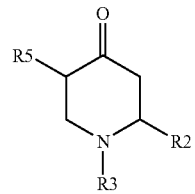

a-1: ClCO₂R8; then R2Mx, or
a-2: ClCO₂Ph; then R2Mx; then KOR8, or
a-3: For R8=t-Bu, a-2 or BOC₂O; then R2Mx
wherein R8 and R3 are as defined herein; Mx is e.g. MgBr, MgI, MgCl, Li, also combination with ZnCl2.

In step b) the conversion of R3 can be effected by standard functional group manipulation as well known in the art or as specifically described herein.

In step c) standard conditions for enamine alkylations are employed, such as R5X (X=halogen or OMs, OTs, OTf); heat; or 12 and the use of a base to form a vinyl iodide followed by cross-coupling conditions such as Suzuki, Stille, Negishi or Kumada as described e.g. in standard textbooks.

In step d) standard conditions for 1,4-reductions may be employed, such as Mg, alcohol; CeCl3, NaBH4, or catalytic hydrogenation.

Route AVII:

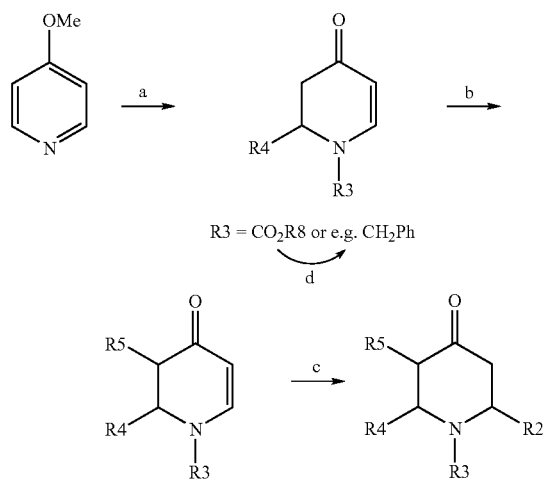

a-1: ClCO₂R8; then R4Mx, or
a-2: ClCO₂Ph; then R4Mx; then KOR8, or
a-3: For R8=t-Bu, a-2 or Boc₂O; then R4Mx
wherein R8 and R3 are as defined herein; Mx is e.g. MgBr, MgI, MgCl, Li, also combination with ZnCl2.

In step b) standard conditions for alkylations are employed, such as strong base and a halide; e.g. LDA, R4X or LHMDS or KHMDS, R4X (X=halogen or OMs, OTs, OTf).

In step c) standard conditions for 1,4-additions are employed such as R5MgX (X=halo), CuI or R52Zn, cat. Cu species.

In step d) the conversion of R3 can be effected by standard functional group manipulation as well known in the art or as specifically described herein.

Using any of the routes AI to AVII above, the piperidone A1 can be converted into the compound of formula (I) using one of the routes AVIII, AIX or AX shown below.

Route AVIII:

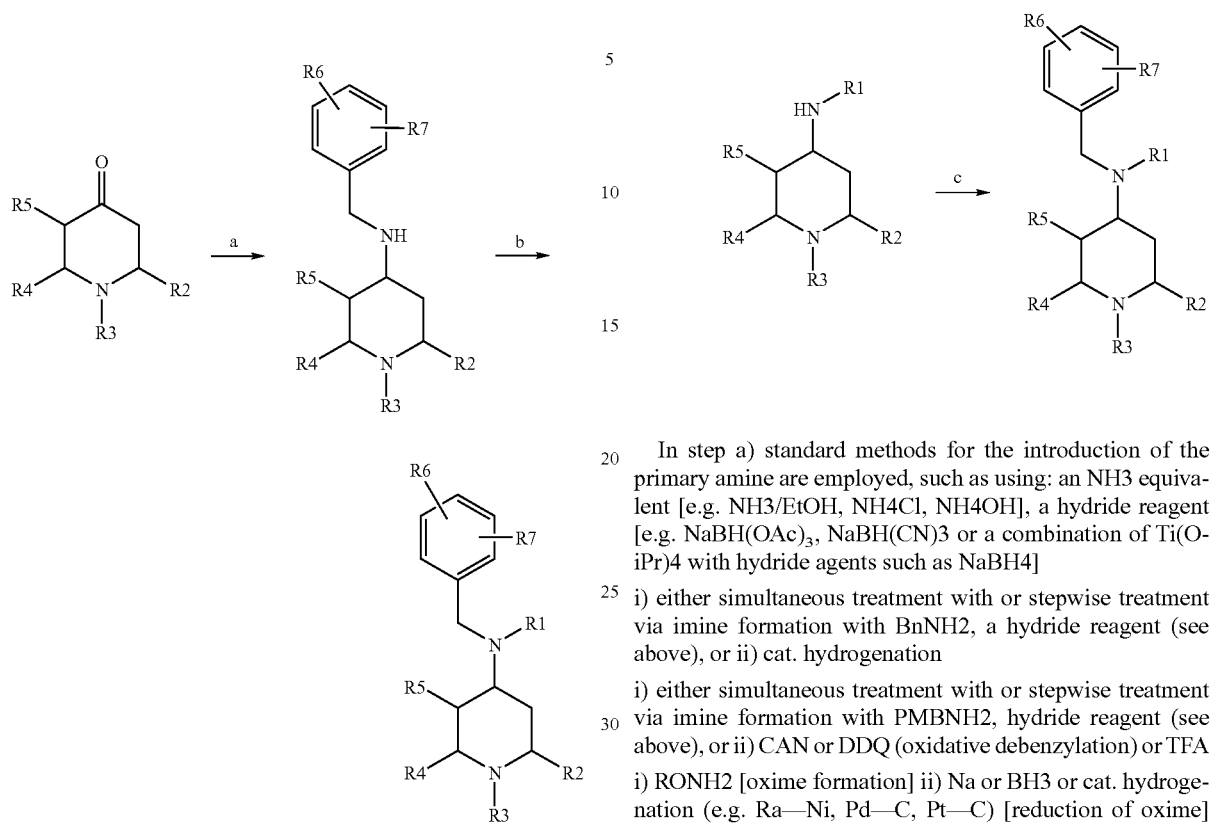

In step a) standard methods for reductive amination are employed, such as ArCH2NH2, hydride reagent [ex. NaBH (OAc)3, NaBH(CN)3, NaBH4, LiBH4, BH3, picoline borane, borane-pyridine complex]; or Ti(OiPr)4; then hydride reagent such as NaBH(OAc)3, NaBH(CN)3, NaBH4, LiBH4, borane, picoline borane, borane-pyridine complex, LiAlH4, 9-BBN, Alpine borane R®, LiB(s-Bu)3H, LiB(Sia)3H; or imine formation catalyzed or uncatalyzed by acid followed by reduction by hydride agents (see above).

In step b), group R1 is introduced by usual functional group manipulation in the amine, such as alkylation, carbamate formation, urea formation, SRN1 substitution, aryl amination and reductive amination.

The group R3 may be modified at an appropriate stage to have the desired definition as set forth in the claims be standard nitrogen protecting group chemistry as known in the art or as described herein.

Route AIX:

In step a) standard methods for the introduction of the primary amine are employed, such as using: an NH3 equivalent [e.g. NH3/EtOH, NH4Cl, NH4OH], a hydride reagent [e.g. NaBH(OAc)$_3$, NaBH(CN)3 or a combination of Ti(O-iPr)4 with hydride agents such as NaBH4]

i) either simultaneous treatment with or stepwise treatment via imine formation with BnNH2, a hydride reagent (see above), or ii) cat. hydrogenation i) either simultaneous treatment with or stepwise treatment via imine formation with PMBNH2, hydride reagent (see above), or ii) CAN or DDQ (oxidative debenzylation) or TFA i) RONH2 [oxime formation] ii) Na or BH3 or cat. hydrogenation (e.g. Ra—Ni, Pd—C, Pt—C) [reduction of oxime] whereby R is for example benzyl, p-methoxybenzyl, or allyl.

i) a hydride reagent [reduction to alcohol] ii) Mitsunobu condition using PPh3, DEAD, N3 anion or mesylation with MsCl and base then N3 anion or bromination with conditions such as NBS/PPh3, PBr3/PPh3, CBr4/PPh3 then N3 anion or PBr3/PPh3 then N3 anion iii) PR3 or cat. Hydrogenation [reduction of azide] whereby R is for example ethyl or phenyl In steps b) and c), group R1 or the benzyl ring, respectively, are introduced by usual functional group manipulation in the amine, such as alkylation, carbamate formation, urea formation, SRN1 substitution, aryl amination and reductive amination for step b) and preferably alkylation and reductive amination for step c).

The group R3 may be modified at an appropriate stage to have the desired definition as set forth in the claims be standard nitrogen protecting group chemistry as known in the art or as described herein.

Route AX:

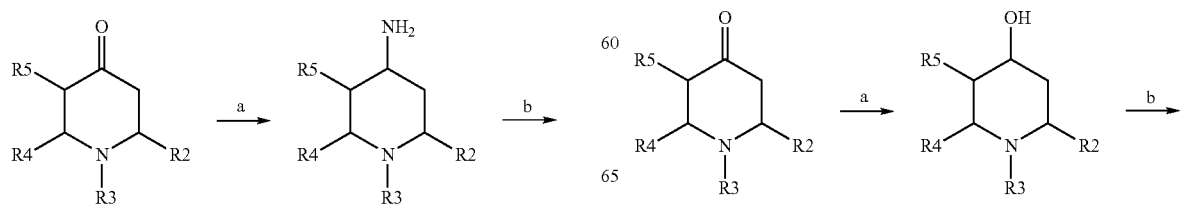

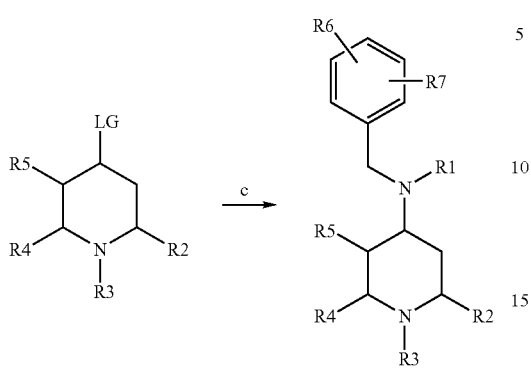

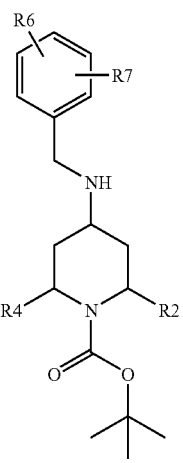

wherein LG is a leaving group such as a mesylate, tosylate, triflate or bromide.

In step a) standard methods to reduce the carbonyl group are employed, such as the use of a hydride agent, e.g. NaBH4 or K-Selectride.

In step b) standard methods for the conversion of the alcohol to a leaving group (LG; e.g. a mesylate, tosylate, or bromide) are employed. The methods include the use of MsCl/base or TsCl/base or SOCl2 or NBS/PPh3 or CBr4/PPh3 or Tf2O using conditions well known in the art.

In step c) the amine unit is introduced using standard substitution chemistry, e.g. by employing the secondary amine and a strong base such as NaH, KOt-Bu, LHMDS.

The group R3 may be modified at an appropriate stage to have the desired definition as set forth in the claims be standard nitrogen protecting group chemistry as known in the art or as described herein.

Route XI:

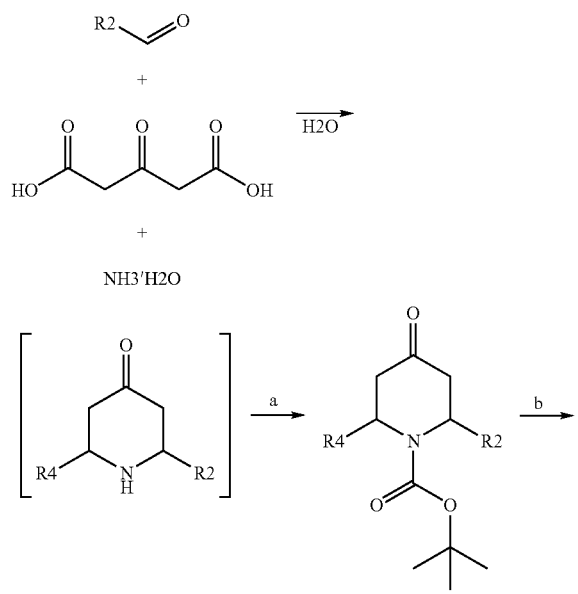

A two step one pot new synthesis is also possible. An intermediate may be prepared via a double mannich reaction by alkylaldehyde, 1,3-dicarboxylic acetone and ammonium. R2 and R4 are equivalent is this case in that R2 and R4 come from the same alkylaldehyde starting material.

In step a) the nitrogen is protected by appropriate protection group (e.g. Boc group).

The group R3 may be modified at an appropriate stage to have the desired definition as set forth in the claims be standard nitrogen protecting group chemistry as known in the art or as described herein.

In step b) standard methods for reductive amination are employed, such as ArCH2NH2, hydride reagent [ex. NaBH(OAc)3, NaBH(CN)3, NaBH4, LiBH4, BH3, picoline borane, borane-pyridine complex]; or Ti(OiPr)4; then hydride reagent such as NaBH(OAc)3, NaBH(CN)3, NaBH4, LiBH4, borane, picoline borane, borane-pyridine complex, LiAlH4, 9-BBN, Alpine borane, LiB(s-Bu)3H, LiB(Sia)3H; or imine formation catalyzed or uncatalyzed by acid followed by reduction by hydride agents.

2. General Procedure B: Using Ritter-Type Chemistry

Details for preparing benzyl-substituted piperidine B1 can be found in bioorganic & Medical Chemistry Letters, Vol. 6, No. 24, pp. 3029-3034, 1996. The methods described therein could be applied analogously obtaining substituted piperidines.

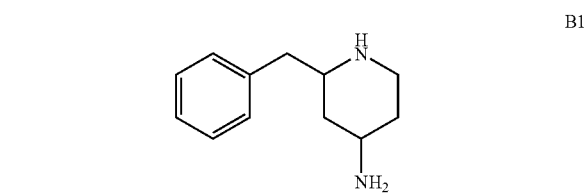

This piperidine could also be further reacted to form a compound of formula (I) by alkylation methods and nitrogen protecting group manipulations as described above in the procedure A.

2. General Procedure C: Using Dieckmann Chemistry

Compounds of formula (I) can be prepared be following the synthetic route outlined in Journal of Medicinal Chemistry, 2001, Vol. 44, No. 6, pp. 972-987 either directly or analogously.

2. General Procedure D: Using Diels-Alder Chemistry

Compounds of formula (I) can be prepared be following the synthetic routes outlined in Tetrahedron Letters, 1999, Vol. 55, No. 6, pp. 7601-7612 or Org. Lett., Vol. 9, No. 21, 2002 pp. 3667-3670 either directly or analogously and converting the obtained piperidinone by methods outlined in e.g. routes AVIII, AIX or AX above.

Racemates and diastereomer mixtures obtained can be separated into the pure isomers or racemates in a known manner on the basis of the physicochemical differences of the components, for example by fractional crystallization or by chiral chromatography or HPLC separation utilizing chiral stationery phases. Racemates obtained may furthermore be resolved into the optical antipodes by known methods, for example by recrystallization from an optically active solvent, chromatography on chiral adsorbents, with the aid of suitable microorganisms, by cleavage with specific immobilized enzymes, via the formation of inclusion compounds, for example using chiral crown ethers, only one enantiomer being complexed, or by conversion into diastereomeric salts, for example by reaction of a basic final substance racemate with an optically active acid, such as a carboxylic acid, for example tartaric or malic acid, or sulfonic acid, for example camphorsulfonic acid, and separation of the diastereomer mixture obtained in this manner, for example on the basis of its differing solubilities, into the diastereomers from which the desired enantiomer can be liberated by the action of suitable agents. The more active enantiomer is advantageously isolated.

In starting compounds and intermediates which are converted to the compounds of the invention in a manner described herein, functional groups present, such as amino, thiol, carboxyl and hydroxy groups, are optionally protected by conventional protecting groups that are common in preparative organic chemistry. Protected amino, thiol, carboxyl and hydroxy groups are those that can be converted under mild conditions into free amino thiol, carboxyl and hydroxy groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxy group, amino group, etc.), the structure and stability of the molecule of which the substituent is a part and the reaction conditions.

Well-known protecting groups that meet these conditions and their introduction and removal are described, e.g., in McOmie, "Protective Groups in Organic Chemistry", Plenum Press, London, N.Y. (1973); and Greene and Wuts, "Protective Groups in Organic Synthesis", John Wiley and Sons, Inc., NY (1999).

The above-mentioned reactions are carried out according to standard methods, in the presence or absence of diluent, preferably, such as are inert to the reagents and are solvents thereof, of catalysts, condensing or said other agents, respectively and/or inert atmospheres, at low temperatures, room temperature or elevated temperatures, preferably at or near the boiling point of the solvents used, and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers etc.

Preferably, the pharmaceutical compositions are tablets and gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art. Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable compositions for transdermal application include an effective amount of a compound of the invention with carrier. Advantageous carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

The present invention further provides anhydrous pharmaceutical compositions and dosage forms comprising the compounds of the present invention as active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The invention likewise relates to a combination of a compound of formula (I), (I A) or (I B), respectively, or a pharmaceutically acceptable salt thereof with a further active principle.

The combination may be made for example with the following active principles, selected from the group consisting of a:

(i) HMG-Co-A reductase inhibitor or a pharmaceutically acceptable salt thereof, (ii) angiotensin II receptor antagonist or a pharmaceutically acceptable salt thereof, (iii) angiotensin converting enzyme (ACE) Inhibitor or a pharmaceutically acceptable salt thereof, (iv) calcium channel blocker or a pharmaceutically acceptable salt thereof, (v) aldosterone synthase inhibitor or a pharmaceutically acceptable salt thereof, (vi) aldosterone antagonist or a pharmaceutically acceptable salt thereof, (vii) dual angiotensin converting enzyme/neutral endopeptidase (ACE/NEP) inhibitor or a pharmaceutically acceptable salt thereof, (viii) endothelin antagonist or a pharmaceutically acceptable salt thereof, (ix) renin inhibitor or a pharmaceutically acceptable salt thereof, (x) diuretic or a pharmaceutically acceptable salt thereof, and (xi) an ApoA-1 mimic.

An angiotensin 11 receptor antagonist or a pharmaceutically acceptable salt thereof is understood to be an active ingredients which bind to the AT1-receptor subtype of angiotensin II receptor but do not result in activation of the receptor. As a consequence of the inhibition of the AT1 receptor, these antagonists can, for example, be employed as antihypertensives or for treating congestive heart failure.

The class of AT1 receptor antagonists comprises compounds having differing structural features, essentially preferred are the non-peptidic ones. For example, mention may be made of the compounds which are selected from the group consisting of valsartan, losartan, candesartan, eprosartan, irbesartan, saprisartan, tasosartan, telmisartan, the compound with the designation E-1477 of the following formula

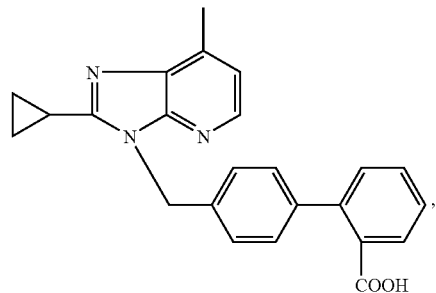

the compound with the designation SC-52458 of the following formula

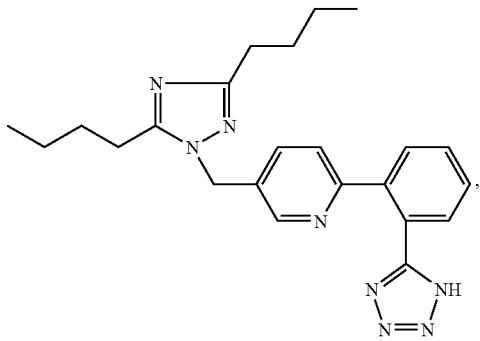

and the compound with the designation ZD-8731 of the following formula

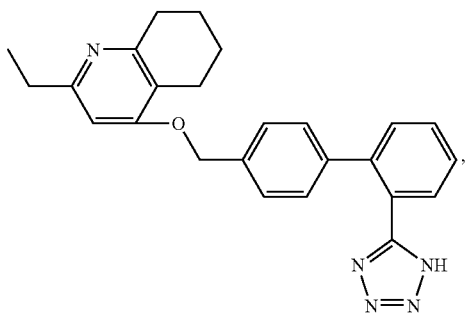

or, in each case, a pharmaceutically acceptable salt thereof.

Preferred AT1-receptor antagonist are those agents which have been marketed, most preferred is valsartan or a pharmaceutically acceptable salt thereof.

HMG-Co-A reductase inhibitors (also called -hydroxymethylglutaryl-co-enzyme-A reductase inhibitors) are understood to be those active agents that may be used to lower the lipid levels including cholesterol in blood.

The class of HMG-Co-A reductase inhibitors comprises compounds having differing structural features. For example, mention may be made of the compounds that are selected from the group consisting of atorvastatin, cerivastatin, compactin, dalvastatin, dihydrocompactin, fluindostatin, fluvastatin, lovastatin, mevastatin, pravastatin, rivastatin, simvastatin, and velostatin, or, in each case, a pharmaceutically acceptable salt thereof.

Preferred HMG-Co-A reductase inhibitors are those agents which have been marketed, most preferred is fluvastatin and pitavastatin or, in each case, a pharmaceutically acceptable salt thereof.

The interruption of the enzymatic degradation of angiotensin I to angiotensin II with so-called ACE-inhibitors (also called angiotensin converting enzyme inhibitors) is a successful variant for the regulation of blood pressure and thus also makes available a therapeutic method for the treatment of congestive heart failure.

The class of ACE inhibitors comprises compounds having differing structural features. For example, mention may be made of the compounds which are selected from the group consisting alacepril, benazepril, benazeprilat, captopril, ceronapril, cilazapril, delapril, enalapril, enaprilat, fosinopril, imidapril, lisinopril, moveltopril, perindopril, quinapril, ramipril, spirapril, temocapril, and trandolapril, or, in each case, a pharmaceutically acceptable salt thereof.

Preferred ACE inhibitors are those agents that have been marketed, most preferred are benazepril and enalapril.

The class of CCBs essentially comprises dihydropyridines (DHPs) and non-DHPs such as diltiazem-type and verapamil-type CCBs.

A CCB useful in said combination is preferably a DHP representative selected from the group consisting of amlodipine, felodipine, ryosidine, isradipine, lacidipine, nicardipine, nifedipine, niguldipine, niludipine, nimodipine, nisoldipine, nitrendipine, and nivaldipine, and is preferably a non-DHP representative selected from the group consisting of flunarizine, prenylamine, diltiazem, fendiline, gallopamil, mibefradil, anipamil, tiapamil and verapamil, and in each case, a pharmaceutically acceptable salt thereof. All these CCBs are therapeutically used, e.g. as anti-hypertensive, anti-angina pectoris or anti-arrhythmic drugs. Preferred CCBs comprise amlodipine, diltiazem, isradipine, nicardipine, nifedipine, nimodipine, nisoldipine, nitrendipine, and verapamil, or, e.g. dependent on the specific CCB, a pharmaceutically acceptable salt thereof. Especially preferred as DHP is amlodipine or a pharmaceutically acceptable salt, especially the besylate, thereof. An especially preferred representative of non-DHPs is verapamil or a pharmaceutically acceptable salt, especially the hydrochloride, thereof.

Aldosterone synthase inhibitor is an enzyme that converts corticosterone to aldosterone to by hydroxylating cortocosterone to form 18-OH-corticosterone and 18-OH-corticosterone to aldosterone. The class of aldosterone synthase inhibitors is known to be applied for the treatment of hypertension and primary aldosteronism comprises both steroidal and non-steroidal aldosterone synthase inhibitors, the later being most preferred.

Preference is given to commercially available aldosterone synthase inhibitors or those aldosterone synthase inhibitors that have been approved by the health authorities.

The class of aldosterone synthase inhibitors comprises compounds having differing structural features. For example, mention may be made of the compounds which are selected from the group consisting of the non-steroidal aromatase inhibitors anastrozole, fadrozole (including the (+)-enantiomer thereof), as well as the steroidal aromatase inhibitor exemestane, or, in each case where applicable, a pharmaceutically acceptable salt thereof.

The most preferred non-steroidal aldosterone synthase inhibitor is the (+)-enantiomer of the hydrochloride of fadrozole (U.S. Pat. Nos. 4,617,307 and 4,889,861) of formula

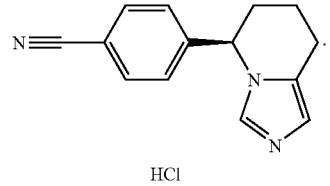

A preferred steroidal aldosterone antagonist is eplerenone of the formula

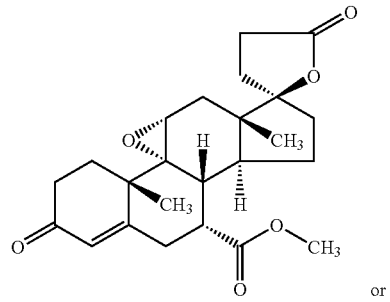

spironolactone.

A preferred dual angiotensin converting enzyme/neutral endopetidase (ACE/NEP) inhibitor is, for example, omapatrilate (cf. EP 629627), fasidotril or fasidotrilate, or, if appropriable, a pharmaceutically acceptable salt thereof.

A preferred endothelin antagonist is, for example, bosentan (cf. EP 526708 A), furthermore, tezosentan (cf. WO 96/19459), or in each case, a pharmaceutically acceptable salt thereof.

A renin inhibitor is, for example, a non-peptidic renin inhibitor such as the compound of formula

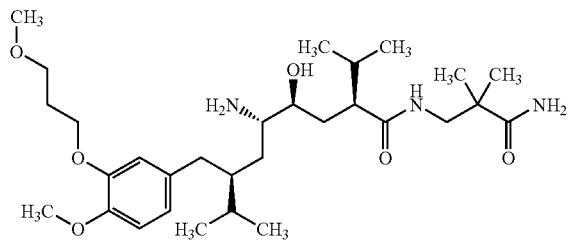

chemically defined as 2(S),4(S),5(S),7(S)-N-(3-amino-2,2-dimethyl-3-oxopropyl)-2,7-di(1-methylethyl)-4-hydroxy-5-amino-8-[4-methoxy-3-(3-methoxy-propoxy)phenyl]-octanamide. This representative is specifically disclosed in EP 678503A. Especially preferred is the hemi-fumarate salt thereof.

A diuretic is, for example, a thiazide derivative selected from the group consisting of chlorothiazide, hydrochlorothiazide, methylclothiazide, and chlorothalidon. The most preferred is hydrochlorothiazide.

An ApoA-I mimic is, for example, D4F peptide, especially of formula D-W-F-K-A-F-Y-D-K-V-A-E-K-F-K-E-A-F Preferably, the jointly therapeutically effective amounts of the active agents according to the combination of the present invention can be administered simultaneously or sequentially in any order, separately or in a fixed combination.

The structure of the active agents identified by generic or tradenames may be taken from the actual edition of the standard compendium "The Merck Index" or from databases, e.g. IMS LifeCycle (e.g. IMS World Publications). The corresponding content thereof is hereby incorporated by reference. Any person skilled in the art is fully enabled to identify the active agents and, based on these references, likewise enabled to manufacture and test the pharmaceutical indications and properties in standard test models, both in vitro and in vivo.

Furthermore, the combinations as described above can be administered to a subject via simultaneous, separate or sequential administration (use). Simultaneous administration (use) can take place in the form of one fixed combination with two or more active ingredients, or by simultaneously administering two or more compounds that are formulated independently. Sequential administration(use) preferably means administration of one (or more) compounds or active ingredients of a combination at one time point, other compounds or active ingredients at a different time point, that is, in a chronically staggered manner, preferably such that the combination shows more efficiency than the single compounds administered independently (especially showing synergism). Separate administration (use) preferably means administration of the compounds or active ingredients of the combination independently of each other at different time points, preferably meaning that two compounds are administered such that no overlap of measurable blood levels of both compounds are present in an overlapping manner (at the same time).

Also combinations of two or more of sequential, separate and simultaneous administrations are possible, preferably such that the combination compound-drugs show a joint therapeutic effect that exceeds the effect found when the combination compound-drugs are used independently at time intervals so large that no mutual effect on their therapeutic efficiency can be found, a synergistic effect being especially preferred.

Additionally, the present invention provides:
a pharmaceutical composition or combination of the present invention for use as a medicament;
the use of a pharmaceutical composition or combination of the present invention for the delay of progression and/or treatment of a disorder or disease mediated by CETP or responsive to the inhibition of CETP.
the use of a pharmaceutical composition or combination of the present invention for the delay of progression and/or treatment of a disorder or disease selected from hyperlipidemia, arteriosclerosis, atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorder, coronary heart disease, coronary artery disease, coronary vascular disease, angina, ischemia, heart ischemia, thrombosis, cardiac infarction such as myocardial infarction, stroke, peripheral vascular disease, reperfusion injury, angioplasty restenosis, hypertension, congestive heart failure, diabetes such as type II diabetes mellitus, diabetic vascular complications, obesity or endotoxemia etc.

The pharmaceutical composition or combination of the present invention can be in unit dosage of about 1-1000 mg of active ingredients for a subject of about 50-70 kg, preferably about 5-500 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, e.g., as a suspension or in aqueous solution. The dosage in vitro may range between about 10-3 molar and 10-9 molar concentrations. A therapeutically effective amount in vivo may range depending on the route of administration, between about 0.1-500 mg/kg, preferably between about 1-100 mg/kg.

The CETP inhibitory effect of the compounds of the present invention can be determined by using the test models or assays known in the art. For example, EP1115695B1 describes both the in vitro and in vivo CETP activity assays, the contents of which are hereby incorporated by reference. In particular, the following assays are used.

(1) CETP In Vitro Assay:
CETP Activity Kit (#RB-RPAK) was purchased from Roar Biochemical, Inc. (New York, N.Y., USA). To each well of a 96-well NBS half-area plate (costar #3686), 1.2 ng/well of the donor solution, 1 µL of the acceptor solution and 5 µL compound solution diluted in 100% DMSO were added in a 38 µL of buffer containing 10 mM Tris, 150 mM NaCl and 2 mM EDTA, pH 7.4. Then, the plate was sealed with Themowell™ Sealers (costar #6524) and followed by a mixing on a plate shaker by MICROPLATE MIXER MPX-96 (IWAKI) at power 3 for 10 sec at room temperature. After 10-min incubation at 37° C., the reaction was started by adding 5 µL of rhCETP solution (Cardiovascular Target, New York, N.Y., USA) and mixed on the plate shaker for 10 sec, then the fluorescence intensity at 0 min was measured by a ARVO SX (PerkinElmerr, USA) at excitation wavelength of 465 nm and emission wavelength of 535 nm. After 120 min-incubation at 37° C., fluorescence intensity was measured again. The inhibition of rhCETP activity by a compound was calculated by the following calculation. Inhibition %={1−(F120−F0)/(f120−f0)}×100 F: measured fluorescence intensity with compound at 0 or 120 min. f: measured fluorescence intensity of without compound at 0 or 120 min.

The IC50 values are determined from the dose-effect curve by Origin software. IC50 values, especially from about 0.1 nM to about 50 µM, are determined for the compounds of the present invention or a pharmaceutically acceptable salt thereof.

(2) Effects on Plasma HDL Levels in Hamster:

Effects of compounds on HDL-cholesterol level in hamsters are investigated by the method reported previously with some modifications (Eur, J. Pharmacol, 466 (2003) 147-154). In brief, male Syrian hamsters (10-11 week-old age, SLC, Shizuoka, Japan) are fed a high cholesterol diet for two weeks. Then, the animals are dosed singly with the compound suspended with carboxylmethyl cellulose solution. HDL-cholesterol levels are measured by using commercially available kit (Vako Pure Chemical, Japan) after the precipitation of apolipoprotein B (apoB)-containing lipoproteins with 13% polyethylene glycol 6000.

(3) Preparation of Human pro-Apolipoprotein AI (pro-apoAI)

The cDNA of human pro-apoAI (NCBI accession number: NM_000039) is cloned from human liver Quick-Clone™ cDNA (Clontech, CA) and inserted to a pET28a vector (Novagen, Germany) for bacterial expression. Expressed protein as a fusion protein with 6×His-tag at N-terminus in BL-21 Gold (DE3) (Strategene, CA) is purified using HiTrap Chelating (GE Healthcare, CT).

(4) Preparation of Donor Microemulsion

Pro-apoAI containing microemulsion as a donor particle is prepared following previous reports (J. Biol. Chem., 280: 14918-22). Glyceryl trioleate (62.5 ng, Sigma, Mo.), 3-sn-phosphatidylcholine (583 ng, Wako Pure Chemical Industries, Japan), and cholesteryl BODIPY® FL C12 (250 ng, Invitrogen, CA) are dissolved in 1 mL of chloroform. The solution is evaporated, then residual solvent is removed in vacuum for more than 1 hr. The dried lipid mixture is dissolved in 500 µL of the assay buffer (50 mM Tris-HCl (pH7.4) containing 150 mM NaCl and 2 mM EDTA) and sonicated at 50° C. with a microtip (MICROSON™ ULTRASONIC CELL DISRUPTOR, Misonix, Farmingdale, N.Y.) at output power 006 for 2 min. After sonication, the solution is cooled to 40° C., added to 100 µg of human pro-apoAI, and sonicated at output power 004 for 5 min at 40° C. The solution, BODIPY-CE microemulsion as a donor molecule is stored at 4° C. after filtration through a 0.45 µm PVDF filter.

(5) In Vitro CETP Activity Assay in Human Plasma

Human EDTA plasma samples from healthy men are purchased from New Drug Development Research Center, Inc. Donor solution is prepared by a dilution of donor microemulsion with assay buffer. Human plasma (50 µL), assay buffer (35 µL) and test compound dissolved in dimethylsulfoxide (1 µL) are added to each well of 96 well half area black flat bottom plate. The reaction is started by the addition of donor solution (14 µL) into each well. Fluorescence intensities are measured every 30 min at 37° C. with excitation wave length of 485 nm and emission wavelength of 535 nm. The CETP activity (FI/min) is defined as the changes of fluorescence intensity from 30 to 90 min. The IC50 value is obtained by the logistic equation (Y=Bottom+(Top−Bottom)/(1+(x/IC50)^Hill slope) using Origin software, version 7.5 SR3. The compounds of formula I exhibit inhibitory activity with an IC50 value in the range from approximately from 0.001 to 100 µM, especially from 0.01 to 10 µM.

The compounds of the present invention or a pharmaceutically acceptable salt thereof have superior CETP inhibitory activity in mammals (e.g., human, monkey, bovine, horse, dog, cat, rabbit, rat, mouse and the like), and can be used as CETP activity inhibitors. In addition, utilizing the superior CETP inhibitory activity of a compound of the present invention or a pharmaceutically acceptable salt thereof, the compounds of the present invention are useful as pharmaceutical agents effective for the prophylaxis or treatment of or delay progression to overt to diseases in which CETP is involved (e.g., hyperlipidemia, arteriosclerosis, atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorder, coronary heart disease, coronary artery disease, coronary vascular disease, angina, ischemia, heart ischemia, thrombosis, cardiac infarction such as myocardial infarction, stroke, peripheral vascular disease, reperfusion injury, angioplasty restenosis, hypertension, congestive heart failure, diabetes such as type II diabetes mellitus, diabetic vascular complications, obesity or endotoxemia etc.), particularly as prophylactic or therapeutic agents for hyperlipidemia or arteriosclerotic diseases.

TABLE 1

Inhibitory Activity of Compounds

| Compound | IC50 (nM) |
| --- | --- |
| Example 1-2 | 142 |
| Example 1-5 | 135 |
| Example 1-8 | 69 |
| Example 1-11 | 63 |
| Example 1-17 | 86 |
| Example 1-19 | 98 |
| Example 1-20 | 91 |
| Example 1-22 | 99 |
| Example 1-27 | 152 |
| Example 4 | 68 |

Abbreviations
Ac: Acetyl
aq: aqueous
Ar: aromatic
BBN: borabicyclo[3.3.1]nonane
dba: dibenzylideneacetone
Bn: benzyl
Boc: tert-butoxycarbonyl
CAN: ceric ammonium nitrate
DDQ: 2,3-dichloro-5,6-dicyano-p-benzoquinone
DEAD: diethyl azodicarboxylate
DIPEA: N,N-diisopropylethylamine
DMAP: N,N-dimethylaminopyridine
DME: dimethoxyethane
DMME: dimethoxymethane
DMMIM: 1-butyl-3-methylimidazolium
DMF: N,N-dimethylformamide DMSO: dimethyl sulfoxide
dppf: 1,1-bis(diphenylphosphino)ferrocene
EDTA: ethylenediaminetetraacetic acid
ESI: electrospray ionization
Et: ethyl
EtOAc: ethyl acetate
h: hours
HCl: hydrogen chloride
HPLC: high pressure liquid chromatography
IPA: 2-propanol
iPr: isopropyl
IR: infrared
KHMDS: potassium hexamethyldisilamide
LC: liquid chromatography
LDA: lithium diisopropylamide
LHMDS: lithium hexamethyldisilamide
Me: methyl
min: minutes
MS: mass spectrometry
Ms: mesyl
NBS: N-bromosuccinimide
NMR: nuclear magnetic resonance
Ph: phenyl
PMB: p-methoxybenzyl
RP: reversed phase
RT: room temperature
s-Bu: sec-butyl
Sia: siamyl
SFC: supercritical fluid chromatography
TBAI: tetrabutylammonium iodide
Tf: triflate
TFA: trifluoroacetic acid
THF: tetrahydrofuran
TLC: thin layer chromatography
Ts: tosyl
tBu: tert-butyl
tol: tolyl

EXAMPLES

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art. The compounds in the following examples have been found to have IC50 values in the range of about 0.1 nM to about 10,000 nM for CETP.

The conditions for measuring the retention times are as follows:

Condition A (HPLC)
Column: ACQUITY UPLCTM BEH C18 1.7 um, 50×2.1 mm.
Flow rate: 0.5 ml 1 min
Mobile phase: A) TFA/water (0.1/100, v/v), B) TFA/acetonitrile (0.1/100, v/v)
Gradient: 5% B in 0.5 min, then linear gradient from 5% B to 100% B in 1.5 min then 100% B in 1 min
Detection: UV at 215 nm
Condition B (HPLC)
Column: ACQUITY UPLCTM BEH C18 1.7 um, 50×2.1 mm.
Flow rate: 0.5 ml/min
Mobile phase: A) TFA/water (0.1/100, v/v), B) TFA/acetonitrile (0.1/100, v/v)
Gradient: 5% B in 0.5 min, then linear gradient from 5% B to 100% B in 5.0 min then 100% B in 1.5 min
Detection: UV at 215 nm
Condition C (HPLC)
Column: CombiScreen ODS-AM, 50×4.6 mm.
Flow rate: 2.0 ml/min
Mobile phase: A) TFA/water (0.1/100, v/v), B) TFA/acetonitrile (0.1/100, v/v)
Gradient: linear gradient from 5% B to 100% B in 5 min then 100% B in 2 min
Detection: UV at 215 nm Examples Example 1

Synthesis of (4-{cis-2-benzyl-4-[(3,5-bis(trifluoromethyl)benzyl)-(5-morpholin-4-yl-pyrimidin-2-yl)-amino]-6-ethylpiperidine-1-carbonyl}-cyclohexyl)-acetic acid

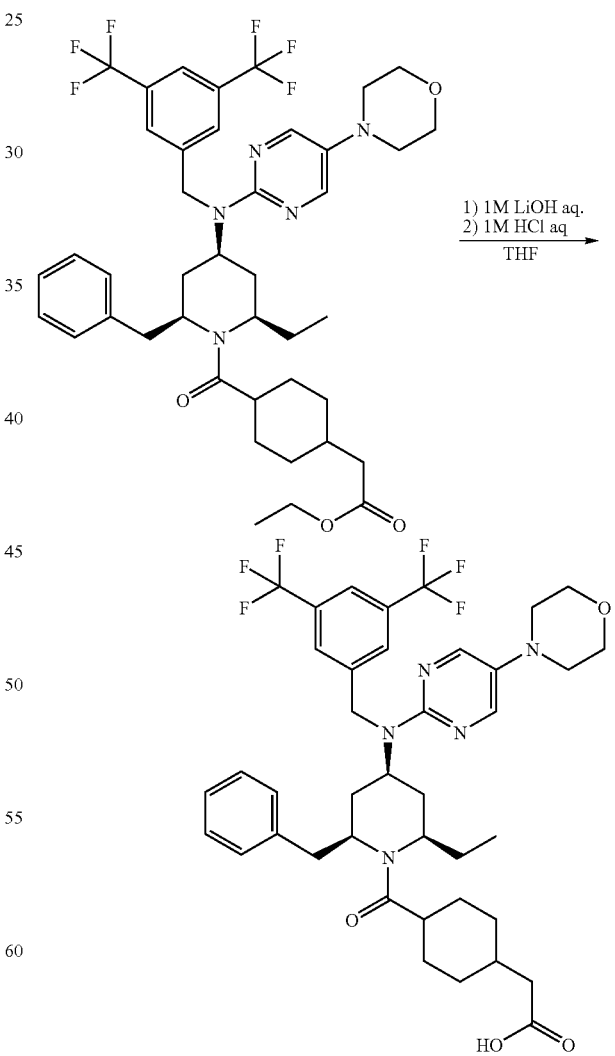

To a solution of (4-{cis-2-benzyl-4-[(3,5-bis(trifluoromethyl)benzyl)-(5-morpholin-4-yl-pyrimidin-2-yl)-amino]-6- ethylpiperidine-1-carbonyl}-cyclohexyl)-acetic acid ethyl ester (41 mg, 0.0511 mmol) in THF (1.79 ml) and H2O (0.51 ml), aqueous 1M LiOH (255 uL) is added at room temperature. The mixture is stirred at room temperature for 18 hours. To the mixture, aqueous 1M HCl (255 uL) and H2O is added. The solution is extracted with dichloromethane, and the organic layer is concentrated under reduced pressure. The obtained residue is purified by reverse-phase HPLC to give (4-{cis-2-benzyl-4-[(3,5-bis(trifluoromethyl)benzyl)-(5-morpholin-4-yl-pyrimidin-2-yl)-amino]-6-ethyl-piperidine-1-carbonyl}-cyclohexyl)-acetic acid (24.1 mg, 60.8%); ESI-MS m/z: 776 [M+1]+, Retention time 4.56 min (condition B).

The following compounds are prepared following the procedure of Example 1

| No | Product | ESI-MS m/z [M + 1]+ | Retention time (min) | Starting Material |
|---|---|---|---|---|
| 1 | 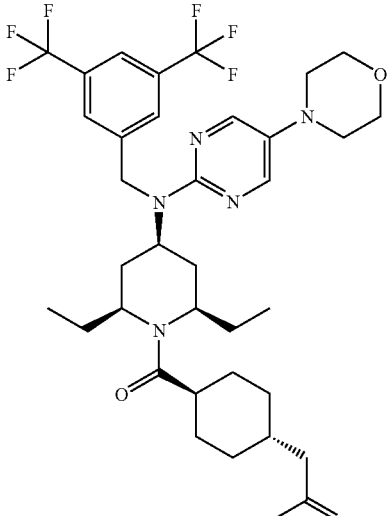 | 714 | 2.17 (condition A) | 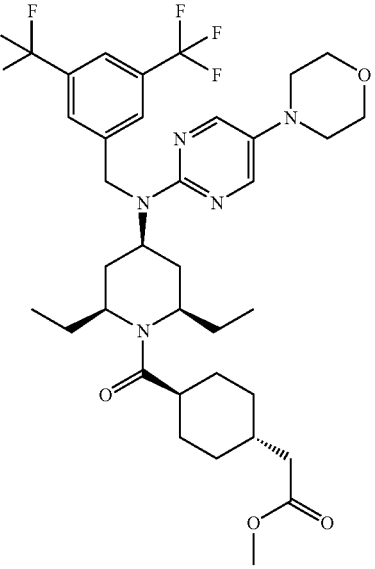 |
| 2 | 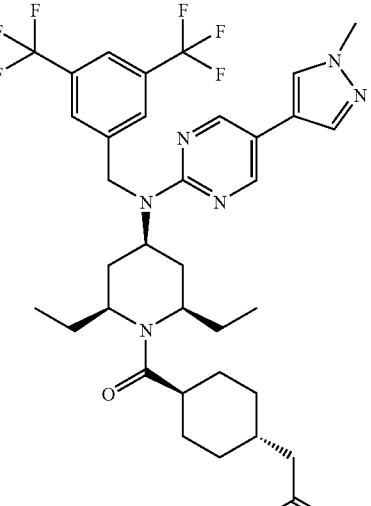 | 709 | 2.16 (condition A) | 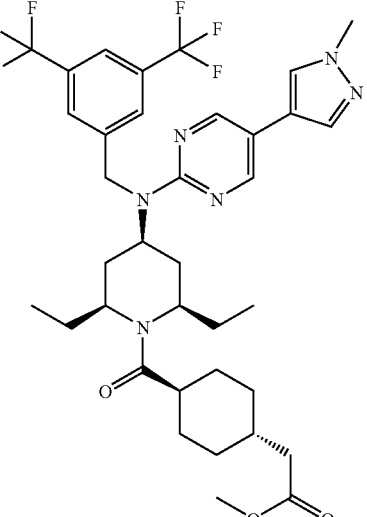 |

-continued
| No | Product | ESI-MS m/z [M + 1]+ | Retention time (min) | Starting Material |
|---|---|---|---|---|
| 3 | 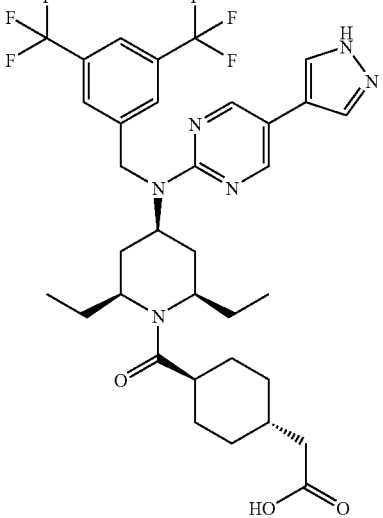 | 695 | 2.10 (condition A) | 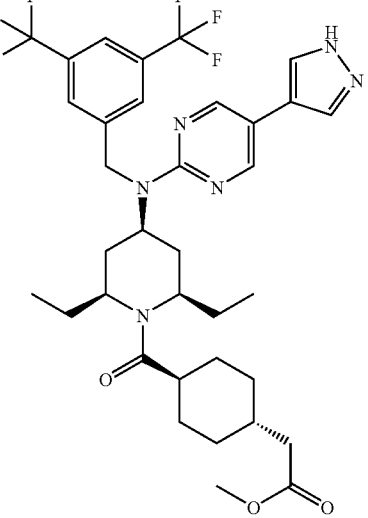 |
| 4 | 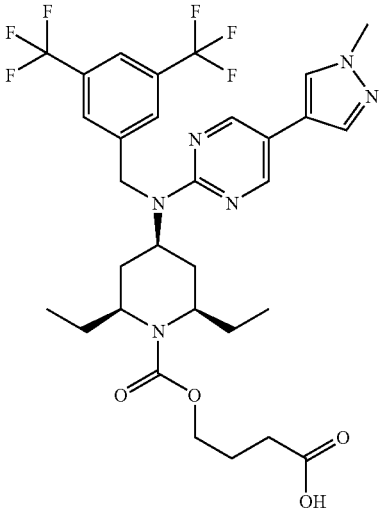 | 671 | 2.15 (condition A) | 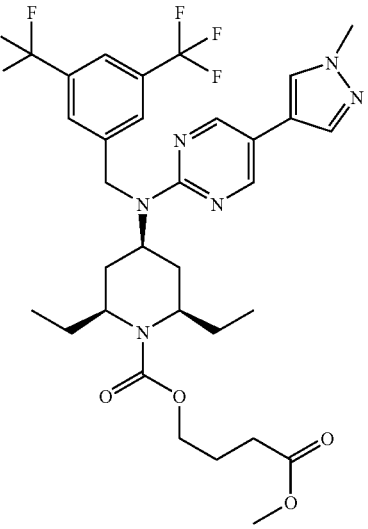 |
| 5 | 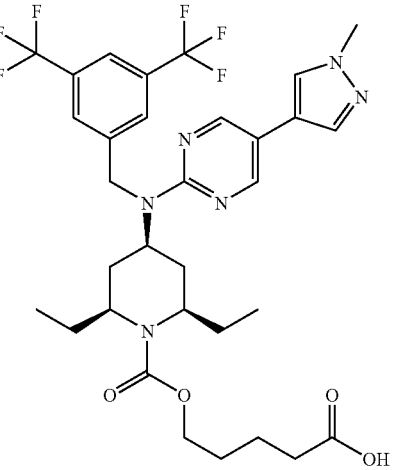 | 685 | 2.17 (condition A) | 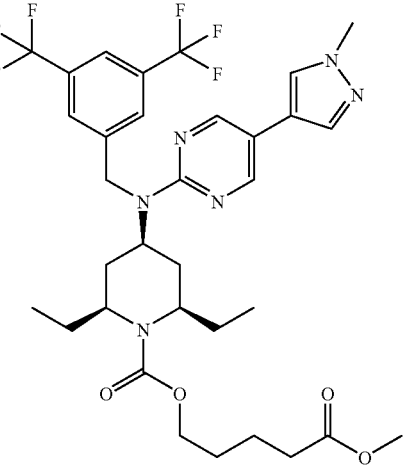 |

-continued
| No | Product | ESI-MS m/z [M + 1]+ | Retention time (min) | Starting Material |
|---|---|---|---|---|
| 6 | 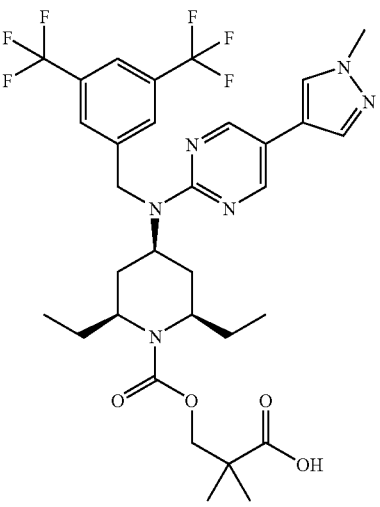 | 685 | 2.19 (condition A) | 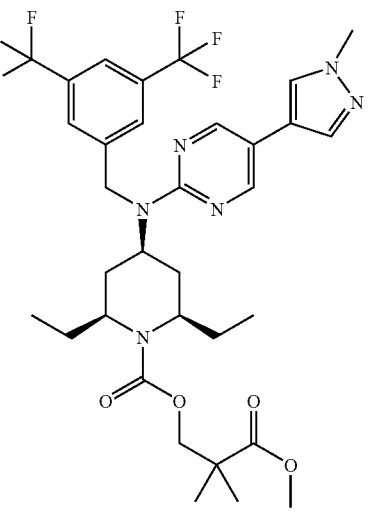 |
| 7 | 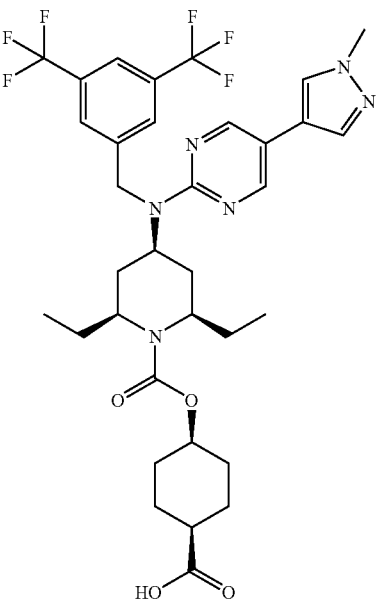 | 711 | 4.38 (condition B) | 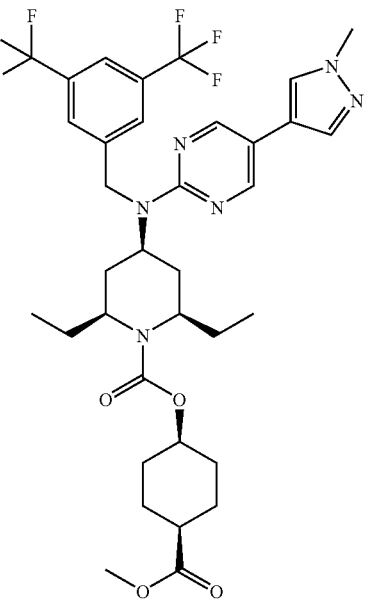 |

| No | Product | ESI-MS m/z [M + 1]+ | Retention time (min) | Starting Material |
|---|---|---|---|---|
| 8 | 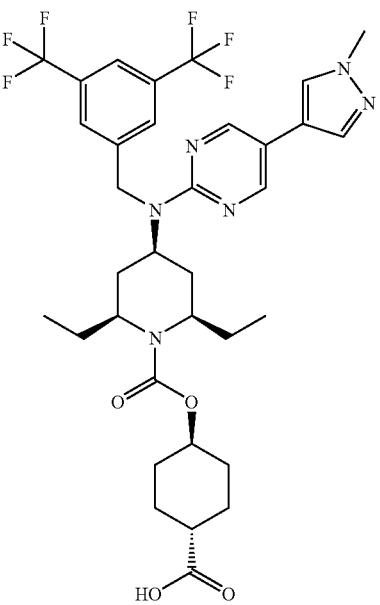 | 711 | 4.56 (condition B) | 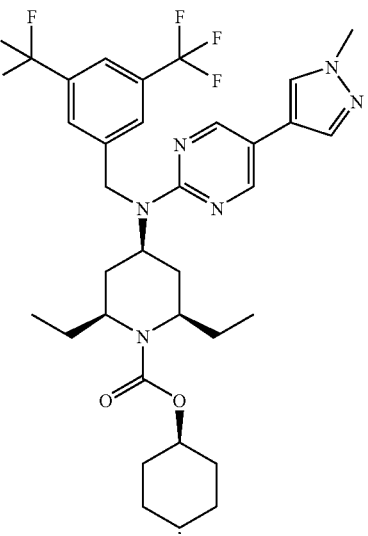 Use 1M NaOH instead |
| 9 | 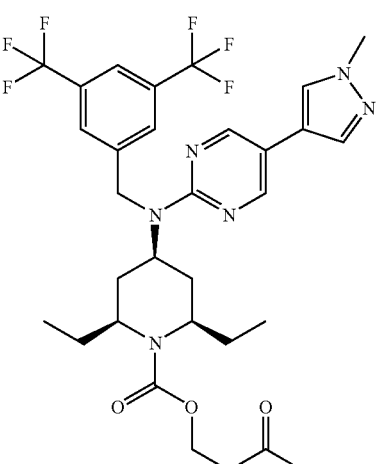 | 657 | 2.11 (condition A) | 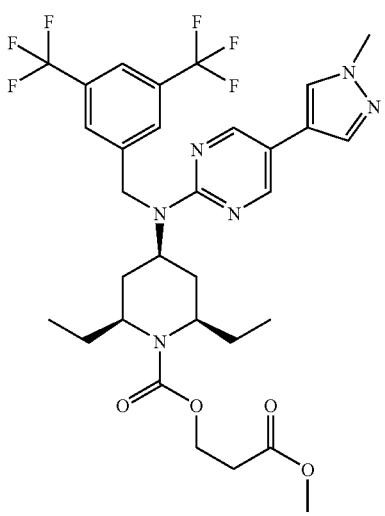 |

-continued
| No | Product | ESI-MS m/z [M + 1]+ | Retention time (min) | Starting Material |
|---|---|---|---|---|
| 10 | 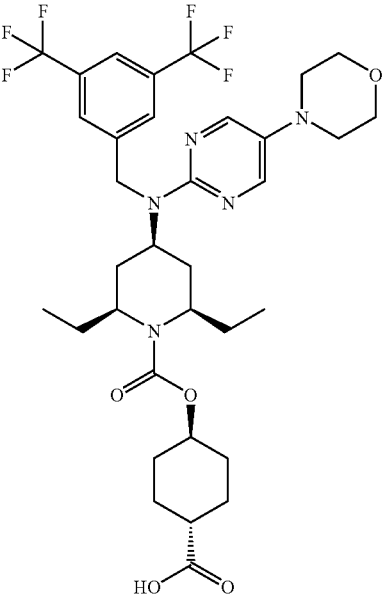 | 716 | 2.23 (condition A) | 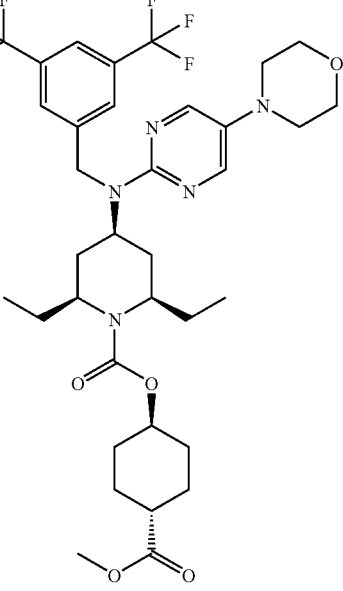 |
| 11 | 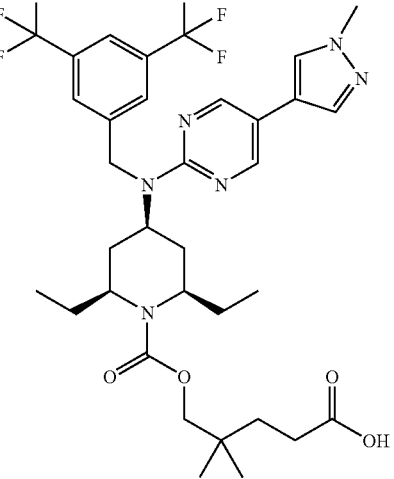 | 713 | 2.23 (condition A) | 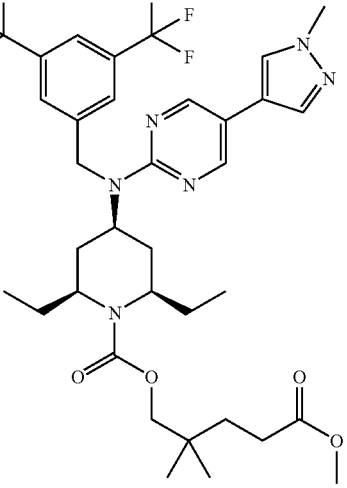 |

-continued

| No | Product | ESI-MS m/z [M + 1]+ | Retention time (min) | Starting Material |
|---|---|---|---|---|
| 12 | | 698 | 1.90 (condition A) | Use 1M NaOH instead of 1M LiOH |
| 13 | | 716 | 4.14 (condition B) | |

-continued
| No | Product | ESI-MS m/z [M + 1]+ | Retention time (min) | Starting Material |
|---|---|---|---|---|
| 14 | 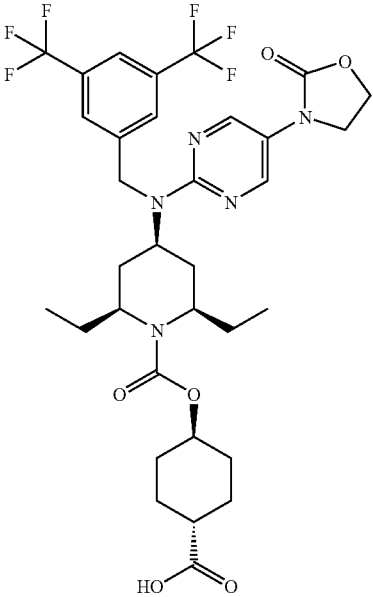 | 716 | 2.19 (condition A) | 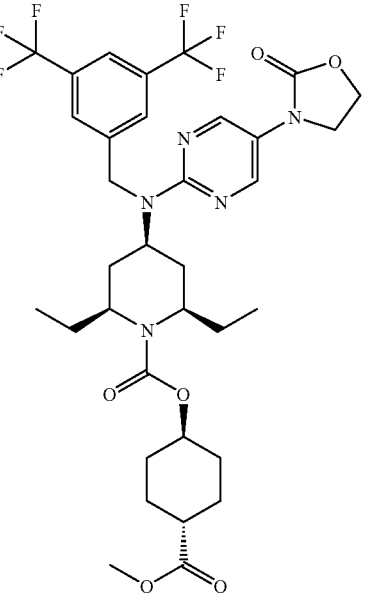<br>Use 1M NaOH instead of 1M LiOH |
| 15 | 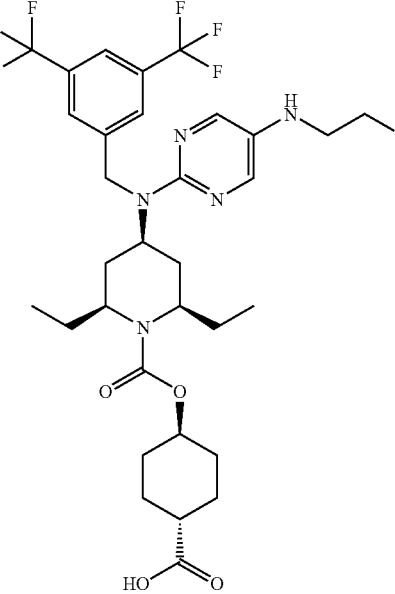 | 690 | 1.94 (condition A) | 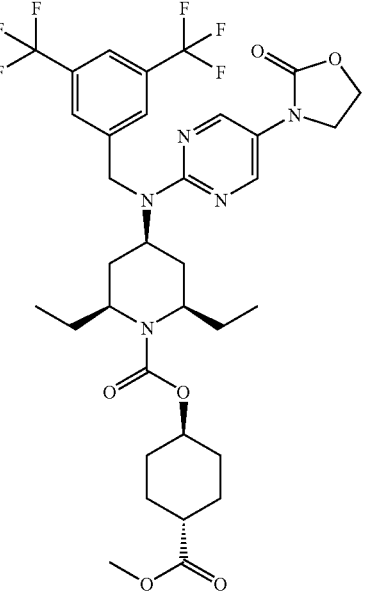<br>Use 1M NaOH instead of 1M LiOH |

| No | Product | ESI-MS m/z [M + 1]+ | Retention time (min) | Starting Material |
|----|---------|---------------------|----------------------|-------------------|
| 16 | 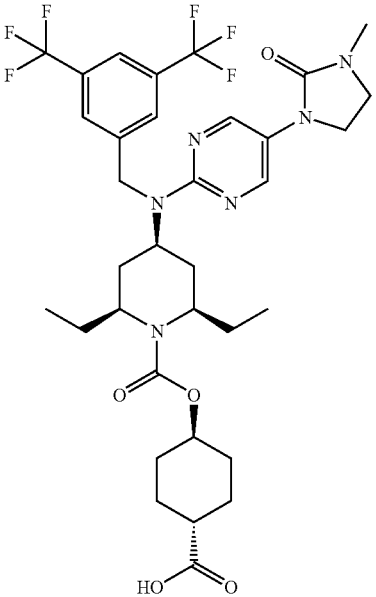 | 729 | 2.21 (condition A) | 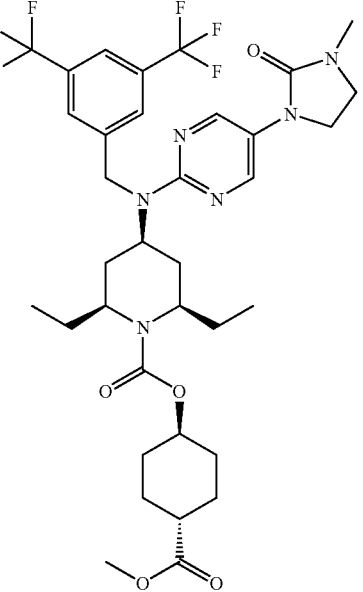<br>Use 1M NaOH instead of 1M LiOH |
| 17 | 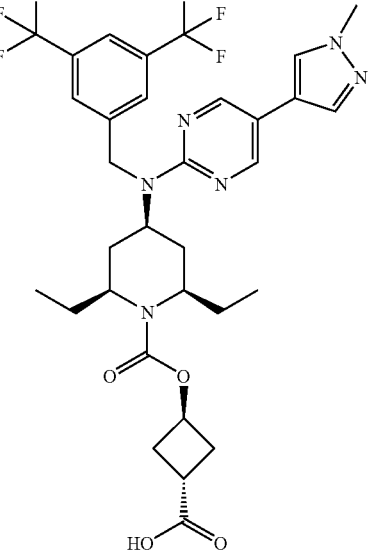 | 683 | 2.18 (condition A) | 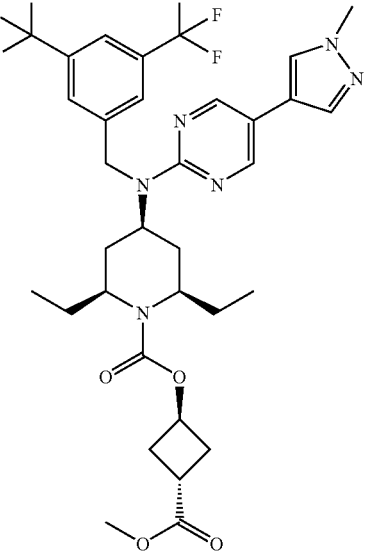 |

-continued

| No | Product | ESI-MS m/z [M + 1]+ | Retention time (min) | Starting Material |
|----|---------|---------------------|----------------------|-------------------|
| 18 | | 699 | 2.18 (condition A) | |
| 19 | | 683 | 2.17 (condition A) | Use 1M NaOH instead of 1M LiOH |

-continued
| No | Product | ESI-MS m/z [M + 1]+ | Retention time (min) | Starting Material |
|---|---|---|---|---|
| 20 | 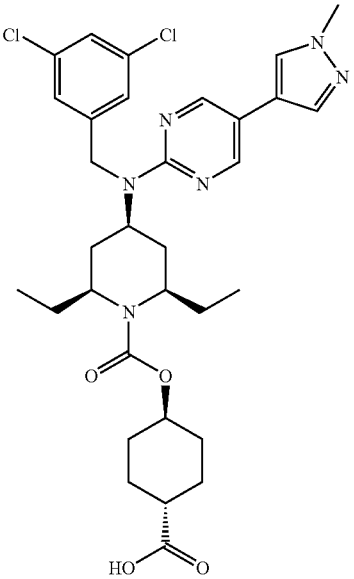 | 643 | 4.72 (condition B) | 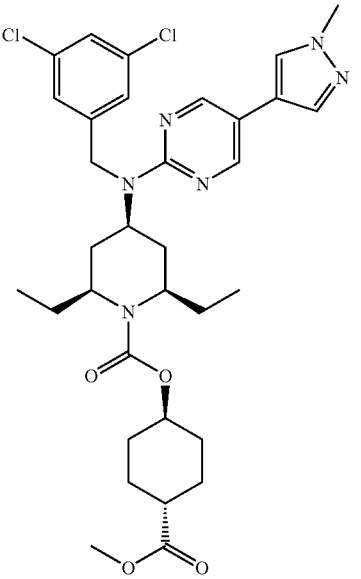 |
| 21 | 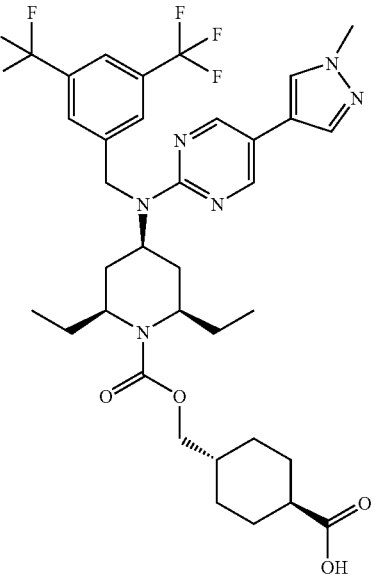 | 725 | 2.37 (condition A) | 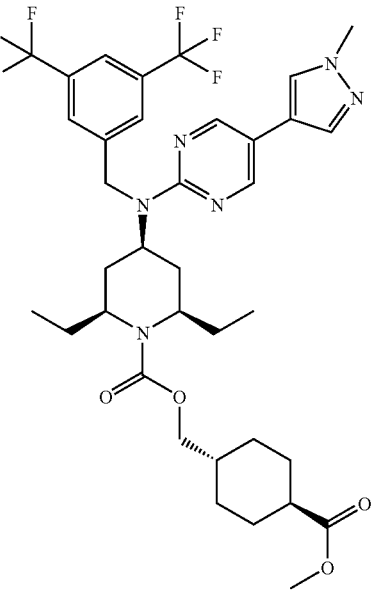 |

-continued

| No | Product | ESI-MS m/z [M + 1]+ | Retention time (min) | Starting Material |
|---|---|---|---|---|
| 22 | (structure) | 661 | 4.42 (condition B) | (structure) |
| 23 | (structure) | 711 | 2.30 (condition A) | (structure) |

-continued
| No | Product | ESI-MS m/z [M + 1]+ | Retention time (min) | Starting Material |
|----|---------|---------------------|----------------------|-------------------|
| 24 | 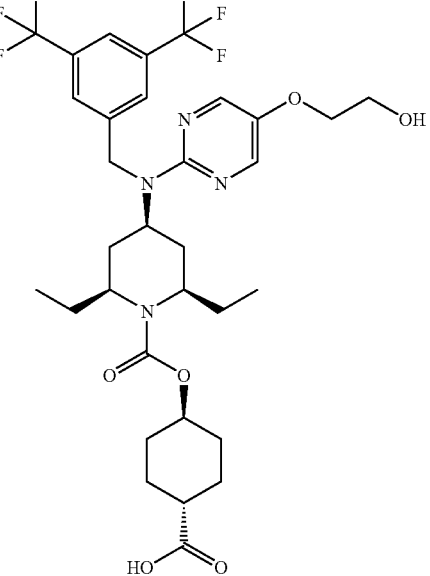 | 691 | 2.34 (condition A) | 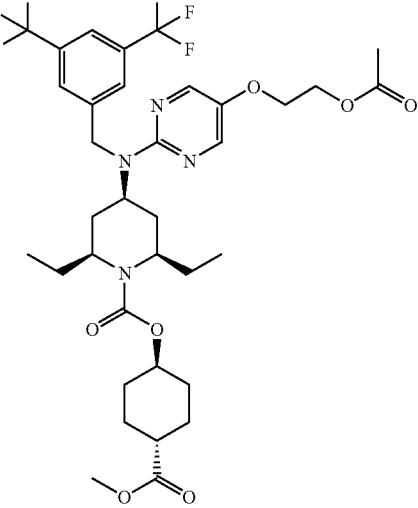 |
| 25 | 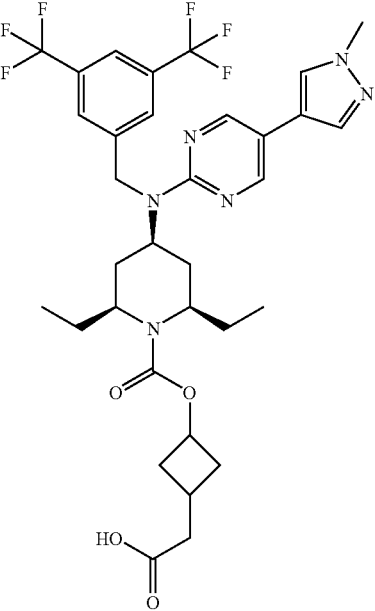 | 697 | 2.23 (condition A) | 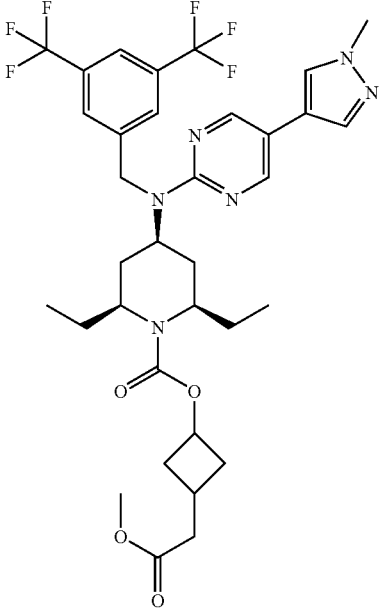 |

-continued
| No | Product | ESI-MS m/z [M + 1]+ | Retention time (min) | Starting Material |
|----|---------|---------------------|----------------------|-------------------|
| 26 | 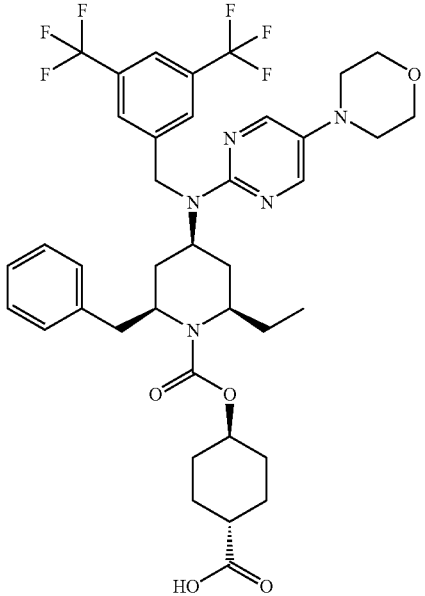 | 778 | 2.33 (condition A) | 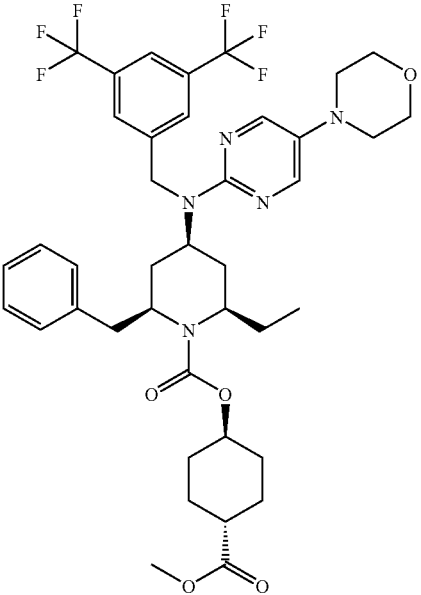 |
| 27 | 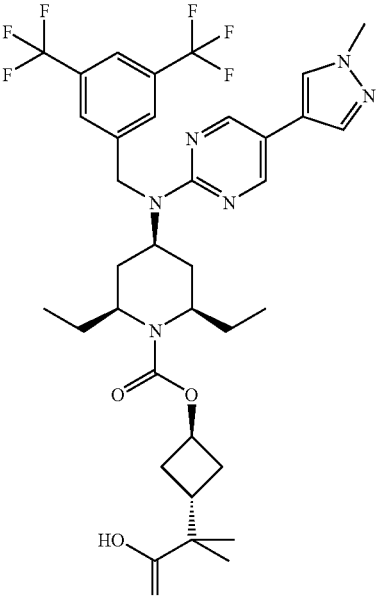 | 725 | 2.35 (condition A) | 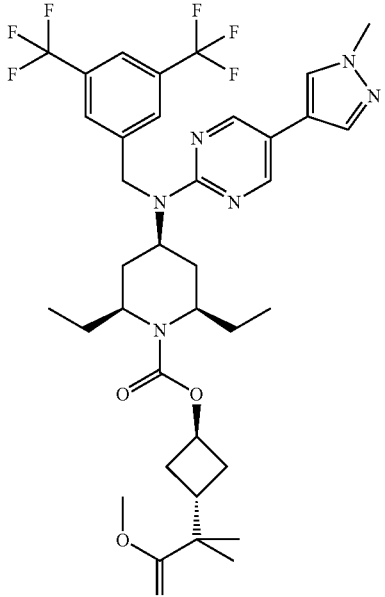 |

-continued

| No | Product | ESI-MS m/z [M + 1]+ | Retention time (min) | Starting Material |
|---|---|---|---|---|
| 28 | (structure: 5-bromopyrimidine with 3,5-bis(trifluoromethyl)benzyl group, 2,6-diethylpiperidine, and trans-4-hydroxycyclohexanecarboxylic acid carbamate) | 709 | 2.54 (condition A) | (structure: same as product but with methyl ester instead of carboxylic acid) |

| No. | 1H NMR |
|---|---|
| 2 | 1H NMR (400 MHz, CHLOROFORM-d) δ ppm 0.79-0.95 (m, 6 H) 0.99-1.17 (m, 2 H) 1.36-1.49 (m, 1 H) 1.64-1.98 (m, 12 H) 2.08-2.31 (m, 4 H) 2.41-2.52 (m, 1 H) 3.89-3.96 (m, 1 H) 4.01 (s, 3 H) 4.50-4.62 (m, 1 H) 4.64-4.76 (m, 1 H) 4.89 (d, J=3.28 Hz, 2 H) 7.60 (s, 1 H) 7.70 (s, 2 H) 7.77 (s, 2 H) 8.47 (s, 2 H) |
| 3 | 1H NMR (400 MHz, CHLOROFORM-d) δ ppm 0.80-0.94 (m, 6 H) 1.00-1.15 (m, 2 H) 1.37-1.49 (m, 1 H) 1.57-2.00 (m, 13 H) 2.07-2.35 (m, 4 H) 2.41-2.53 (m, 1 H) 3.89-4.00 (m, 1 H) 4.52-4.63 (m, 1 H) 4.68-4.79 (m, 1 H) 4.90 (s, 2 H) 7.70 (s, 2 H) 7.77 (s, 1 H) 7.96 (s, 2 H) 8.51 (s, 2 H) |
| 4 | 1H NMR (400 MHz, CHLOROFORM-d) δ ppm 0.85 (t, J=7.33 Hz, 6 H) 1.30-1.51 (m, 6 H) 1.64-1.78 (m, 2 H) 2.03-2.18 (m, 2 H) 2.22-2.32 (m, 2 H) 2.47-2.54 (m, 2 H) 3.94 (s, 3 H) 4.25-4.35 (m, 2 H) 4.58-4.69 (m, 1 H) 4.88 (br. s., 2 H) 7.55 (s, 1 H) 7.66 (s, 1 H) 7.70 (s, 2 H) 7.76 (s, 1 H) 8.43 (s, 2 H) |
| 5 | 1H NMR (400 MHz, CHLOROFORM-d) δ ppm 0.86 (t, J=7.33 Hz, 6 H) 1.40-1.51 (m, 4 H) 1.68-1.90 (m, 6 H) 2.13-2.24 (m, 2 H) 2.42-2.48 (m, 2 H) 3.94 (s, 3 H) 4.13-4.23 (m, 2 H) 4.24-4.35 (m, 2 H) 4.63-4.75 (m, 1 H) 4.87 (s, 2 H) 7.56 (s, 1 H) 7.67 (s, 1 H) 7.69 (s, 2 H) 7.75 (s, 1 H) 8.55 (s, 2 H) |
| 6 | 1H NMR (400 MHz, CHLOROFORM-d) δ ppm 0.86 (t, J=7.33 Hz, 6 H) 1.30 (s, 6 H) 1.39-1.54 (m, 4 H) 1.67-1.80 (m, 2 H) 2.12-2.21 (m, 2 H) 3.95 (s, 3 H) 4.17-4.36 (m, 4 H) 4.54-4.66 (m, 1 H) 4.86 (s, 2 H) 7.56 (s, 1 H) 7.67 (s, 1 H) 7.69 (s, 2 H) 7.75 (s, 1 H) 8.46 (s, 2 H) |
| 7 | 1H NMR (400 MHz, CHLOROFORM-d) δ ppm 0.86 (t, J=7.45 Hz, 6 H) 1.41-1.58 (m, 4 H) 1.60-1.70 (m, 2 H) 1.78-1.88 (m, 6 H) 1.89-1.97 (m, 2 H) 2.11-2.21 (m, 2 H) 2.40-2.50 (m, 1 H) 3.95 (s, 3 H) 4.13-4.22 (m, 2 H) 4.76-4.84 (m, 1 H) 4.86 (s, 2 H) 4.94 (m, 1 H) 7.53 (s, 1 H) 7.67 (s, 1 H) 7.71 (s, 2 H) 7.75 (s, 1 H) 8.43 (s, 2 H) |
| 8 | 1H NMR (400 MHz, CHLOROFORM-d) δ ppm 0.85 (t, J=7.30 Hz, 6 H) 1.36-1.70 (m, 7 H) 1.75-1.85 (m, 3 H) 2.03-2.20 (m, 6 H) 2.31-2.41 (m, 1 H) 3.95 (s, 3 H) 4.11-4.22 (m, 2 H) 4.61-4.71 (m, 1 H) 4.76-4.88 (m, 1 H) 4.86 (s, 2 H) 7.53 (s, 1 H) 7.66 (s, 1 H) 7.70 (s, 2 H) 7.75 (s, 1 H) 8.43 (s, 2 H) |
| 9 | 1H NMR (400 MHz, CHLOROFORM-d) δ ppm 0.86 (t, J=7.33 Hz, 6 H) 1.40-1.54 (m, 4 H) 1.68-1.81 (m, 2 H) 2.13-2.21 (m, 2 H) 2.75 (t, J=6.06 Hz, 2 H) 3.97 (s, 3 H) 4.21-4.31 (m, 2 H) 4.42-4.48 (m, 2 H) 4.59-4.69 (m, 1 H) 4.87 (s, 2 H) 7.57 (s, 1 H) 7.69 (s, 2 H) 7.70 (s, 1 H) 7.76 (s, 1 H) 8.47 (s, 2 H) |
| 10 | 1H NMR (400 MHz, CHLOROFORM-d) δ ppm 0.84 (t, J=7.45 Hz, 6 H) 1.35-1.53 (m, 6 H) 1.55-1.67 (m, 2 H) 1.74-1.83 (m, 2 H) 2.03-2.18 (m, 6 H) 2.30-2.40 (m, 1 H) 2.99-3.05 (m, 4 H) 3.83-3.87 (m, 4 H) 4.10-4.19 (m, 2 H) 4.62-4.76 (m, 2 H) 4.79 (s, 2 H) 7.69 (s, 2 H) 7.73 (s, 1 H) 8.09 (s, 2 H) |

-continued

| No. | 1H NMR |
|---|---|
| 12 | 1H NMR (400 MHz, CHLOROFORM-d) δ ppm 0.85 (t, J=7.33 Hz, 6 H) 1.41-1.61 (m, 4 H) 1.75-1.83 (m, 2 H) 2.12-2.21 (m, 2 H) 3.67-3.85 (m, 4 H) 3.94 (s, 3 H) 4.07-4.17 (m, 2 H) 4.52-4.65 (m, 2 H) 4.72-4.83 (m, 1 H) 4.86 (s, 2 H) 5.17-5.27 (m, 1 H) 7.54 (s, 1 H) 7.66 (s, 1 H) 7.70 (s, 2 H) 7.75 (s, 1 H) 8.44 (s, 2 H) |
| 13 | 1H NMR (400 MHz, CHLOROFORM-d) δ ppm 0.84 (t, J=7.30 Hz, 6 H) 1.38-1.48 (m, 6 H) 1.74-1.84 (m, 3 H) 2.05-2.24 (m, 6 H) 2.32-2.41 (m, 1 H) 3.19-3.29 (m, 2 H) 3.40-3.50 (m, 2 H) 4.10-4.18 (m, 2 H) 4.59-4.72 (m, 3 H) 4.76 (s, 2 H) 7.68-7.75 (m, 3 H) 7.86 (s, 2 H) |
| 14 | 1H NMR (400 MHz, CHLOROFORM-d) δ ppm 0.85 (t, J=7.33 Hz, 6 H) 1.35-1.48 (m, 3 H) 1.49-1.68 (m, 5 H) 1.73-1.85 (m, 2 H) 2.03-2.18 (m, 6 H) 2.30-2.43 (m, 1 H) 4.00 dd, 2 H) 4.10-4.19 (m, 2 H) 4.53 (dd, 2 H) 4.62-4.78 (m, 2 H) 4.83 (s, 2 H) 7.68 (s, 2 H) 7.75 (s, 1 H) 8.51 (s, 2 H) |
| 15 | 1H NMR (400 MHz, CHLOROFORM-d) δ ppm 0.84 (t, J=7.45 Hz, 6 H) 1.36-1.69 (m, 7 H) 1.73-1.82 (m, 2 H) 2.02-2.18 (m, 7 H) 2.30-2.40 (m, 1 H) 3.23 (dd, 2 H) 3.84 (dd, 2 H) 4.10-4.20 (m, 2 H) 4.61-4.74 (m, 2 H) 4.76 (s, 2 H) 7.69 (s, 2 H) 7.72 (s, 1 H) 7.94 (s, 2 H) |
| 16 | 1H NMR (400 MHz, CHLOROFORM-d) δ ppm 0.84 (t, J=7.45 Hz, 6 H) 1.38-1.68 (m, 8 H) 1.72-1.87 (m, 2 H) 2.01-2.18 (m, 6 H) 2.28-2.41 (m, 1 H) 2.89 (s, 3 H) 3.50 (dd, 2 H) 3.74 (dd, 2 H) 4.08-4.18 (m, 2 H) 4.62-4.78 (m, 2 H) 4.82 (s, 2 H) 7.69 (s, 2 H) 7.73 (s, 1 H) 8.52 (s, 2 H) |
| 17 | 1H NMR (400 MHz, CHLOROFORM-d) δ ppm 0.86 (t, J=7.33 Hz, 6 H) 1.40-1.61 (m, 4 H) 1.74-1.84 (m, 2 H) 2.11-2.22 (m, 2 H) 2.33-2.46 (m, 2 H) 2.67-2.78 (m, 2 H) 3.09-3.19 (m, 1 H) 3.96 (s, 3 H) 4.09-4.23 (m, 2 H) 4.74-4.84 (m, 1 H) 4.87 (s, 2 H) 5.16-5.24 (m, 1 H) 7.54 (s, 1 H) 7.67 (s, 1 H) 7.71 (s, 2 H) 7.75 (s, 1 H) 8.44 (s, 2 H) |
| 18 | 1H NMR (400 MHz, CHLOROFORM-d) δ ppm 0.74 (t, J=7.05 Hz, 3 H) 1.20-1.54 (m, 9 H) 1.62-1.76 (m, 2 H) 1.85-2.20 (m, 7 H) 4.04-4.17 (m, 2 H) 4.42-4.58 (m, 1 H) 4.73-4.86 (m, 1 H) 4.91 (br. s., 2 H) 7.67 (s, 2 H) 7.73 (s, 1 H) 8.63 (br. s., 2 H) 9.14 (s, 1 H) |
| 19 | 1H NMR (400 MHz, CHLOROFORM-d) δ ppm 1.28 (d, J=6.82 Hz, 6 H) 1.37-1.49 (m, 2 H) 1.55-1.70 (m, 4 H) 2.03-2.20 (m, 6 H) 2.28-2.40 (m, 1 H) 3.95 (s, 3 H) 4.31-4.44 (m, 2 H) 4.62-4.72 (m, 1 H) 4.76-4.84 (m, 1 H) 4.86 (s, 2 H) 7.53 (s, 1 H) 7.66 (s, 1 H) 7.69 (s, 2 H) 7.75 (s, 1 H) 8.43 (s, 2 H) |
| 20 | 1H NMR (400 MHz, CHLOROFORM-d) δ ppm 0.86 (t, J=7.33 Hz, 6 H) 1.34-1.69 (m, 6 H) 1.72-1.85 (m, 4 H) 2.02-2.23 (m, 6 H) 2.30-2.41 (m, 1 H) 3.95 (s, 3 H) 4.08-4.21 (m, 2 H) 4.62-4.70 (m, 1 H) 4.71-4.82 (m, 3 H) 7.12 (d, J=1.77 Hz, 2 H) 7.22 (t, J=1.89 Hz, 1 H) 7.53 (s, 1 H) 7.66 (s, 1 H) 8.43 (s, 2 H) |
| 21 | 1H NMR (400 MHz, CHLOROFORM-d) δ ppm 0.85 (t, J=7.30 Hz, 6 H) 1.04-1.15 (m, 2 H) 1.41-1.49 (m, 4 H) 1.75-1.94 (m, 6 H) 2.03-2.21 (m, 5 H) 2.25-2.35 (m, 1 H) 3.94-3.98 (m, 5 H) 4.12-4.24 (m, 2 H) 4.77-4.85 (m, 1 H) 4.88 (s, 2 H) 7.54 (s, 1 H) 7.67 (s, 1 H) 7.71 (s, 2 H) 7.75 (s, 1 H) 8.44 (s, 2 H) |
| 22 | 1H NMR (400 MHz, CHLOROFORM-d) δ ppm 0.85 (t, J=7.33 Hz, 6 H) 1.35-1.65 (m, 8 H) 1.73-1.85 (m, 2 H) 2.02-2.20 (m, 6 H) 2.31-2.40 (m, 1 H) 3.95 (s, 3 H) 4.09-4.20 (m, 2 H) 4.61-4.72 (m, 1 H) 4.73-4.85 (m, 3 H) 7.10-7.21 (m, 2 H) 7.32 (s, 1 H) 7.53 (s, 1 H) 7.66 (s, 1 H) 8.43 (s, 2 H) |
| 23 | 1H NMR (400 MHz, CHLOROFORM-d) δ ppm 0.86 (t, J=7.33 Hz, 6 H) 1.38-1.53 (m, 4 H) 1.64-1.80 (m, 9 H) 2.11-2.22 (m, 4 H) 3.95 (s, 3 H) 4.22-4.36 (m, 3 H) 4.54-4.65 (m, 1 H) 4.86 (s, 2 H) 7.56 (s, 1 H) 7.66 (s, 1 H) 7.68 (s, 2 H) 7.75 (s, 1 H) 8.47 (s, 2 H) |
| 24 | 1H NMR (400 MHz, CHLOROFORM-d) δ ppm 0.84 (t, J=7.33 Hz, 6 H) 1.35-1.53 (m, 6 H) 1.74-1.83 (m, 4 H) 2.03-2.18 (m, 6 H) 2.29-2.40 (m, 1 H) 3.93-3.97 (m, 2 H) 4.05-4.09 (m, 2 H) 4.10-4.20 (m, 2 H) 4.61-4.75 (m, 2 H) 4.79 (s, 2 H) 7.68 (s, 2 H) 7.73 (s, 1 H) 8.11 (s, 2 H) |
| 26 | 1H NMR (400 MHz, CHLOROFORM-d) δ ppm 0.92 (t, J=7.30 Hz, 3 H) 1.41-1.51 (m, 6 H) 1.52-1.68 (m, 4 H) 1.76-1.84 (m, 1 H) 2.05-2.21 (m, 4 H) 2.24-2.51 (m, 3 H) 2.97-3.02 (m, 3 H) 3.26 (dd, J=12.59, 3.53 Hz, 1 H) 3.80-3.85 (m, 3 H) 4.23-4.33 (m, 2 H) 4.62-4.74 (m, 3 H) 4.88 (d, J=16.62 Hz, 1 H) 7.05-7.21 (m, 5 H) 7.62 (s, 2 H) 7.72 (s, 1 H) 8.05 (s, 2 H) |

Example 2

Synthesis of (4-{cis-2-benzyl-4-[(3,5-bis(trifluoromethyl)benzyl)-(5-bromopyrimidin-2-yl)-amino]-6-ethylpiperidine-1-carbonyl}-cyclohexyl)-acetic acid

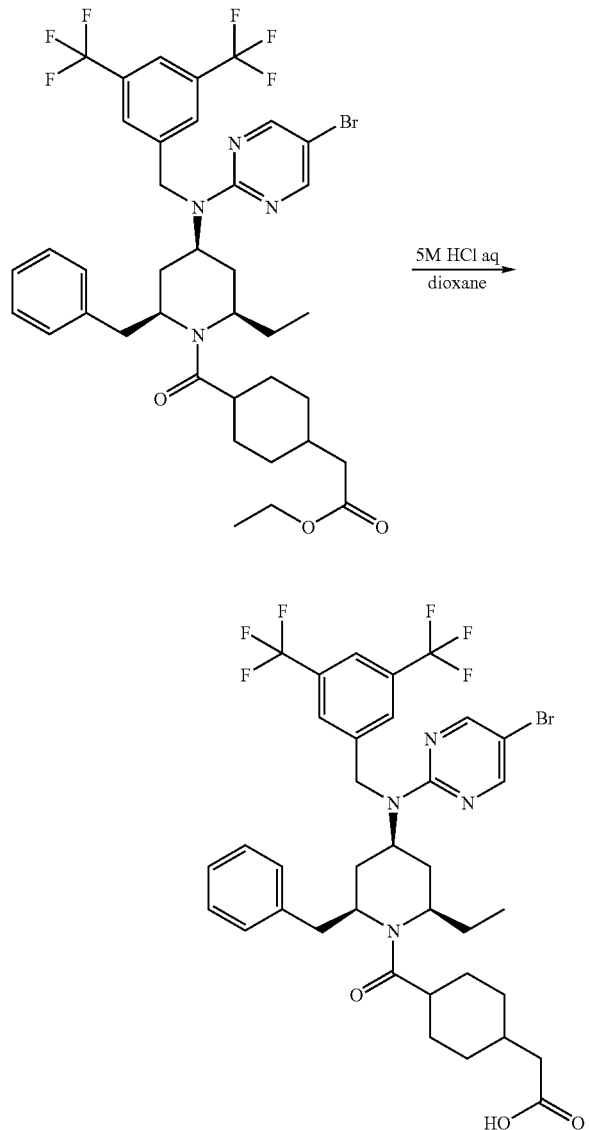

To a solution of (4-{cis-2-benzyl-4-[(3,5-bis(trifluoromethyl)benzyl)-(5-bromopyrimidin-2-yl)-amino]-6-ethylpiperidine-1-carbonyl}-cyclohexyl)-acetic acid ethyl ester (13 mg 0.0163 mmol) in dioxane (1 mL) is added aqueous 5M HCl (1 mL). The mixture is stirred at 100° C. for 3 hours. The product is purified by reverse-phase HPLC to give (4-{cis-2-benzyl-4-[(3,5-bis(trifluoromethyl)benzyl)-(5-bromopyrimidin-2-yl)-amino]-6-ethylpiperidine-1-carbonyl}-cyclohexyl)-acetic acid (2.3 mg, 18%); ESI-MS m/z: 769 [M+1]+, Retention time 2.61 min (condition A).

Example 3

Synthesis of trans-4-{cis-2-benzyl-4-[(3,5-bis(trifluoromethyl)benzyl)-(5-bromopyrimidin-2-yl)-amino]-6-ethylpiperidine-1-carbonyl}-cyclohexanecarboxylic acid

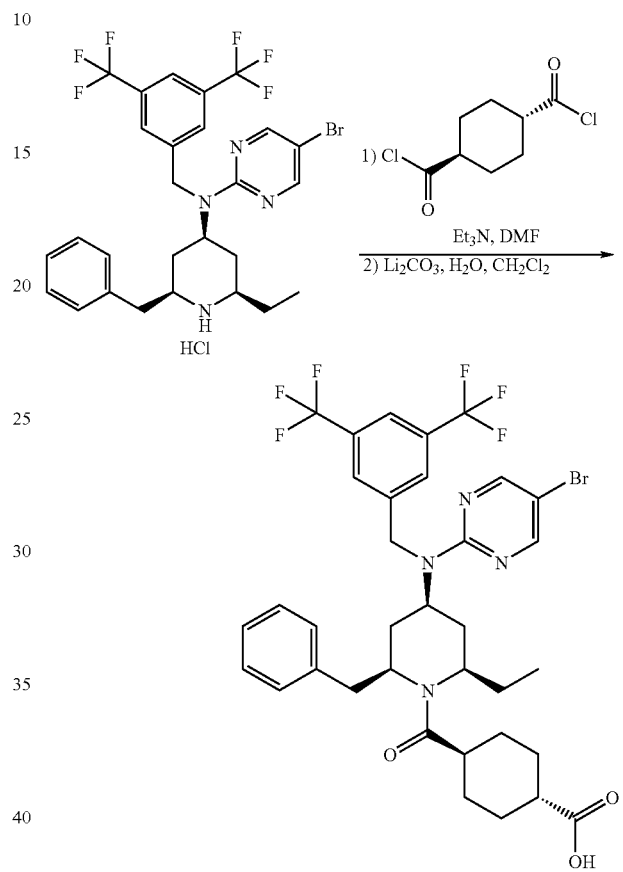

To solution of trans-cyclohexane-1,4-dicarboxylic acid (135 mg, 0.784 mmol) in THF (2 mL) is added thionyl chloride (572 uL, 7.84 mmol). The mixture is stirred at room temperature for 18 hours then the mixture is concentrated under reduced pressure. The obtained residue is added to a solution of (cis-2-benzyl-6-ethylpiperidin-4-yl)-(3,5-bis(trifluoromethyl)benzyl)-(5-bromo-pyrimidin-2-yl)-amine hydrochloride (50 mg, 0.0784 mmol), triethylamine (329 uL, 2.35 mmol) in DMF (2 mL). The mixture is stirred at 150° C. for 1 hour under microwave irradiation. To the mixture is added dichloromethane (5 mL), H2O (5 mL), and Li2CO3 (173 mg, 2.35 mmol). The mixture is stirred at room temperature for 2 hours and extracted with dichloromethane. The organic layer is concentrated under reduced pressure, and the obtained residue is purified by reverse-phase HPLC to give 4-{cis-2-benzyl-4-[(3,5-bis(trifluoromethyl)benzyl)-(5-bromopyrimidin-2-yl)-amino]-6-ethylpiperidine-1-carbonyl}-cyclohexanecarboxylic acid (9.0 mg, 15%); ESI-MS m/z 755 [M+1]+, Retention time 2.60 min (condition A).

The following compounds are prepared following the procedure of Example 3

| No | Product | ESI-MS m/z [M + 1]+ | Retention time (min) | Starting Material |
|---|---|---|---|---|
| 1 | 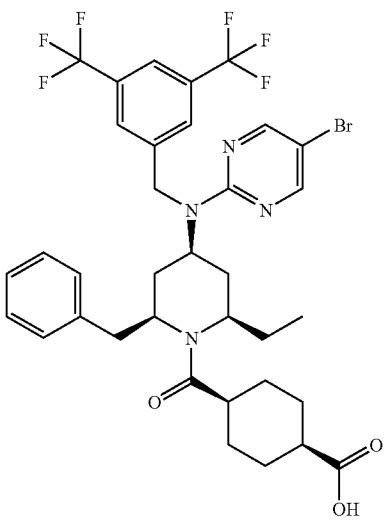 | 755 | 2.65 (condition A) | 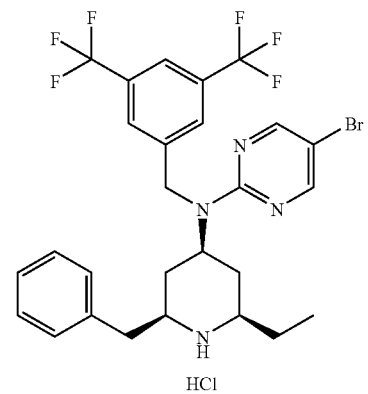 |

Example 4

Synthesis of cis-4-{[3,5-bis(trifluoromethyl)benzyl]-[5-(1-methyl-1H-pyrazol-4-yl)-pyrimidin-2-yl]-amino}-2,6-diethyl-piperidine-1-carboxylic acid 4-carbamoyl-butyl ester

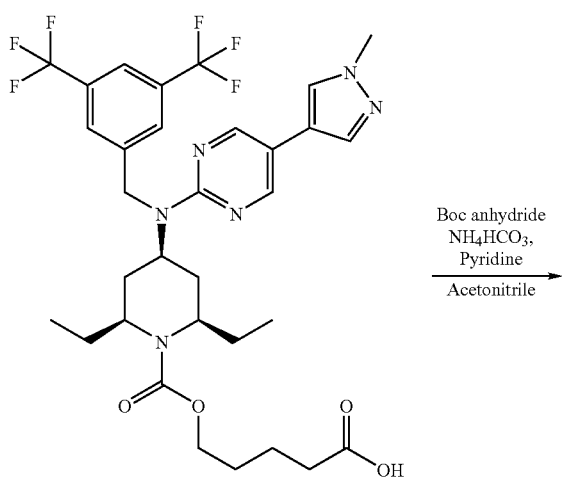

Boc anhydride
NH₄HCO₃,
Pyridine
―――――→
Acetonitrile

-continued

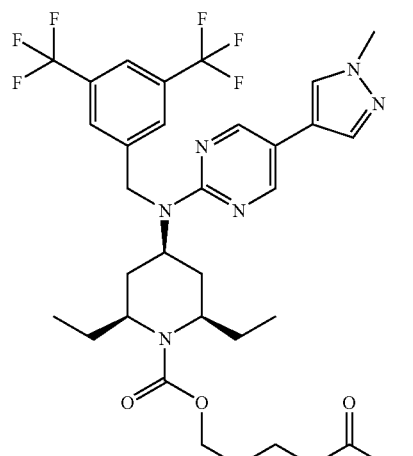

To a solution of cis-4-{(3,5-bis(trifluoromethyl)benzyl)-[5-(1-methyl-1H-pyrazol-4-yl)-pyrimidin-2-yl]-amino}-2,6-diethylpiperidine-1-carboxylic acid 4-carboxy-butyl ester (50 mg, 0.0730 mmol), di-tert-butyl dicarbonate (25.5 mg, 0.117 mmol), and pyridine (4.34 uL, 0.0533 mmol) in acetonitrile (1 mL) is added ammonium hydrogen carbonate (8.65 mg, 0.110 mmol) at room temperature. The mixture is stirred for 15 hours at room temperature. To the mixture, water is added and the solution is extracted with dichloromethane. The solvent is removed under reduced pressure, and the obtained residue is purified by silica gel column chromatography to give cis-4-{(3,5-bis(trifluoromethyl)benzyl)-[5-(1-methyl-1H-pyrazol-4-yl)-pyrimidin-2-yl]-amino}-2,6-diethylpiperidine-1-carboxylic acid 4-carbamoyl-butyl ester (37 mg, 74%); ESI-MS m/z: 684 [M+1]+, Retention time 2.30 min (condition A).

1H NMR (400 MHz, CHLOROFORM-d) δ ppm 0.85 (t, J=7.33 Hz, 6H) 1.41-1.55 (m, 4H) 1.69-1.85 (m, 6H) 2.10-2.21 (m, 2H) 2.29 (t, 2H) 3.95 (s, 3H) 4.10-4.22 (m, 4H) 4.74-4.83 (m, 1H) 4.86 (s, 2H) 5.29 (br. s., 1H) 5.49 (br. s., 1H) 7.54 (s, 1H) 7.66 (s, 1H) 7.71 (s, 2H) 7.75 (s, 1H) 8.43 (s, 2H)

Example 5

Synthesis of cis-4-[(3,5-bis(trifluoromethyl)benzyl)-(5-imidazol-1-yl-pyrimidin-2-yl)-amino]-2,6-diethylpiperidine-1-carboxylic acid trans-4-carboxy-cyclohexyl ester

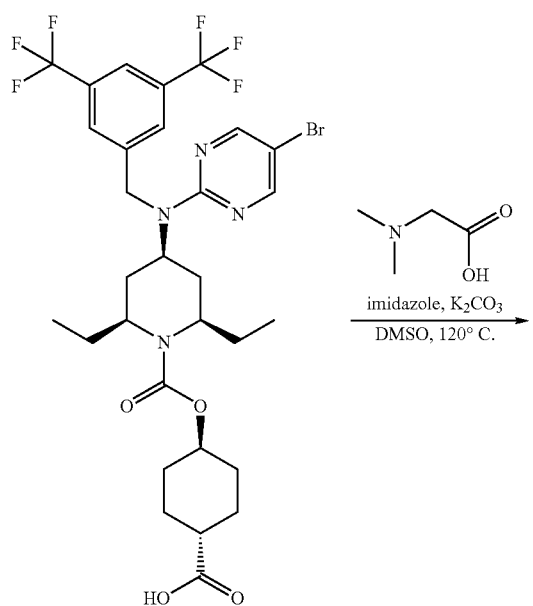

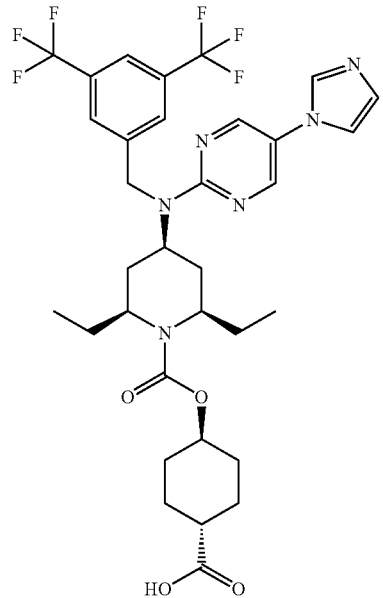

A mixture of cis-4-[(3,5-bis(trifluoromethyl)benzyl)-(5-bromo-pyrimidin-2-yl)-amino]-2,6-diethylpiperidine-1-carboxylic acid trans-4-carboxy-cyclohexyl ester (0.56 mmol, 398 mg), imidazole (1.12 mmol, 77 mg), copper iodide (0.56 mmol, 107 mg), dimethylamino-acetic acid (0.56 mmol, 58 mg) and potassium carbonate (1.68 mmol, 232 mg) in dimethyl sulfoxide (2 mL) is allowed to warm to 120° C. and stirred for 67 hours. The mixture is cooled to room temperature and then water is added. The mixture is filtrated and extracted with CH2Cl2. The combined organic layer is concentrated under reduced pressure, and obtained residue is purified by silica gel column chromatography (eluent: CH2Cl2/EtOH) to give cis-4-[(3,5-bis(trifluoromethyl)benzyl)-(5-imidazol-1-yl-pyrimidin-2-yl)-amino]-2,6-diethylpiperidine-1-carboxylic acid trans-4-carboxy-cyclohexyl ester (100 mg, 26%); ESI-MS m/z: 697 [M+1]+, Retention time 2.00 min (condition A).

1H NMR (400 MHz, CHLOROFORM-d) δ ppm 0.85 (t, J=7.33 Hz, 6H) 1.36-1.51 (m, 2H) 1.52-1.65 (m, 4H) 1.72-1.85 (m, 4H) 2.02-2.22 (m, 6H) 2.28-2.39 (m, 1H) 4.12-4.23 (m, 2H) 4.62-4.69 (m, 1H) 4.72-4.83 (m, 1H) 4.89 (s, 2H) 7.13 (s, 1H) 7.24 (s, 1H) 7.70 (s, 2H) 7.72 (s, 1H) 7.77 (s, 1H) 8.39 (s, 2H)

Preparation of the starting materials can be done as follows.

Example 6

Synthesis of cis-2-benzyl-4-[(3,5-bis(trifluoromethyl)benzyl)-(5-morpholin-4-yl-pyrimidin-2-yl)-amino]-6-ethylpiperidine-1-carboxylic acid tert-butyl ester

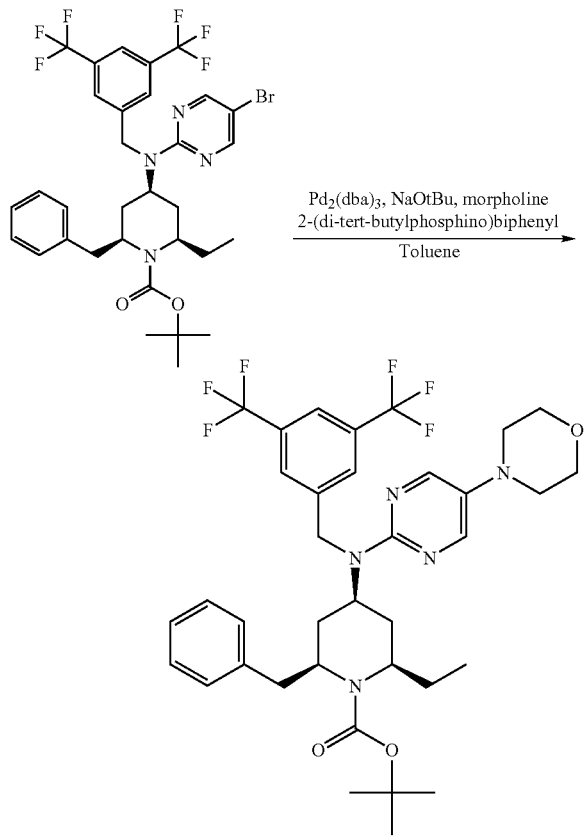

To a mixture of cis-2-benzyl-4-[(3,5-bis(trifluoromethyl)benzyl)-(5-bromo-pyrimidin-2-yl)-amino]-6-ethylpiperidine-1-carboxylic acid tert-butyl ester (315 mg, 0.449 mmol), tris(dibenzylideneacetone)dipalladium(0) (82.3 mg, 0.0900 mmol), 2-(di-tert-butylphosphino)biphenyl (53.7 mg, 0.180 mmol), and sodium tert-butoxide (173 mg, 180 mmol) in toluene is added morpholine (78.5 uL, 0.898 mmol) at room temperature under nitrogen. The mixture is stirred at 100° C. for 3 hours. After the mixture is cooled to room temperature, saturated aqueous NH4Cl is added, and extracted with AcOEt. The combined organic layer is washed with brine, dried over Na2SO4, filtrated, concentrated under reduced pressure, and purified by silica gel column chromatography to give cis-2-benzyl-4-[(3,5-bis(trifluoromethyl benzyl)-(5-morpholin-4-yl-pyrimidin-2-yl)-amino]-6-ethylpiperidine-1-carboxylic acid tert-butyl ester (265 mg, 83.4%); ESI-MS m/z 708 [M+1]+, Retention time 2.61 min (condition A).

The following compounds are prepared following the procedure of Example 6

| No | Product | ESI-MS m/z [M + 1]+ | Retention time (min) | Starting Material |
|---|---|---|---|---|
| 1 | (structure, racemate) | 742 | 2.30 (condition A) | (structure, racemate) |

-continued

| No | Product | ESI-MS m/z [M + 1]+ | Retention time (min) | Starting Material |
|---|---|---|---|---|
| 2 | 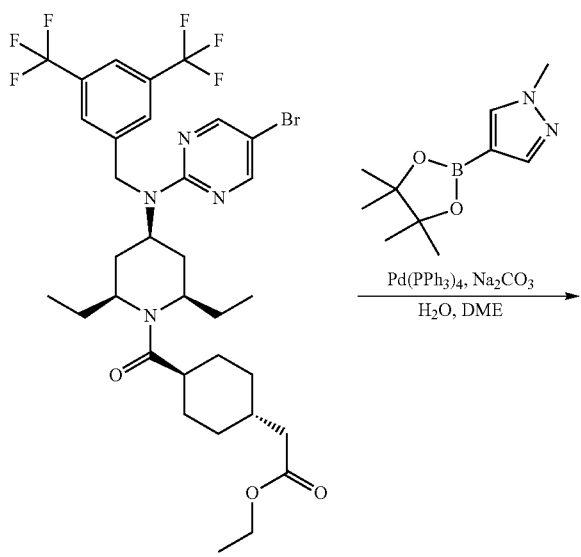 | 646 | 2.43 (condition A) | |

Example 7

Synthesis of [trans-4-(cis-4-{(3,5-bis(trifluoromethyl)benzyl)-[5-(1-methyl-1H-pyrazol-4-yl)-pyrimidin-2-yl]-amino}-2,6-diethylpiperidine-1-carbonyl)-cyclohexyl]-acetic acid ethyl ester

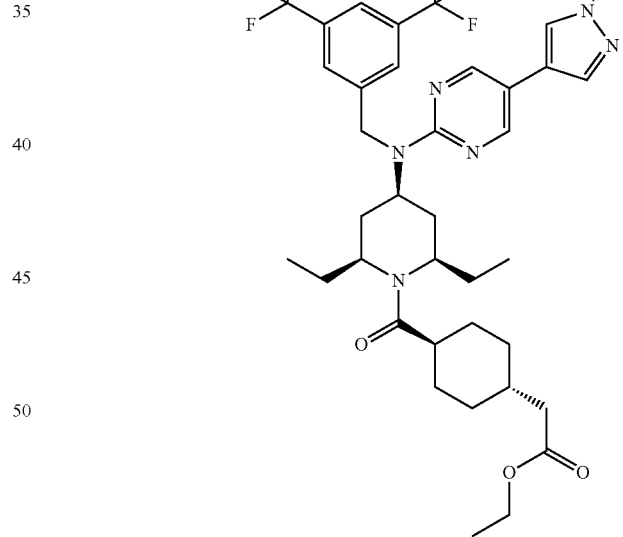

(trans-4-(cis-4-[(3,5-bis(trifluoromethyl)benzyl)-(5-bromo-pyrimidin-2-yl)-amino]-2,6-diethylpiperidine-1-carbonyl)-cyclohexyl)-acetic acid ethyl ester (205 mg, 0.419 mmol), 1-methyl-4-(4,4,5,5-tetramethyl-[1,3,2]dioxaborolan-2-yl)-1H-pyrazole (87.2 mg, 0.419 mmol), tetrakis(triphenylphosphine)palladium(0) (32.2 mg, 0.0279 mmol), and sodium carbonate (59.1 mg, 0.558 mmol) are dissolved in H2O (0.54 mL) and DME (2.7 mL) at room temperature. The mixture is stirred at 95° C. for 3 hours, and cooled to room temperature. To the mixture is added water and the solution is extracted with dichloromethane. The solvent is removed under reduced pressure, and the obtained residue is purified by silica gel column chromatography to give [trans-4-(cis-4-{[3,5-bis(trifluoromethyl)benzyl]-[5-(1-methyl-1H-pyrazol-4-yl)-pyrimidin-2-yl]-amino}-2,6-diethylpiperidine-1-carbonyl)-cyclohexyl]-acetic acid ethyl ester; ESI-MS m/z 737 [M+1]+, Retention time 2.35 min (condition A).

The following compounds are prepared following the procedure of Example 7

| No | Product | ESI-MS m/z [M + 1]+ | Retention time (min) | Starting Material |
|----|---------|---------------------|----------------------|-------------------|
| 1 | 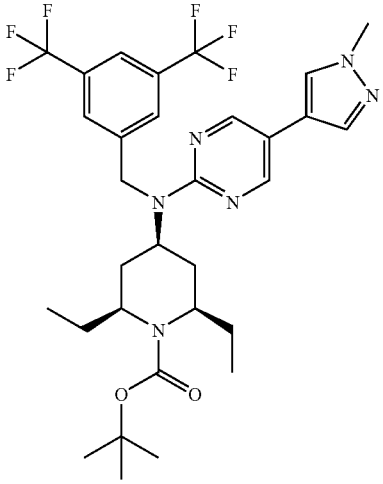 | 641 | 2.56 (condition A) | 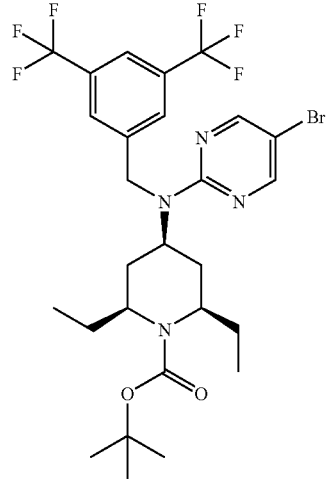 |
| 2 | 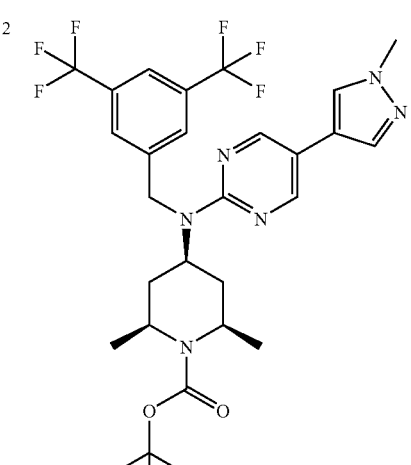 | 613 | 4.90 (condition C) | 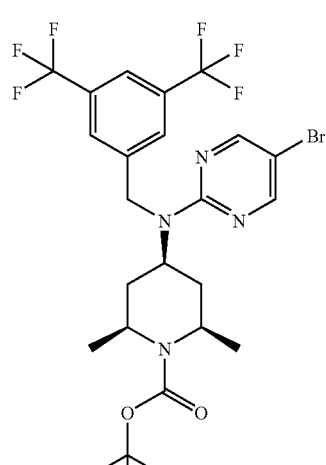 |

Example 8

Synthesis of [trans-4-(cis-4-{[3,5-bis(trifluoromethyl)benzyl]-[5-(1H-pyrazol-4-yl)-pyrimidin-2-yl]-amino}-2,6-diethylpiperidine-1-carbonyl)-cyclohexyl]-acetic acid ethyl ester

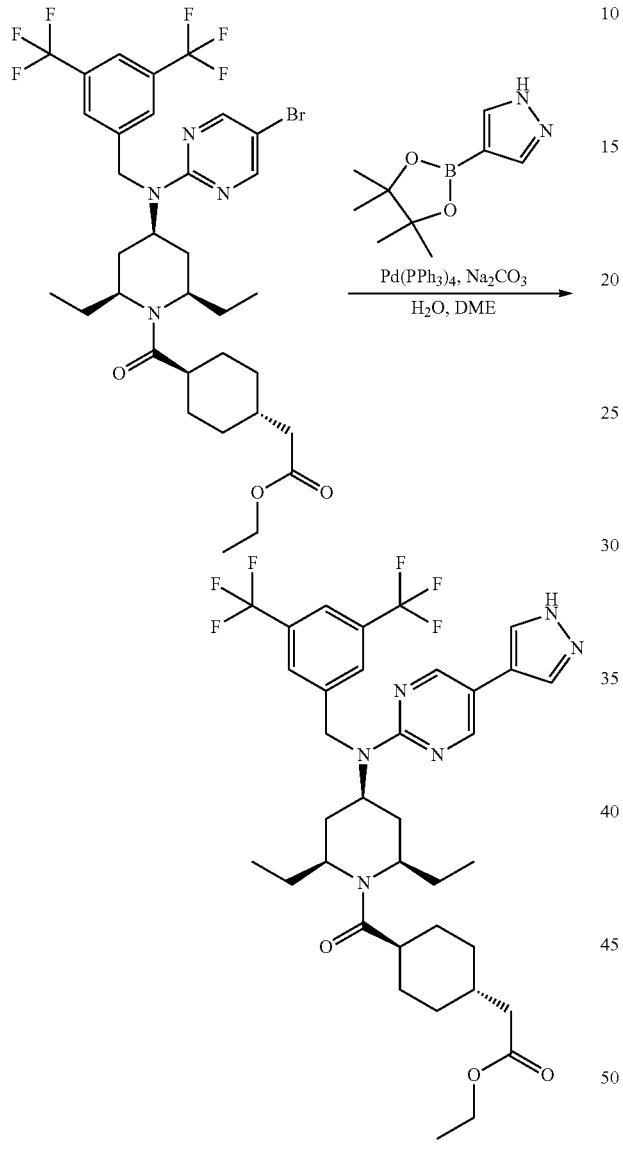

(trans-4-{cis-4-[(3,5-bis(trifluoromethyl)benzyl)-(5-bromo-pyrimidin-2-yl)-amino]-2,6-diethylpiperidine-1-carbonyl}-cyclohexyl)-acetic acid ethyl ester (205 mg, 0.419 mmol), 1-(tetrahydro-pyran-2-yl)-4-(4,4,5,5-tetramethyl-[1,3,2]dioxaborolan-2-yl)-1H-pyrazole (116 mg, 0.419 mmol), tetrakis(triphenylphosphine)palladium(0) (32.2 mg, 0.0279 mmol), and sodium carbonate (59.1 mg, 0.558 mmol) are dissolved in H2O (0.54 ml) and DME (2.7 ml). The mixture is stirred at 95° C. for 2 hours and cooled to room temperature. To the mixture is added 1M HCl in EtOH (6 mL), and the solution is stirred at room temperature for 2 hours. To the mixture is added 4M HCl in dioxane (6 mL), and the solution is stirred at room temperature for 2 hours. Saturated aqueous NaHCO3 is added to the mixture, and the solution is extracted with dichloromethane. The solvent is removed under reduced pressure, and the obtained residue is purified by silica gel column chromatography to give [trans-4-(cis-4-{(3,5-bis(trifluoromethyl)benzyl)-[5-(1H-pyrazol-4-yl)-pyrimidin-2-yl]-amino}-2,6-diethylpiperidine-1-carbonyl)-cyclohexyl]-acetic acid ethyl ester (140 mg 69.4%); ESI-MS m/z 723 [M+1]+, Retention time 2.29 min (condition A).

Example 9 cis-4-{(3,5-Bis(trifluoromethyl)benzyl)-[5-((S)-3-hydroxy-pyrrolidin-1-yl)-pyrimidin-2-yl]-amino}-2,6-diethylpiperidine-1-carboxylic acid tert-butyl ester

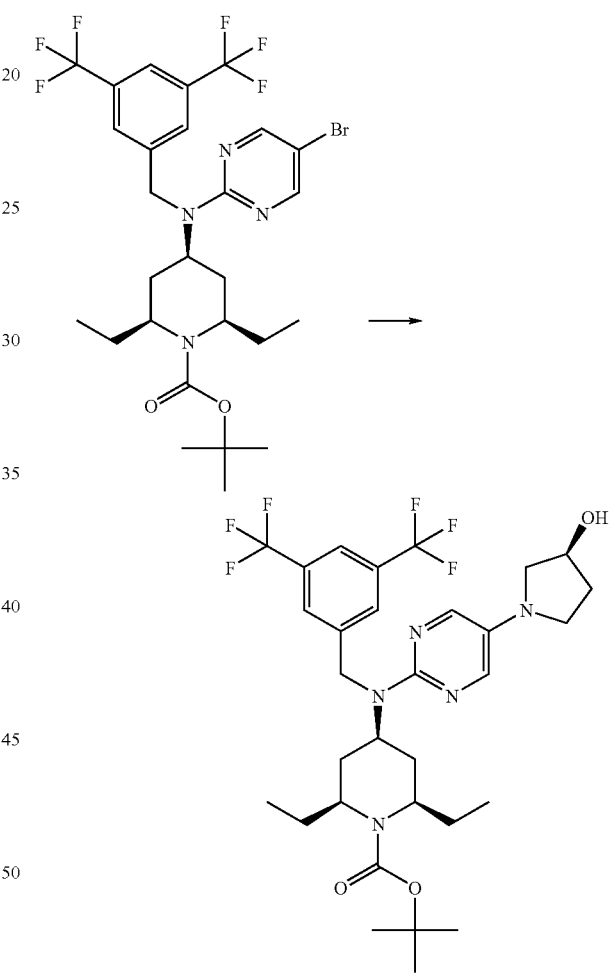

Pd2(dba)3 (10.7 mg, 0.012 mmol) and 2-(di-tert-butylphosphino)biphenyl (7.0 mg, 0.023 mmol) are dissolved in toluene (2 mL). Upon cooling, sodium tert-butoxide (90 mg, 0.940 mmol), (S)-(−)-3-benzoyloxypyrrolidine (0.67 g, 5.5 mmol) and cis-4-[(3,5-bis(trifluoromethyl)benzyl)-(5-bromo-pyrimidin-2-yl)-amino]-2,6-diethylpiperidine-1-carboxylic acid tert-butyl ester (0.52 g, 2.2 mmol) are added, and the reaction mixture is heated at 100° C. for 3 hours. After cooling to room temperature, MeOH (4 mL), THF (1 mL) and aqueous 5M NaOH is added, and the reaction mixture is stirred at room temperature for additional 1 hour. After adding saturated aqueous NH4Cl, the mixture is extracted with EtOAc. The combined organic layer after dried over MgSO4 is concentrated to obtain cis-4-{(3,5-bis(trifluoromethyl)benzyl)-[5-((S)-3-hydroxy-pyrrolidin-1-yl)-pyrimidin-2-yl]-amino}-2,6-diethylpiperidine-1-carboxylic acid tert-butyl ester as colorless oil (110 mg, 73%) after purification by silica gel column chromatography.

The following compounds are prepared using the same procedure as described in Example 3.

| No. | Product | ESI-MS m/z [M + 1]+ | Retention time (min) | Starting Material | Starting Material |
|---|---|---|---|---|---|
| 1 | 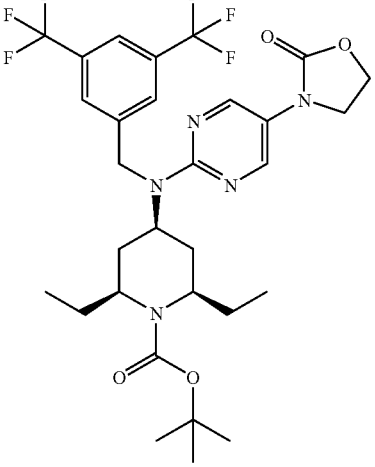 | 646 | 2.40 (condition A) |  | 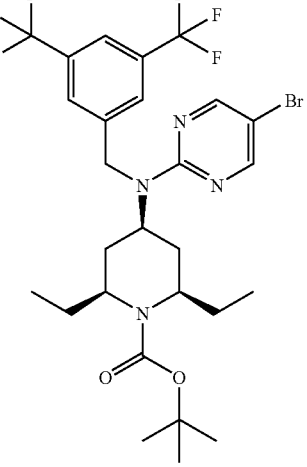<br>trans-cyclohexane-1,2-diamine instead of dimethylamino-acetic acid |
| 2 | 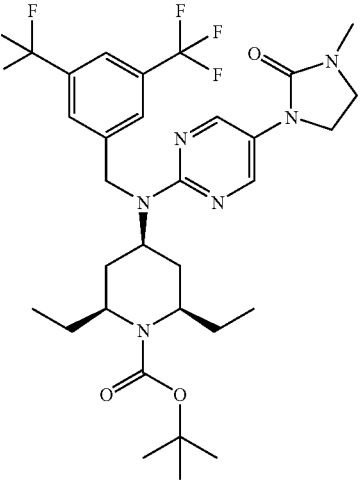 | 659 | 2.42 (condition A) |  | 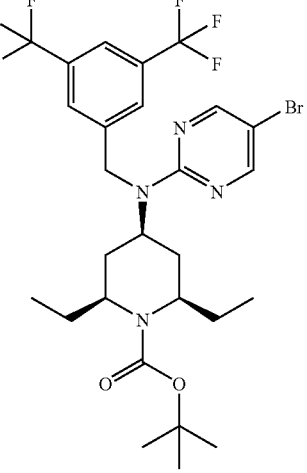<br>trans-cyclohexane-1,2-diamine instead of dimethylamino-acetic acid |

Example 10

Synthesis of (4-{cis-2-benzyl-4-[(3,5-bis(trifluoromethyl)benzyl)-(5-bromo-pyrimidin-2-yl)-amino]-6-ethylpiperidine-1-carbonyl}-cyclohexyl)-acetic acid ethyl ester

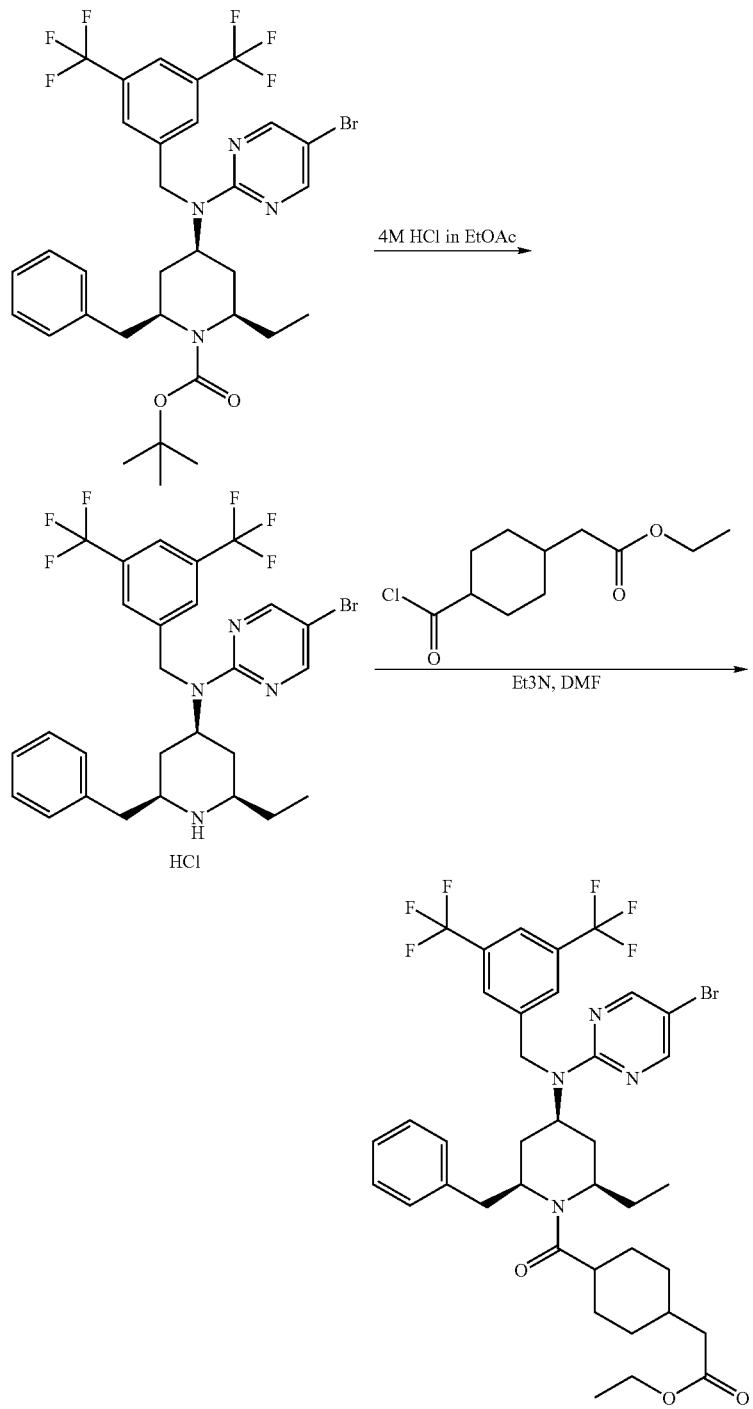

cis-2-benzyl-4-[(3,5-bis(trifluoromethyl)benzyl)-(5-bromo-pyrimidin-2-yl)-amino]-6-ethyl-piperidine-1-carboxylic acid tert-butyl ester (900 mg, 1.29 mmol) is dissolved in 4M HCl in AcOEt. The solution is stirred at room temperature for 4 hours then removed under reduced pressure. To the obtained residue is added diethyl ether, and precipitates are filtered and washed with ether. The solid is dried under reduced pressure to give (cis-2-benzyl-6-ethylpiperidin-4-yl)-(3,5-bis(trifluoromethyl)benzyl)-(5-bromo-pyrimidin-2-yl)-amine hydrochloride (771 mg 93.6%); ESI-MS m/z 601 [M+1]+, Retention time 2.14 min (condition A).

To a solution of 4-ethoxycarbonylmethyl-cyclohexanecarboxylic acid (83.9 mg, 0.392 mmol) in THF 1 mL is added thionyl chloride (143 uL, 1.96 mmol). The mixture is stirred at room temperature for 18 hours then concentrated under reduced pressure. The obtained residue is added to a solution of (cis-2-benzyl-6-ethylpiperidin-4-yl)-[3,5-bis(trifluoromethyl)benzyl]-(5-bromo-pyrimidin-2-yl)-amine hydrochloride (50 mg, 0.0784 mmol), triethylamine (110 uL, 0.784 mmol) in DMF (2 ml). The mixture is stirred at 150° C. for 1 hour under microwave irradiation. The product is purified by reverse-phase HPLC to give (4-{cis-2-benzyl-4-[(3,5-bis(trifluoromethyl)benzyl)-(5-bromopyrimidin-2-yl)-amino]-6-ethylpiperidine-1-carbonyl}-cyclohexyl)-acetic acid ethyl ester (13 mg, 20.8%); ESI-MS m/z 797 [M+1]+, Retention time 2.79 min (condition A).

The following compounds are prepared following the procedure of Example 10 using corresponding carboxylic acid.

| No | Product | ESI-MS m/z [M + 1]+ | Retention time (min) | Starting Material |
|----|---------|---------------------|----------------------|-------------------|
| 1 | 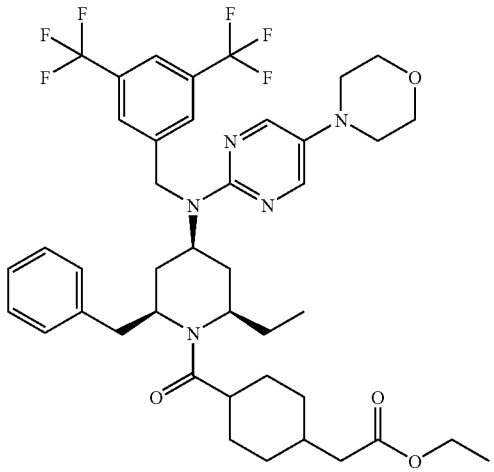 | 804 | 2.46 (condition A) | 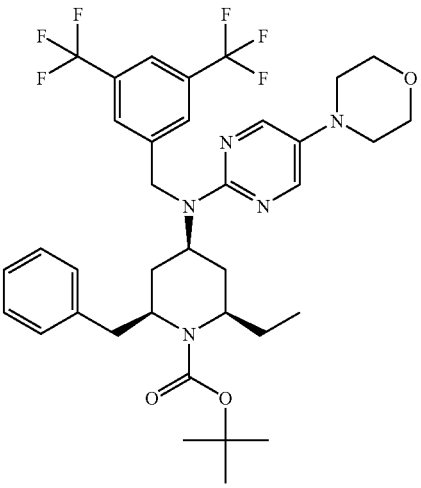 |
| 2 | 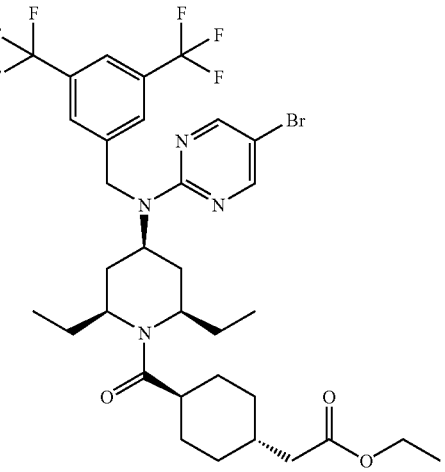 | 735 | 2.54 (condition A) | 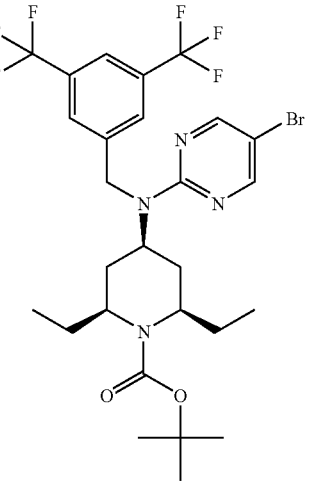 |

Example 11

Synthesis of cis-4-{(3,5-bis(trifluoromethyl)benzyl)-[5-(1-methyl-1H-pyrazol-4-yl)-pyrimidin-2-yl]-amino}-2,6-diethylpiperidine-1-carboxylic acid 3-methoxycarbonyl-propyl ester

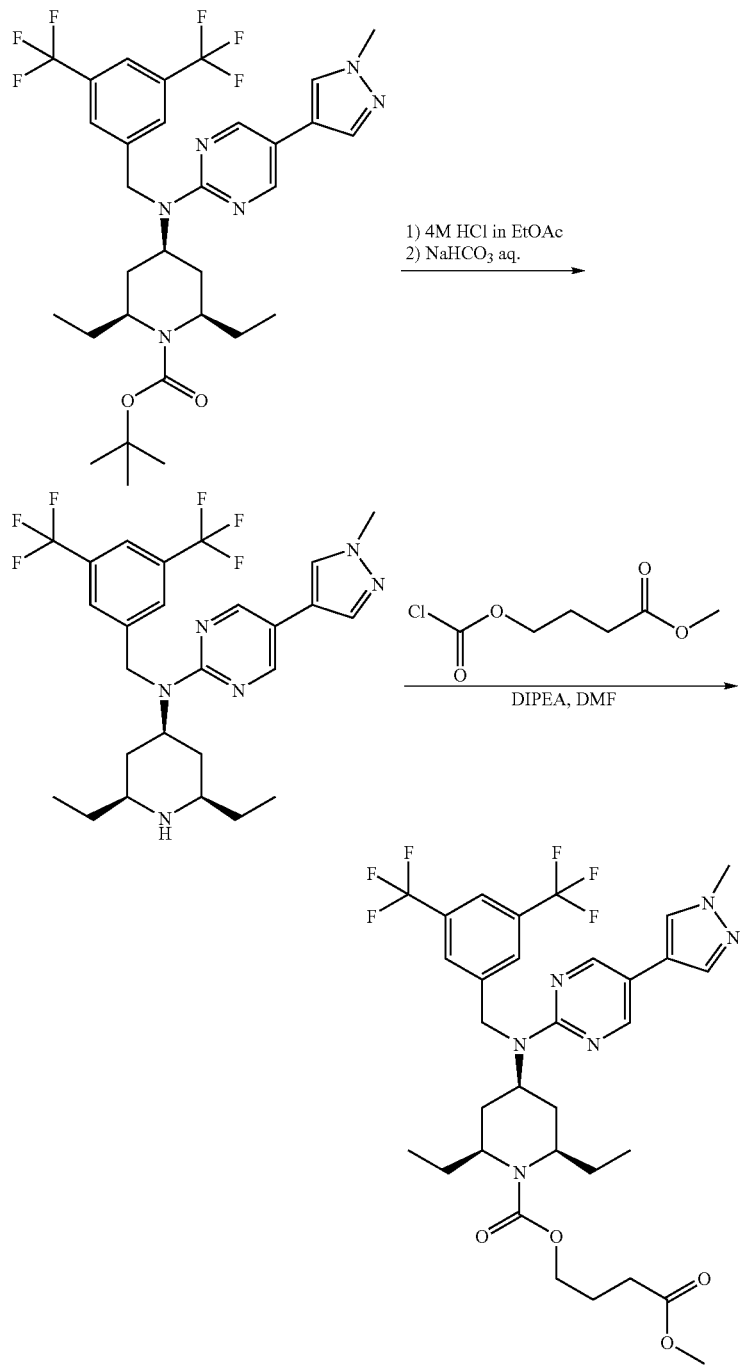

cis-4-{(3,5-bis(trifluoromethyl)benzyl)-[5-(1-methyl-1H-pyrazol-4-yl)-pyrimidin-2-yl]-amino}-2,6-diethylpiperidine-1-carboxylic acid tert-butyl ester is dissolved in 4M HCl in AcOEt. The solution is stirred at room temperature for 2 hours and precipitates are collected by filtration. To the solid, saturated aqueous NaHCO3 and AcOEt are added, and the solution is extracted with AcOEt. The organic layer is washed with brine, dried over MgSO4, and concentrated under reduced pressure to give (3,5-bis(trifluoromethyl)benzyl)-(cis-2,6-diethylpiperidin-4-yl)-[5-(1-methyl-1H-pyrazol-4-yl)-pyrimidin-2-yl]-amine (5.0 g, 91%); ESI-MS m/z 541 [M+1]+, retention time 1.84 min (condition A).

To 4-hydroxy-butyric acid methyl ester (43.7 mg, 0.370 mmol) is added a solution of triphosgene (73.6 mg, 0.248 mmol) in dichloromethane (2 mL) and a solution of pyridine (31.4 uL, 0.388 mL) in dichloromethane (2 mL) sequentially at 0° C. The mixture is stirred at room temperature for 3 hours. To the mixture is added saturated aqueous NH4Cl, and the mixture is extracted with dichloromethane. The solvent is removed under reduced pressure. The obtained residue is added to a solution of (3,5-bis(trifluoromethyl)benzyl)-(cis-2,6-diethylpiperidin-4-yl)-[5-(1-methyl-1H-pyrazol-4-yl)-pyrimidin-2-yl]-amine (100 mg, 0.185 mmol) in DMF (100 uL) at room temperature then added diisopropylethylamine (60 uL, 0.463 mmol). After stirring at room temperature for 15 hours, H2O is added, and the solution is extracted with dichloromethane. The organic layer is concentrated under reduced pressure, and the residue is purified by silica gel column chromatography to give cis-4-{(3,5-bis(trifluoromethyl)benzyl)-[5-(1-methyl-1H-pyrazol-4-yl)-pyrimidin-2-yl]-amino}-2,6-diethylpiperidine-1-carboxylic acid 3-methoxycarbonylpropyl ester (121 mg, 95.4%); ESI-MS m/z 685 [M+1]+, Retention time 2.29 min (condition A).

The following compounds are prepared following the procedure of Example 11 using corresponding alcohol.

| No. | Product | ESI-MS m/z [M + 1]+ | Retention time (min) |
|---|---|---|---|
| 1 | 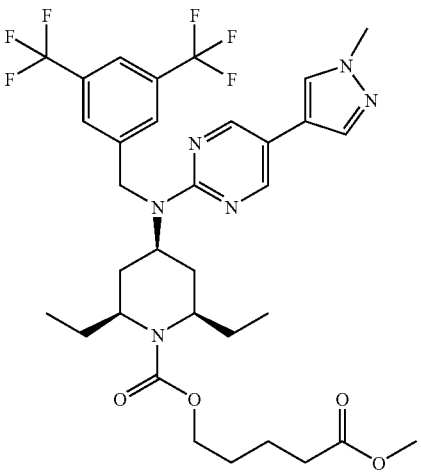 | 699 | 2.32 (condition A) |
| 2 | 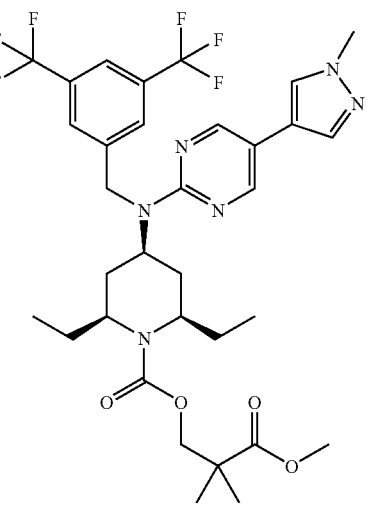 | 699 | 2.34 (condition A) |

| | | | |
|---|---|---|---|
| 3 | 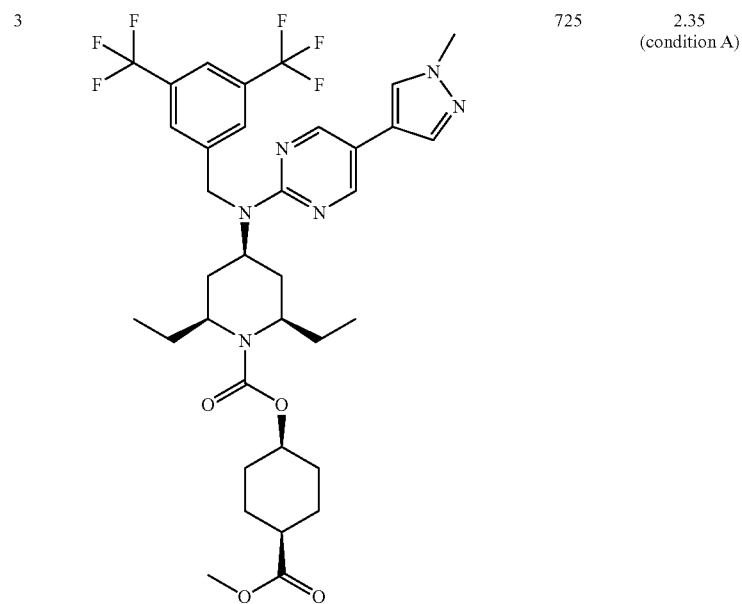 | 725 | 2.35 (condition A) |
| 4 | 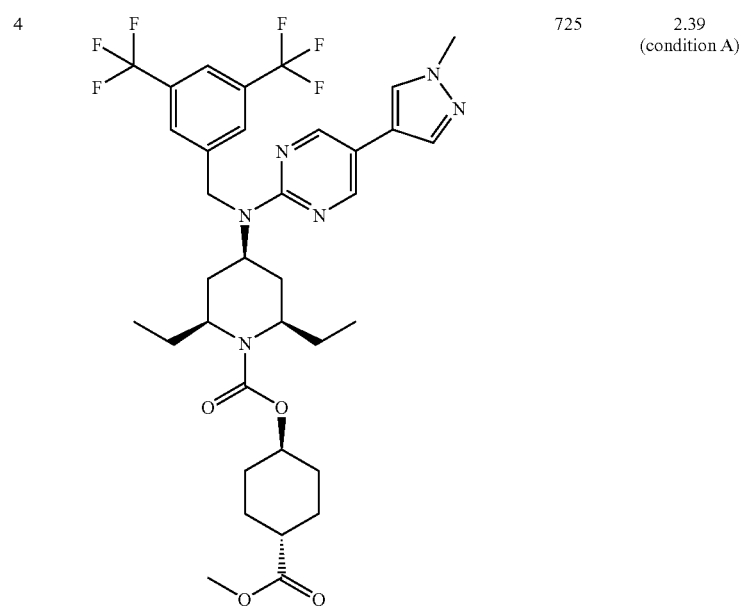 | 725 | 2.39 (condition A) |

| 5 | 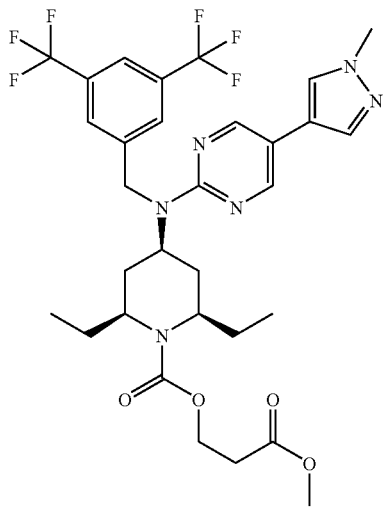 | 671 | 2.25 (condition A) |
| 6 | 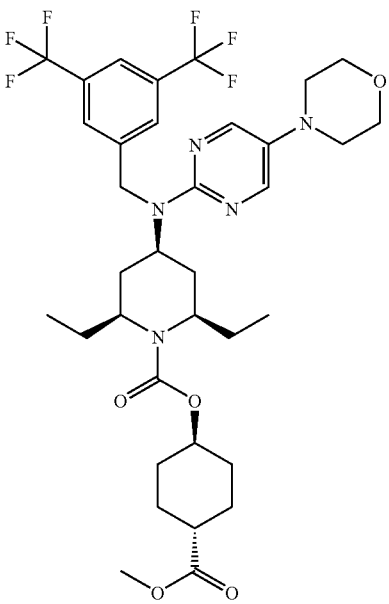 | 730 | 2.39 (condition A) |
| 7 | 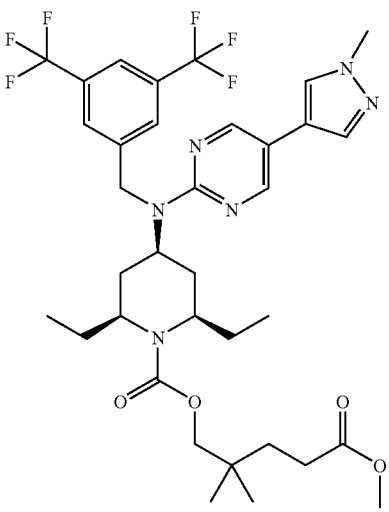 | 723 | 2.36 (condition A) |

| | | | |
|---|---|---|---|
| 8 | 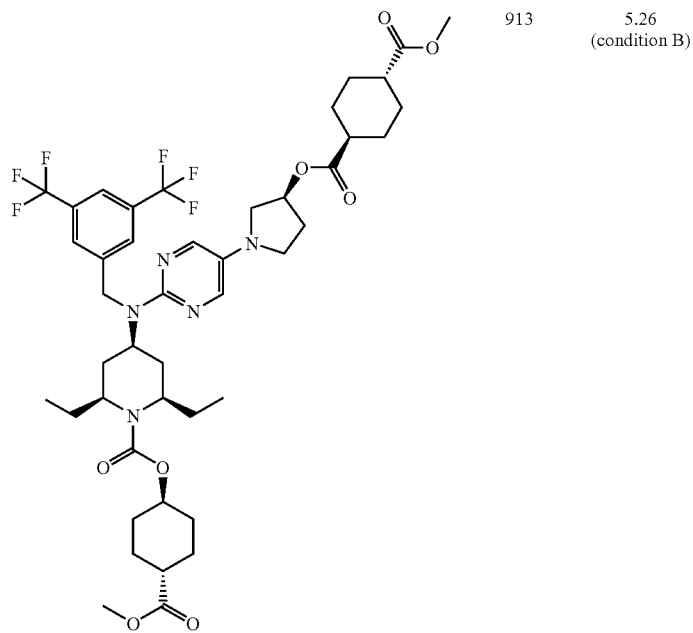 | 913 | 5.26 (condition B) |
| 9 | 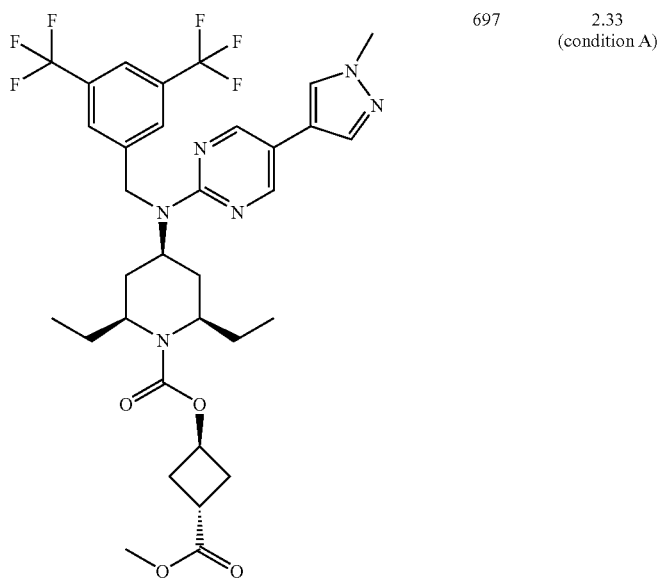 | 697 | 2.33 (condition A) |

| | | | |
|---|---|---|---|
| 10 | 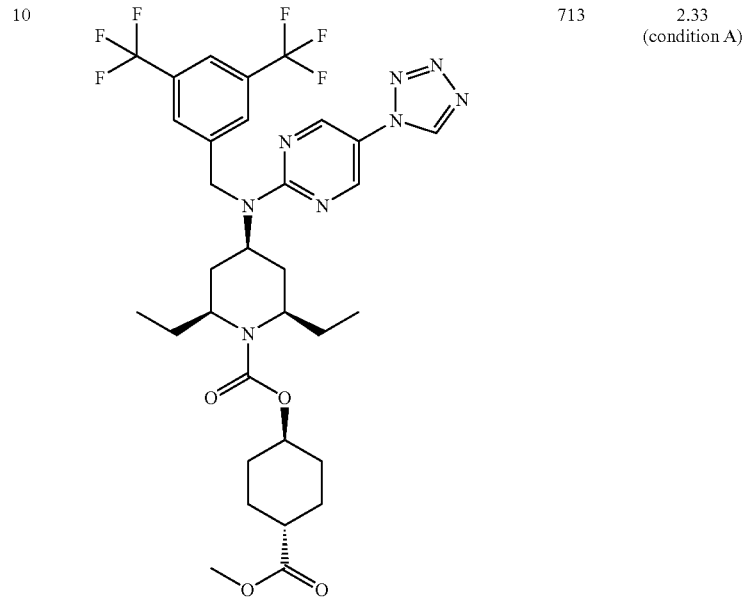 | 713 | 2.33 (condition A) |
| 11 | 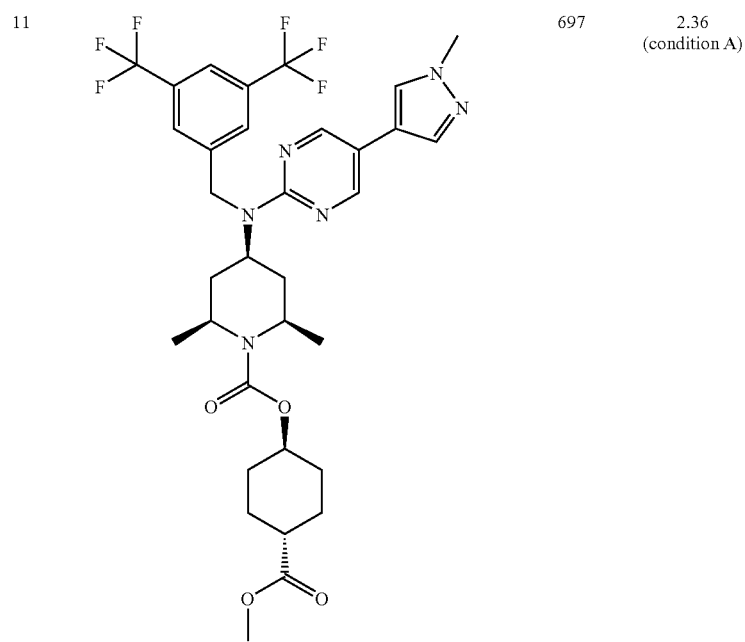 | 697 | 2.36 (condition A) |

-continued
| 12 | 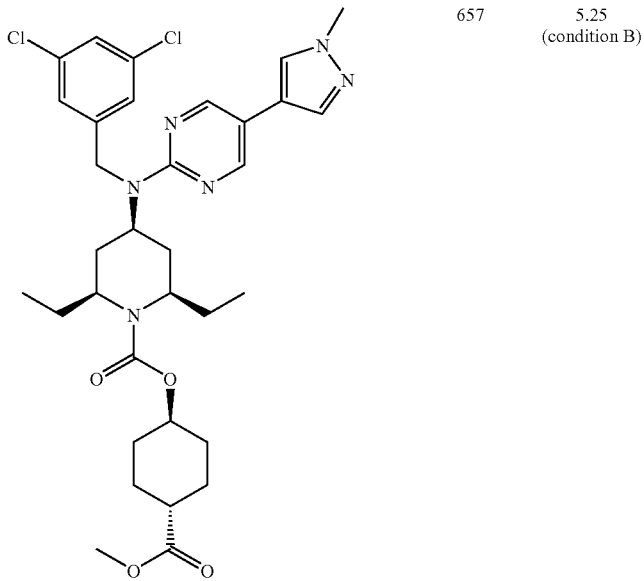 | 657 | 5.25 (condition B) |
| 13 | 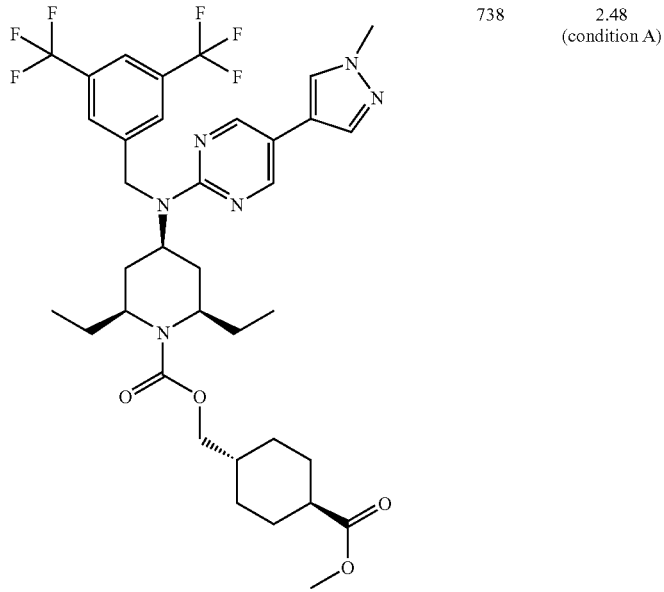 | 738 | 2.48 (condition A) |

| | | | |
|---|---|---|---|
| 14 | 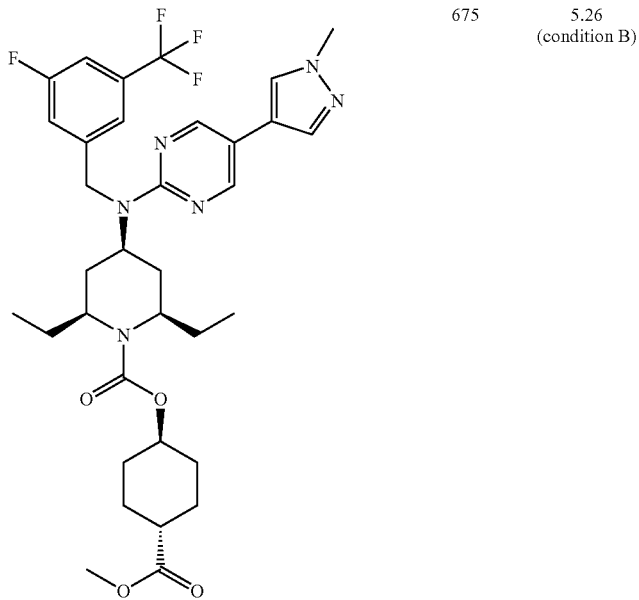 | 675 | 5.26 (condition B) |
| 15 | 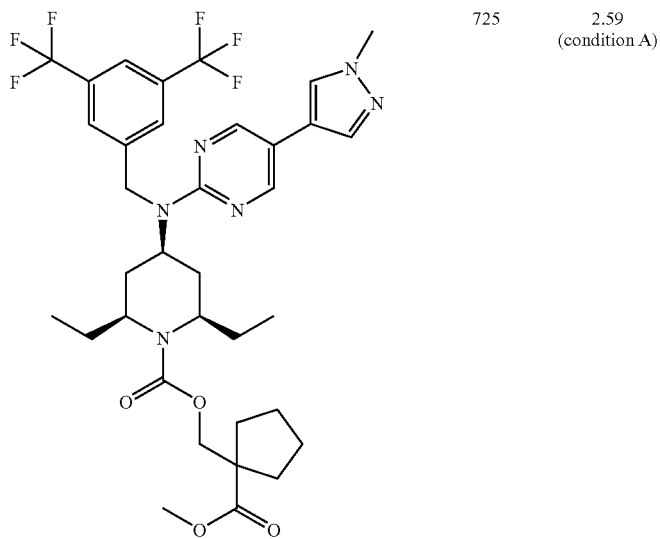 | 725 | 2.59 (condition A) |

| | | | |
|---|---|---|---|
| 16 | 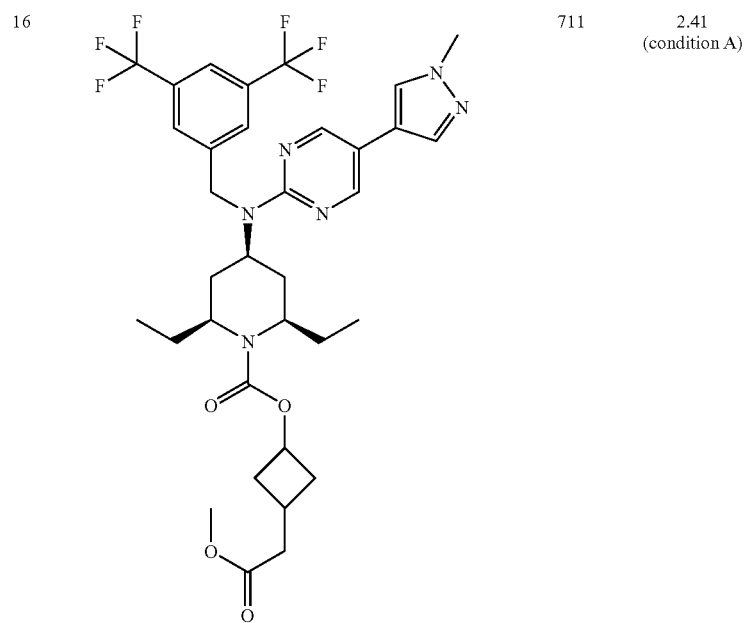 | 711 | 2.41 (condition A) |
| 17 | 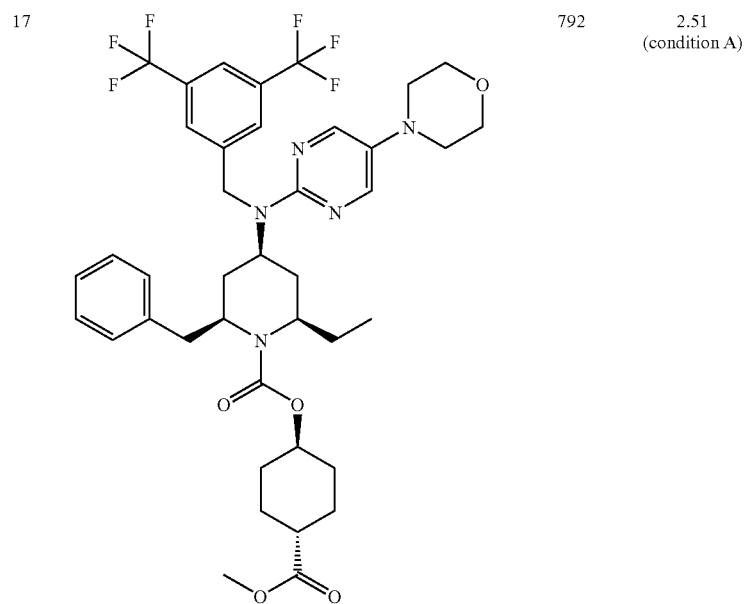 | 792 | 2.51 (condition A) |

| | | | |
|---|---|---|---|
| 18 | 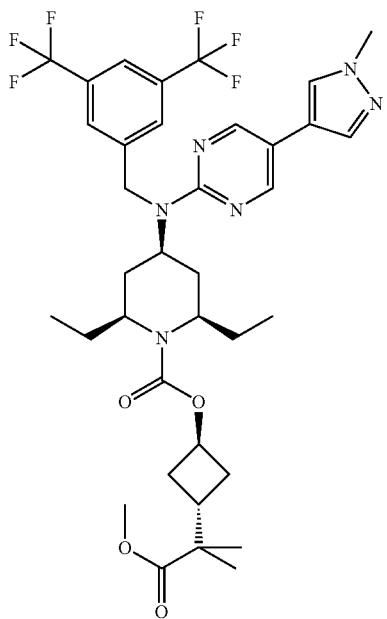 | 739 | 2.53 (condition A) |
| 19 | 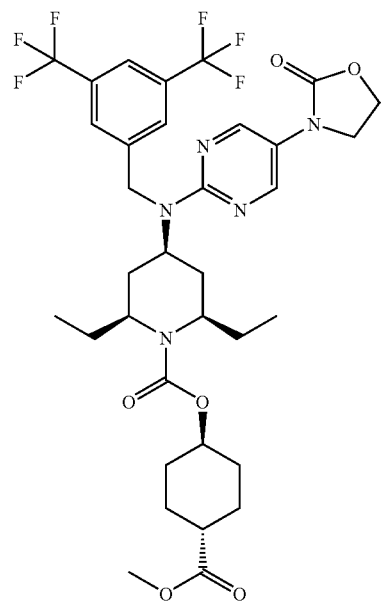 | 730 | 2.34 (condition A) |

| | | | |
|---|---|---|---|
| 20 | 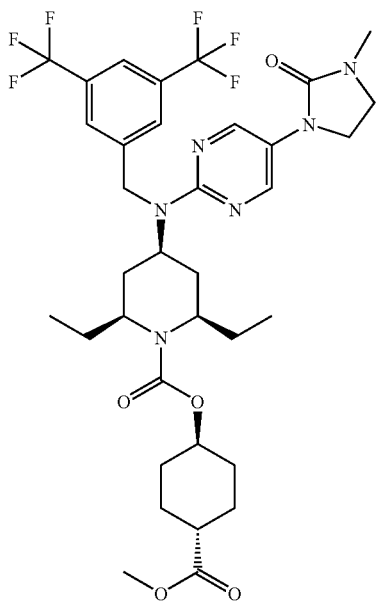 | 743 | 2.36 (condition A) |
| 21 | 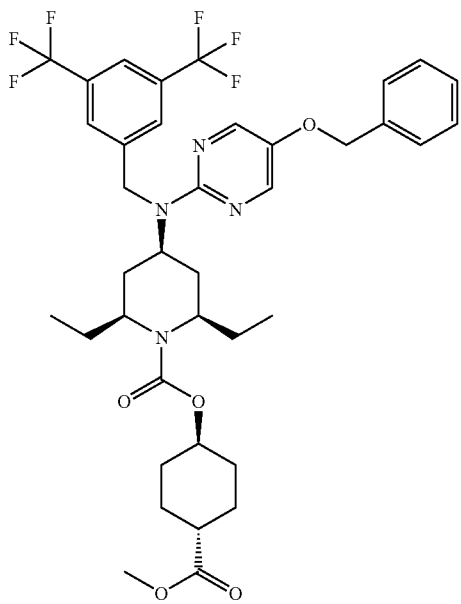 | 751 | 2.63 (condition A) |

| No. | Starting Material | Starting Material |
|---|---|---|
| 1 |  | 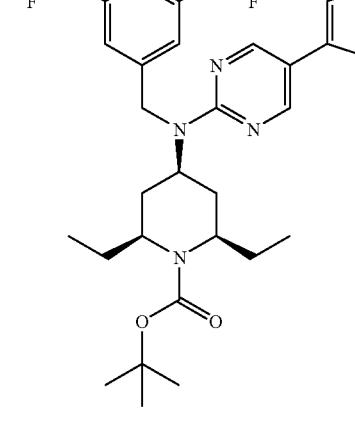 |
| 2 | 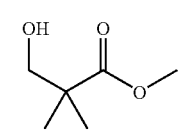 | 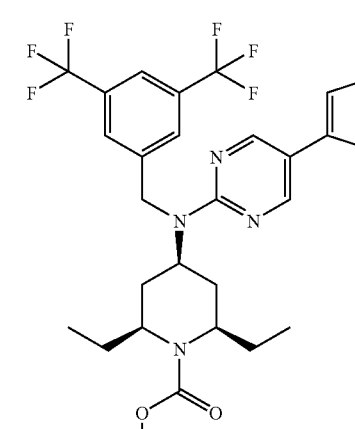 |
| 3 |  | 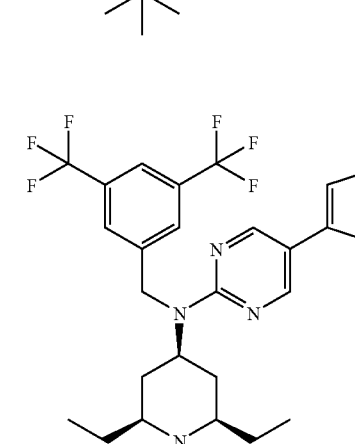 |

-continued
| 4 | 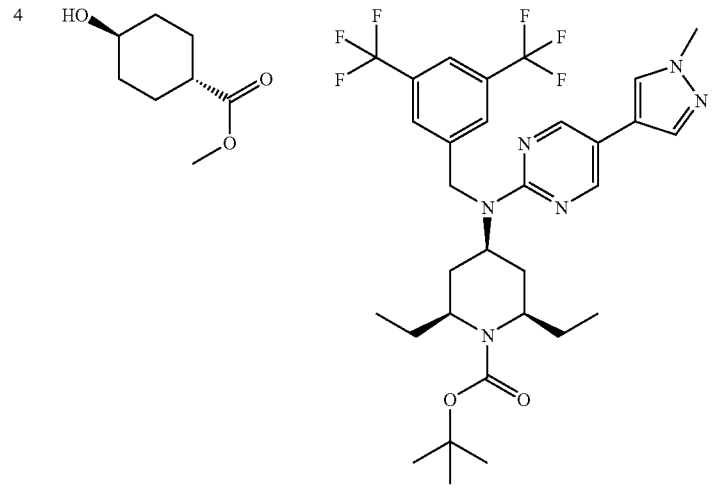 |
| 5 | 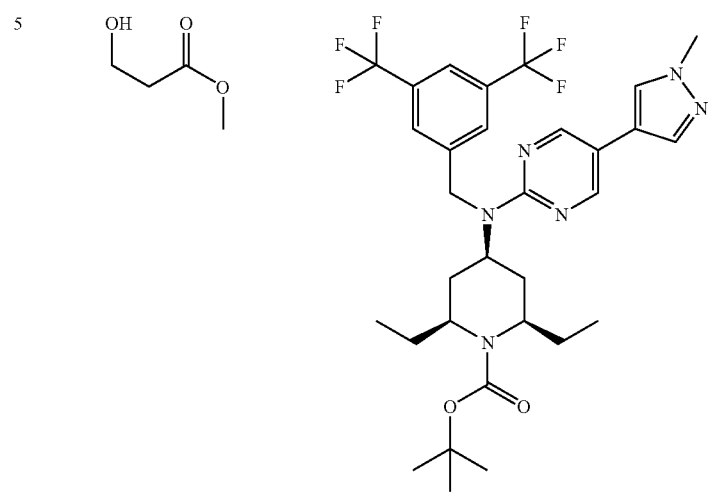 |
| 6 | 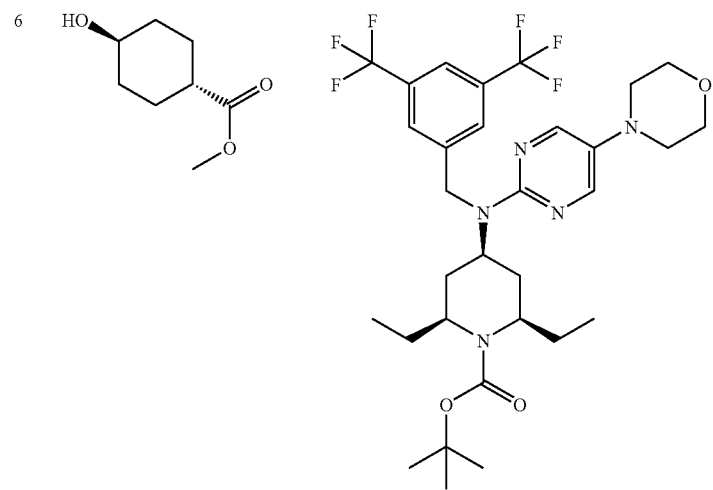 |

-continued
| 7 | 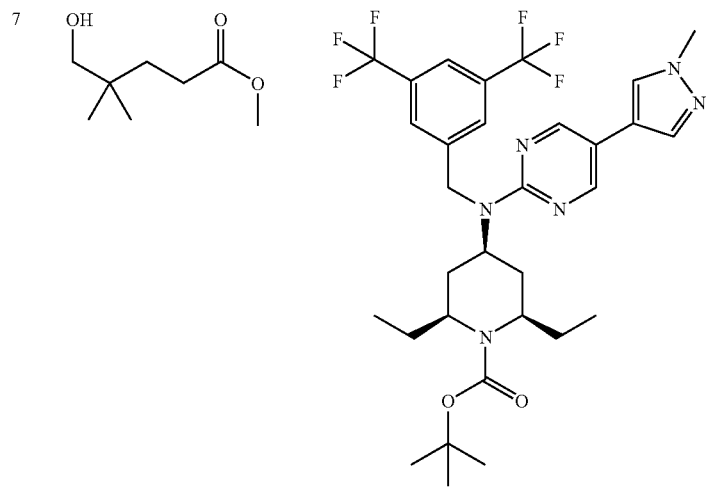 |
| 8 | 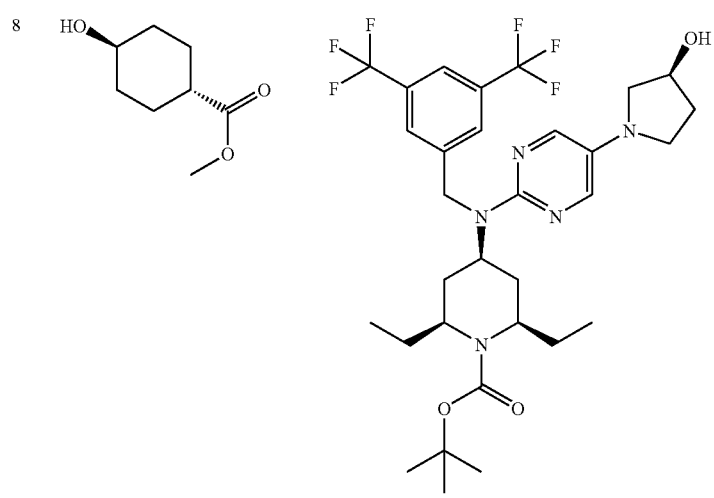 |
| 9 | 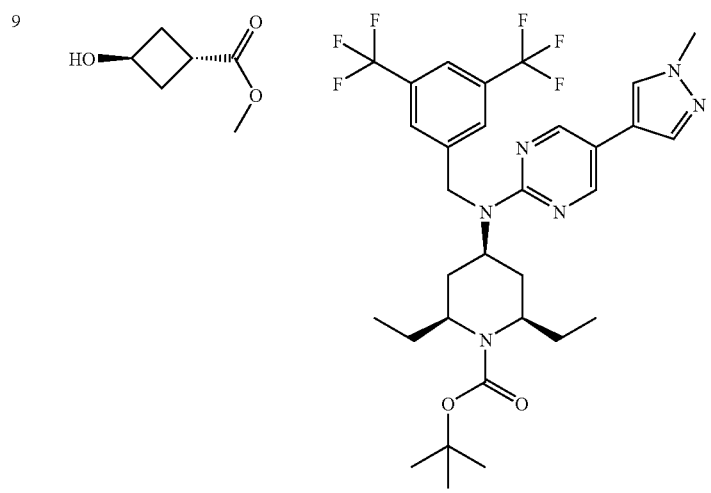 |

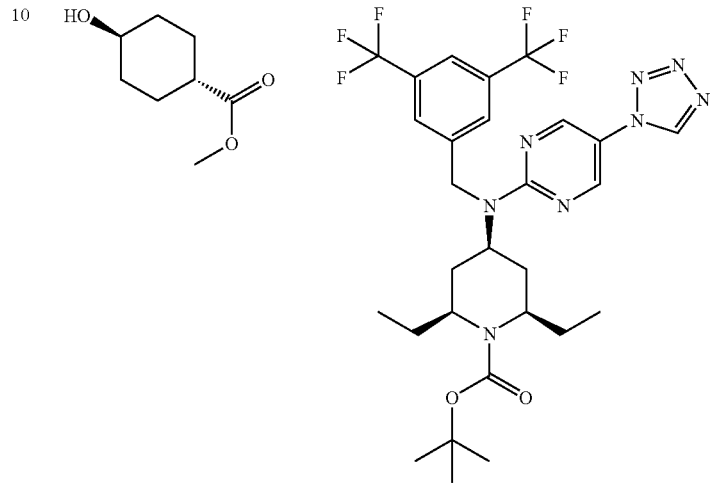
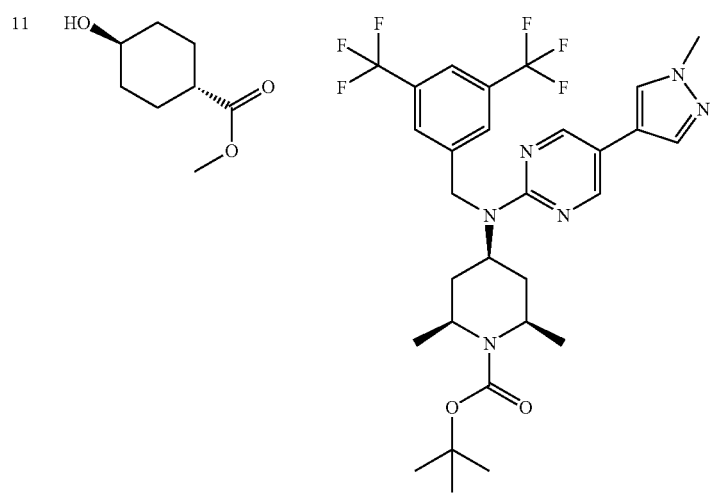
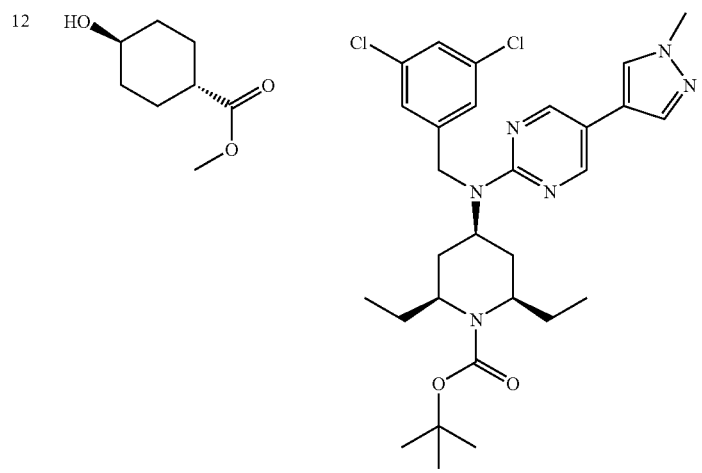

13 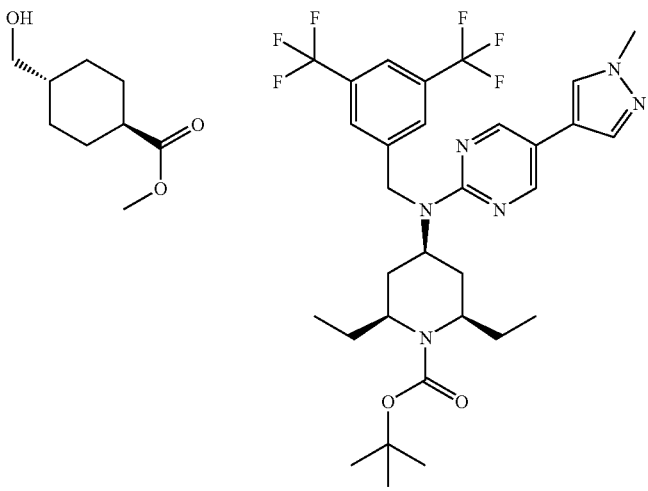
14 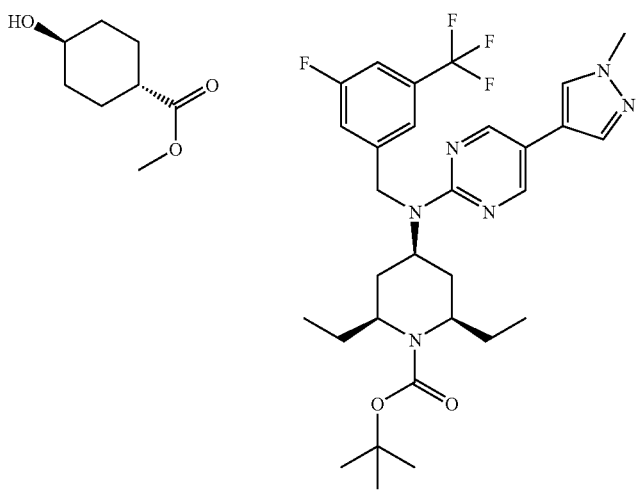
15 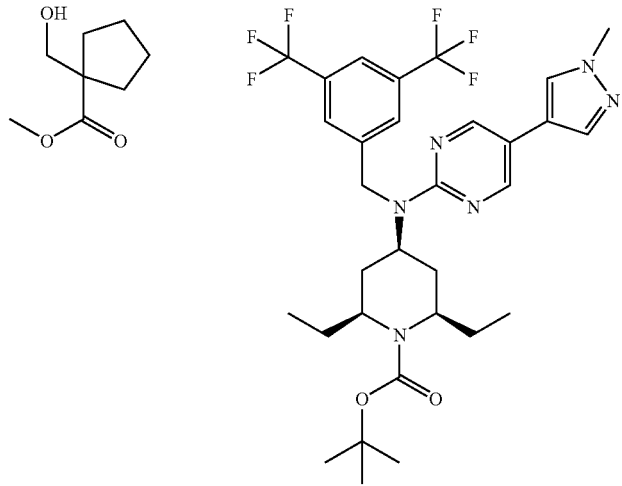

-continued
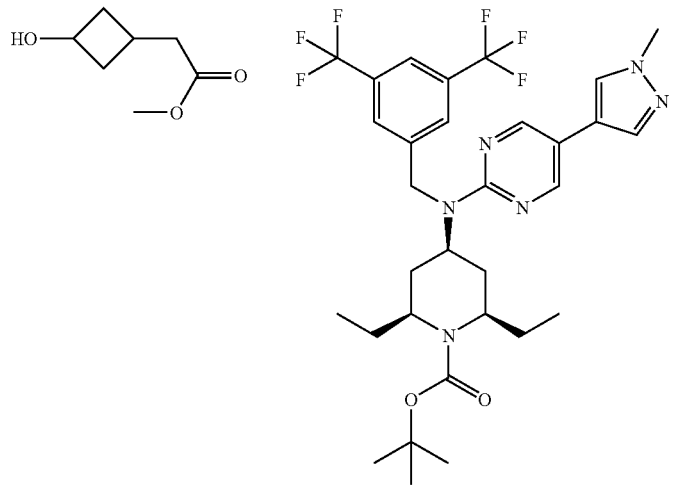
16
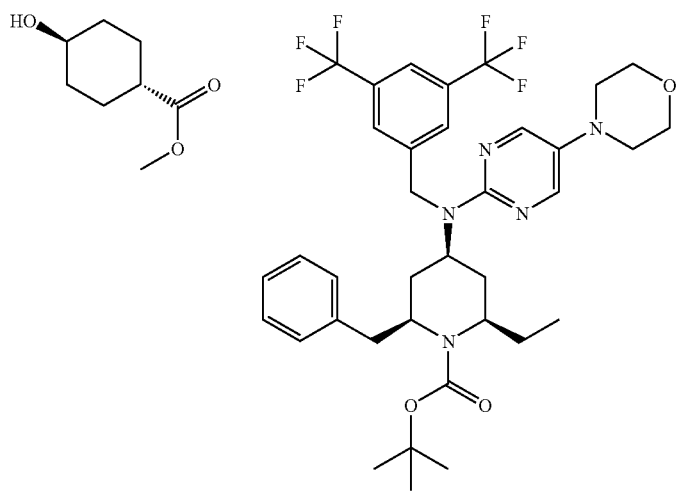
17
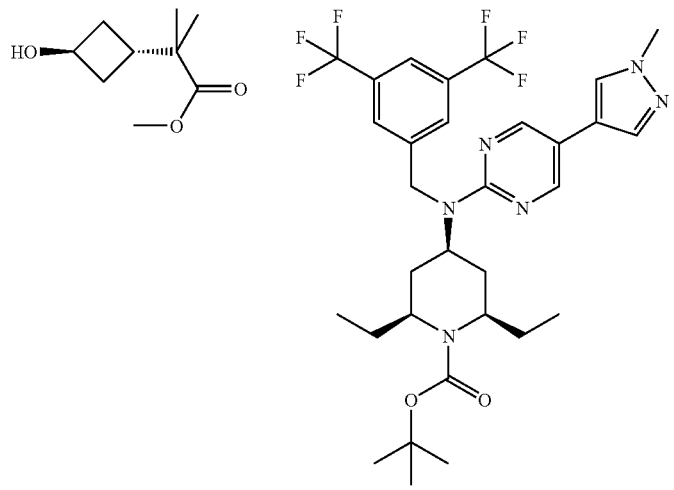
18

| | | |
|---|---|---|
| 19 | 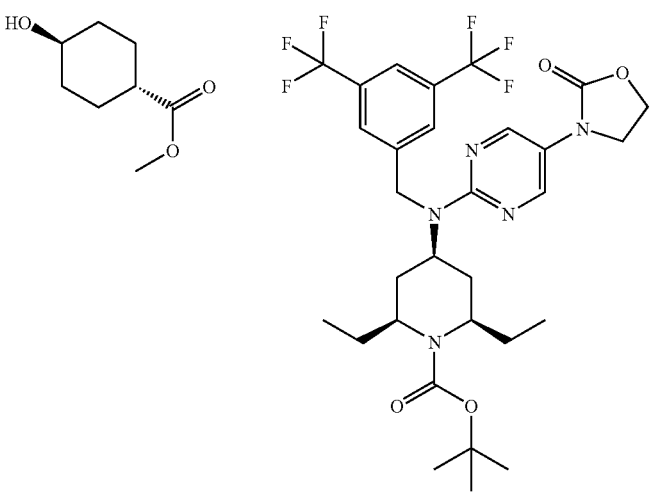 | |
| 20 | 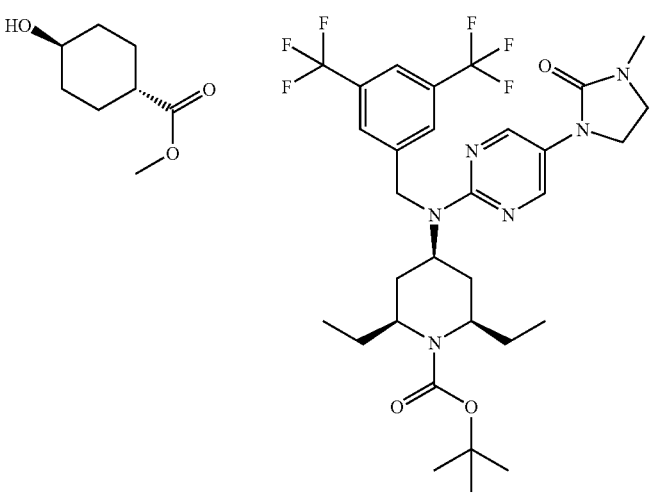 | |
| 21 | 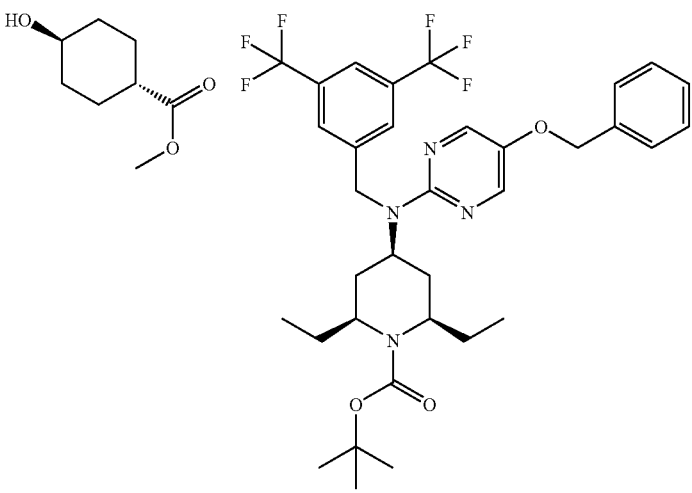 | |

Example 12

1) Synthesis of 2-ethyl-4-oxo-3,4-dihydro-2H-pyridine-1-carboxylic acid tert-butyl ester

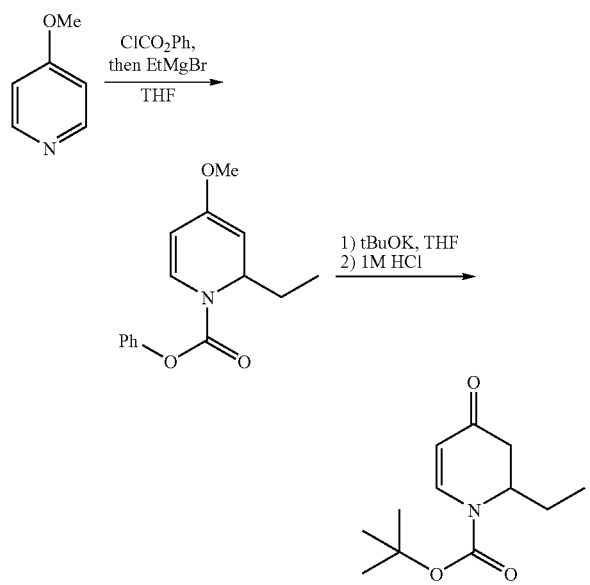

To a solution of 4-methoxypyridine (15.6 g, 143 mmol) in dry THF (1 L) cooled to −35° C. is added ClCO2Ph (22.7 g, 144 mmol). After stirring the slurry for 1 hour, EtMgBr (150 mL, 150 mmol) is added slowly over 30 min. The mixture is warmed to 10° C. over 2 hours then quenched with H2O. The reaction mixture is extracted twice with Et2O (1 L), combined organic layer is dried over Na2SO4, and the solvent is removed under reduced pressure. To a solution of the resultant colorless oil in dry THF (500 mL) at −78° C. is added t-BuOK (64 g, 572 mmol). The reaction mixture is stirred overnight and warmed to room temperature. The reaction mixture is diluted with Et2O, quenched with ice, partitioned, and the organic layer is washed three times with 1.5 N aqueous NaOH and then with brine, dried over MgSO4 and concentrated in reduced pressure to afford 2-ethyl-4-oxo-3,4-dihydro-2H-pyridine-1-carboxylic acid tert-butyl ester as a pale yellow oil (27.8 g, 86% yield); ESI-MS m/z: 226 [M+1]+, Retention time 1.64 min (condition A).

The following material is prepared following the above procedure.

| Name | Structure | Reagent |
|---|---|---|
| 2-Methyl-4-oxo-3,4-dihydro-2H-pyridine-1-carboxylic acid tert-butyl ester | (structure) | MeMgBr instead of EtMgBr |
| 2-Benzyl-4-oxo-3,4-dihydro-2H-pyridine-1-carboxylic acid tert-butyl ester | (structure) | BnMgBr instead of EtMgBr |

2) Synthesis of 2,6-diethyl-4-oxo-piperidine-1-carboxylic acid tert-butyl ester To CuI (0.82 mmol, 156 mg) in a flask purged with N2 is added 1.00 M tetrahydrofuran solution of EtMgBr (0.82 mmol, 0.82 ml) at −78° C. After stirring the suspension for 30 min, BF3.Et2O (0.41 mmol, 57.9 mg) is added and stirred for 10 min at the same temperature. To the suspension is added tetrahydrofuran solution (3.3 mL) of 2-ethyl-4-oxo-3,4-dihydro-2H-pyridine-1-carboxylic acid tert-butyl ester (0.41 mmol, 92.7 mg) at −78° C., then the mixture is allowed to stir for 1.5 hours and then allow to stir at −40° C. for 2 hours. The mixture is warmed to room temperature and quenched with saturated aqueous NH4Cl and extracted with EtOAc. The combined organic layers are washed with brine, dried over MgSO4, filtered, concentrated under reduced pressure, and purified by silica gel column chromatography (eluent: hexane/EtOAc=10/1) and separated the cis and trans isomers of racemic 2,6-diethyl-4-oxo-piperidine-1-carboxylic acid tert-butyl ester (50 mg, 50%); ESI-MS m/z: 200 [M-tBu+2]+, Retention time 3.51 min. (condition A).

The following material is prepared following the above procedure.

| Name | Structure | Starting Material |
|---|---|---|
| 2-Benzyl-6-ethyl-4-oxo-piperidine-1-carboxylic acid tert-butyl ester | 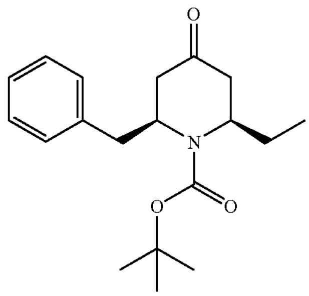 | |
| 2,6-Dimethyl-4-oxo-piperidine-1-carboxylic acid tert-butyl ester | 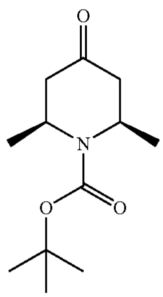 | MeMgBr instead of EtMgBr |
3) Synthesis of cis-4-{(5-bromo-pyrimidin-2-yl)[3,5-bis(trifluoromethylbenzyl)]}amino-2,6-diethyl-piperidine-1-carboxylic acid tert-butyl ester
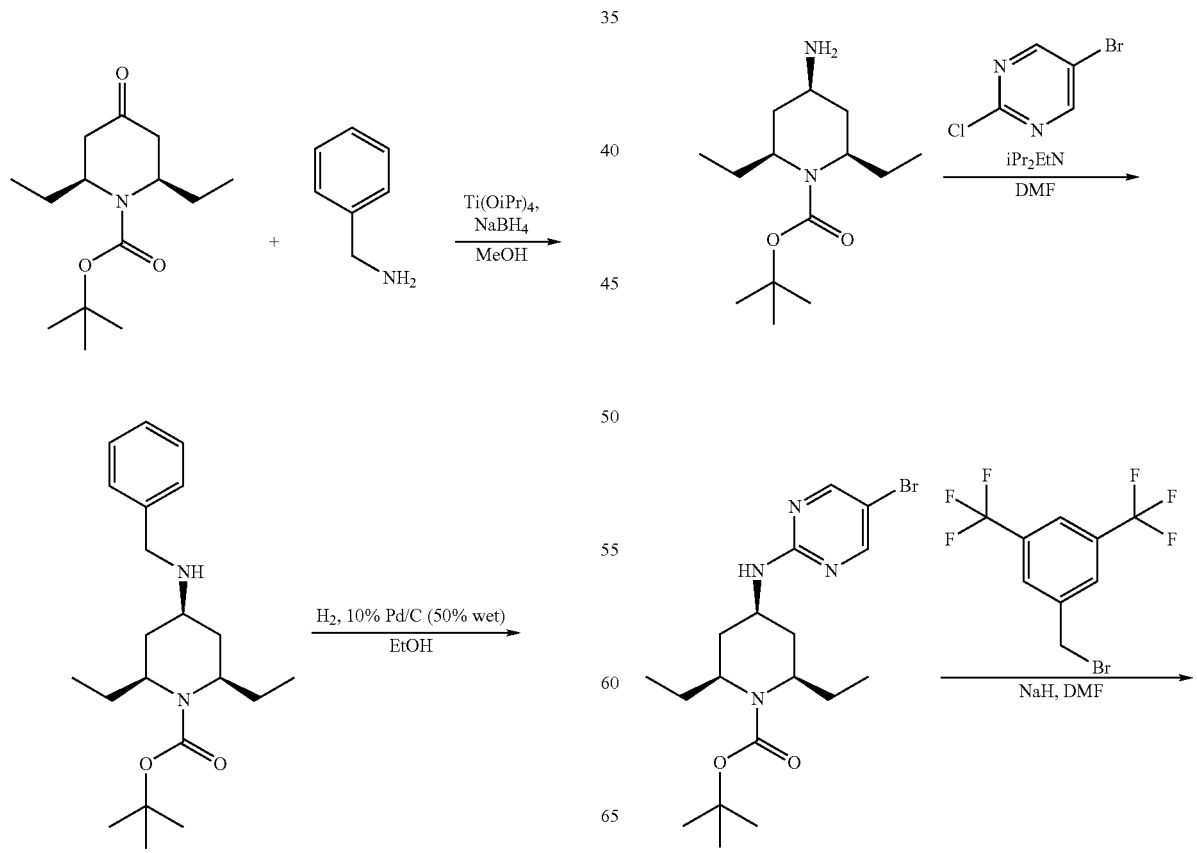
-continued -continued

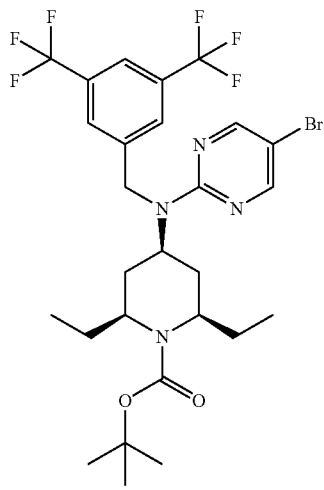

To a mixture of cis-2,6-diethyl-4-oxo-piperidine-1-carboxylic acid tert-butyl ester (11.1 g, 44 mmol) in MeOH (150 mL) is added benzylamine (7.1 mL, 65 mmol) and titanium tetraisopropoxide (26 mL, 87 mmol) at 0° C. The mixture is stirred overnight while warming to room temperature. After addition of sodium tetraborohydride (2.5 g, 65 mmol), the mixture is stirred for additional 1 hour at room temperature. H2O and EtOAc are added to the mixture, and the resulting precipitate is removed by filtration. The filtrate is washed sequentially with saturated aqueous NaHCO3 and brine. The aqueous layer is extracted with EtOAc, and the combined organic layer after dried over MgSO4 are concentrated to obtain cis-4-benzylamino-2,6-diethyl-piperidine-1-carboxylic acid tert-butyl ester as clear oil (13.9 g, 92%) after purification. ESI-MS m/z: 346 [M+1]+, Retention time 1.80 min (condition A). cis-4-Benzylamino-2,6-diethyl-piperidine-1-carboxylic acid tert-butyl ester (4.0 g, 11.4 mmol) is dissolved in EtOH (80 mL). In presence of 10% Pd/C (400 mg), the reaction mixture is stirred for 5 hours at 55° C. under hydrogen. After removal of the catalyst, solvent is evaporated to obtain cis-4-amino-2,6-diethyl-piperidine-1-carboxylic acid tert-butyl ester as clear oil (2.9 g, 99%) which is used for next step without further purification. ESI-MS m/z: 256 [M+1]+, Retention time 1.61 min (condition A).

A mixture of cis-4-amino-2,6-diethyl-piperidine-1-carboxylic acid tert-butyl ester (7.29 mmol, 1.87 g), 5-bromo-2-chloropyrimidine (8.02 mmol, 1.55 g), i-Pr2NEt (14.0 mmol, 2.54 mL) and DMF (20 mL) is stirred at 120° C. for 4 hours. After cooling to room temperature, the mixture is diluted with EtOAc and washed with H2O and brine. The organic layer is dried over Na2SO4 and concentrated. The resulting solid is recrystallized from i-Pr2O and n-hexane to give cis-4-(5-bromo-pyrimidin-2-ylamino)-2,6-diethylpiperidine-1-carboxylic acid tert-butyl ester as white solid; ESI-MS m/z: 414 [M+1]+, Retention time 2.29 min. (condition A).

To a solution of cis-4-(5-bromo-pyrimidin-2-ylamino)-2,6-diethylpiperidine-1-carboxylic acid tert-butyl ester (14.6 mmol, 6.05 g) in DMF (60 mL) is added NaH (60% in oil, 17.6 mmol, 0.70 g) at 0° C. After stirring for 1 hour, 3,5-bis(trifluoromethyl)benzyl bromide (17.6 mmol, 3.23 mL) is added, and the reaction mixture is warmed to room temperature. After stirring for 20 minutes, the reaction is quenched with H2O at 0° C. The mixture is extracted with EtOAc, washed with brine, dried over Na2SO4 and concentrated. The obtained residue is purified by silica gel column chromatography to give 4-{(5-bromo-pyrimidin-2-yl)[3,5-bis(trifluoromethyl)benzyl]}amino-2,6-diethylpiperidine-1-carboxylic acid tert-butyl ester (8.02 g, 86%) as yellow oil; ESI-MS m/z: 639[M+]+, Retention time 6.27 min. (condition B).

| Product | ESI-MS m/z [M + 1]+ | Retention time (min) | Starting Material |
|---|---|---|---|
|  | 701 | 5.84 (Condition B) |  |

| Product | ESI-MS m/z [M + 1]+ | Retention time (min) | Starting Material |
|---|---|---|---|
| 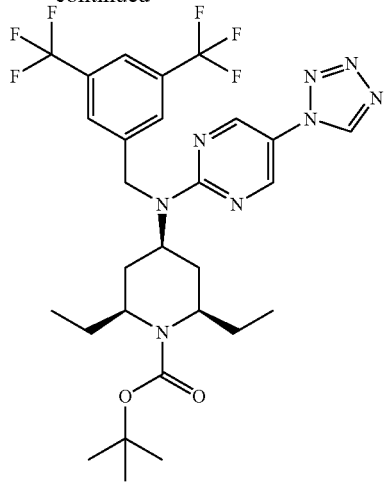 | 611 | 5.50 (Condition C) | |

Example 13

Synthesis of cis-4-[(3,5-bis(trifluoromethyl)benzyl)-(5-tetrazol-1-yl-pyrimidin-2-yl)-amino]-2,6-diethylpiperidine-1-carboxylic acid tert-butyl ester

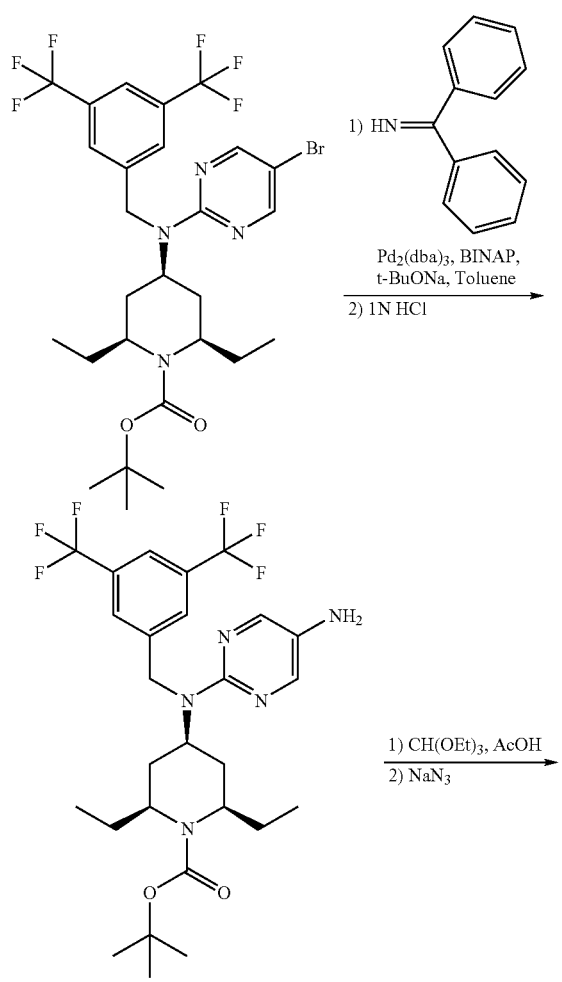

A round-bottom flask is charged with Pd2(dba)3 (17 mg, 0.019 mmol) and BINAP (35 mg, 0.057 mg) and purged with nitrogen. To the flask is added 4-[(3,5-bis(trifluoromethyl)benzyl)-(5-bromo-pyrimidin-2-yl)-amino]-2,6-diethylpiperidine-1-carboxylic acid tert-butyl ester (120 mg, 0.19 mmol), benzophenone imine (38 uL, 0.23 mmol), sodium tert-butoxide (27 mg, 0.29 mmol) and toluene (2 mL), and the mixture is heated to 110° C. for 3 hours. The mixture is cooled to room temperature, diluted with Et2O, filtered, and concentrated to give brown oil which is used for next step without further purification.

To a solution of the imine adduct in THF (1 mL) is added aqueous 2M HCl (1 mL). After stirred for 30 minutes, the mixture is basified with aqueous 2M NaOH. The mixture is extracted with $CH_2Cl_2$, dried over anhydrous Na2SO4 and concentrated under reduced pressure. The obtained residue is purified silica gel column chromatography to give cis-4-[(5-amino-pyrimidin-2-yl)-(3,5-bis(trifluoromethyl)benzyl)-amino]-2,6-diethylpiperidine-1-carboxylic acid tert-butyl ester (69 mg, 0.12 mmol, 60%).

To cis-4-[(5-amino-pyrimidin-2-yl)-(3,5-bis(trifluoromethyl)benzyl)-amino]-2,6-diethylpiperidine-1-carboxylic acid tert-butyl ester in acetic acid (1 mL) is added triethyl orthoformate (30 uL, 0.18 mmol) under nitrogen, and the mixture is heated at 75° C. After stirred for 30 min at 75° C., NaN3 (24 mg, 0.21 mmol) is added and stirred for 3 hours. The mixture is basified with saturated NaHCO3 and extracted with EtOAc, dried over Na2SO4, purified by silica gel chromatography to give 23 mg (0.06 mmol, 52%) cis-4-[(3,5-bis(trifluoromethyl)benzyl)-(5-tetrazol-1-yl-pyrimidin-2-yl)-amino]-2,6-diethylpiperidine-1-carboxylic acid tert-butyl ester.

Example 14

1) Synthesis of 2-chloro-5-(4,4,5,5-tetramethyl-[1,3,2]dioxaborolan-2-yl)-pyrimidine

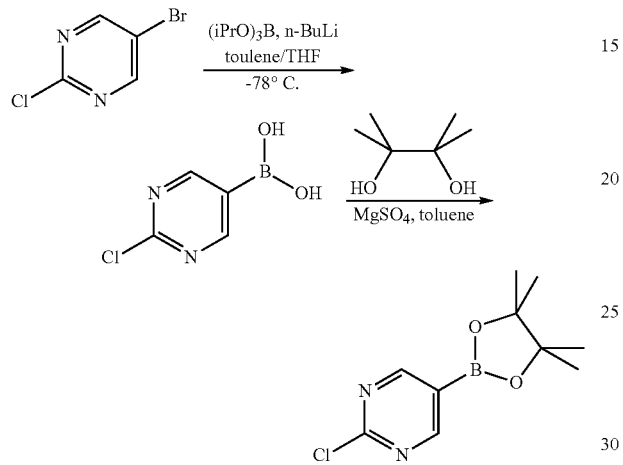

To a solution of 5-bromo-2-chloro-pyrimidine (10 mmol, 1.93 g) and triisopropyl borate (12 mmol, 2.8 mL) in toluene (16 mL) and THF (4 mL) is added n-butyl lithium in hexane (1.58 M, 12 mmol, 7.6 mL) dropwise at −78° C. over 45 min and stirred at −78° C. for 1 hour. The mixture is warmed to −20° C., then added aqueous 1M HCl (20 mL). The mixture is warmed to room temperature. The precipitate is collected and washed with hexane to give a colorless powder (808 mg, 51%). A mixture of the powder (3.63 mmol, 575 mg), pinacol (3.81 mmol, 450 mg) and MgSO4 (18.15 mmol, 2.2 g) in toluene (10 mL) is stirred at room temperature for 15 hour. The mixture is filtrated and the solution is concentrated under reduced pressure. The resultant solid is washed with water to give 2-chloro-5-(4,4,5,5-tetramethyl-[1,3,2]dioxaborolan-2-yl)-pyrimidine (875 mg, quant); ESI-MS m/z: 159 [M+1-pinacol]+, Retention time 1.75 min (condition A).

2) Synthesis of cis-4-[(5-Benzyloxy-pyrimidin-2-yl)-(3,5-bis(trifluoromethyl)benzyl)-amino]-2,6-diethylpiperidine-1-carboxylic acid 4-methoxycarbonyl-cyclohexyl ester

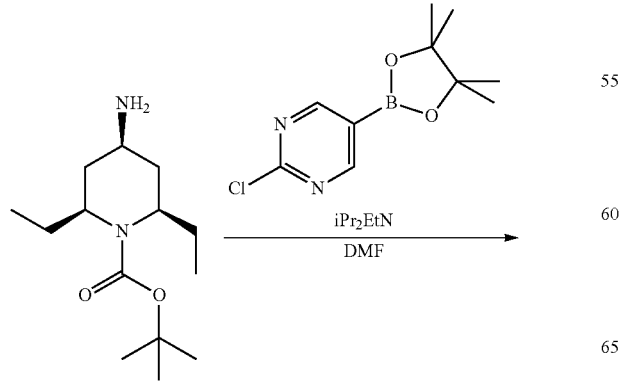

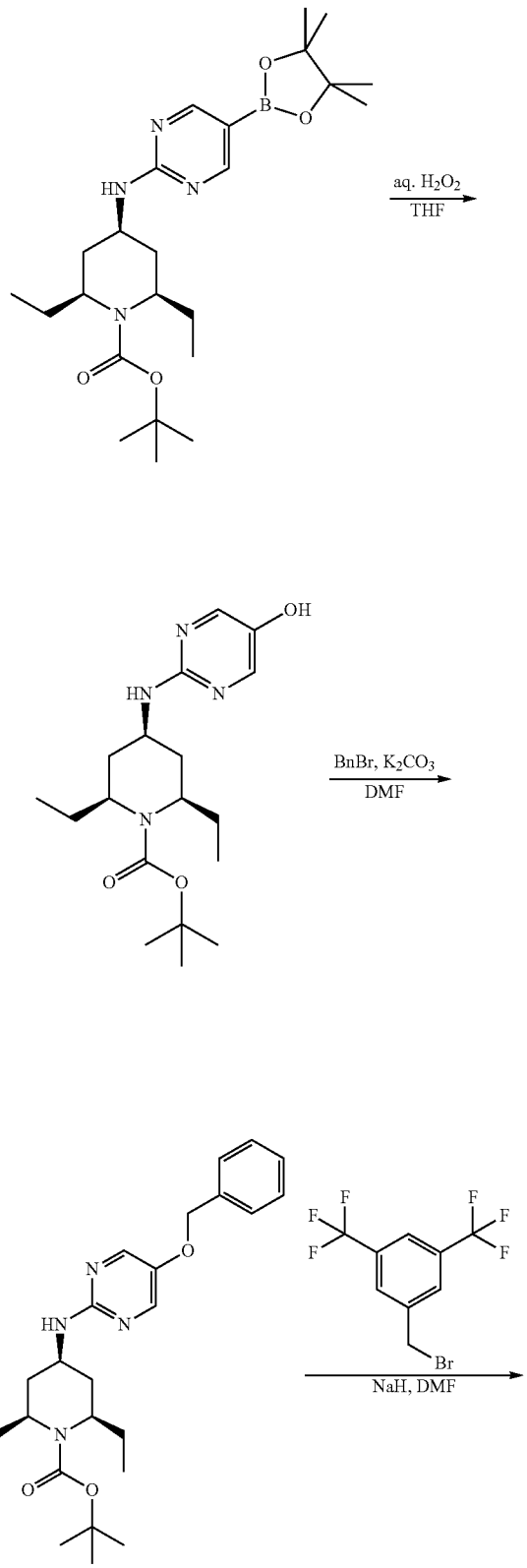

-continued

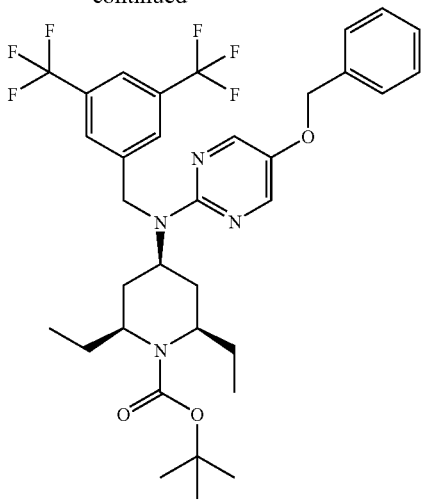

A solution of 4-amino-2,6-diethylpiperidine-1-carboxylic acid tert-butyl ester (3.9 mmol, 1 g), 2-chloro-5-(4,4,5,5-tetramethyl-[1,3,2]dioxaborolan-2-yl)-pyrimidine (4.7 mmol, 1.1 g) and N,N-diisopropylethylamine (5.9 mmol, 1.1 mL) in DMF (12 ml) is allowed to warm to 120° C. and stirred for 3 hours. The mixture is cooled to room temperature and then water is added. The mixture is extracted with EtOAc. The combined organic layer is dried over Na2SO4, filtrated, and concentrated under reduced pressure.

The obtained residue is dissolved in THF (15 mL) and added aqueous H2O2 (35%, 1.14 mL) at room temperature. The mixture is stirred at room temperature for 2 hours. The mixture is cooled until 0° C. and quenched with saturated aqueous sodium thiosulfate. The mixture is extracted with EtOAc, and the combined organic layer is dried over Na2SO4, filtrated, and concentrated under reduced pressure. The obtained residue is purified by silica gel column chromatography (eluent: hexane/EtOAc) to give 2,6-diethyl-4-(5-hydroxy-pyrimidin-2-ylamino)-piperidine-1-carboxylic acid tert-butyl ester (1.12 g, 83%); ESI-MS m/z: 351 [M+1]+, Retention time 1.75 min (condition A).

To a mixture of 2,6-diethyl-4-(5-hydroxy-pyrimidin-2-ylamino)-piperidine-1-carboxylic acid tert-butyl ester (1.72 mmol, 580 mg) and potassium carbonate (3.23 mmol, 1.12 g) in DMF (12 mL) is added benzylamine (3.53 mmol, 0.42 mL) at room temperature and stirred for 2 hours. Water is added to the mixture, and the precipitate is collected and washed with hexane to give 4-(5-benzyloxy-pyrimidin-2-ylamino)-2,6-diethylpiperidine-1-carboxylic acid isopropyl ester (1.26 g, 74%) as a colorless solid. To a solution of 4-(5-benzyloxy-pyrimidin-2-ylamino)-2,6-diethylpiperidine-1-carboxylic acid isopropyl ester (2.86 mmol, 1.26 g) in DMF (28 mL) is added sodium hydride (60% oil suspension, 5.72 mmol, 230 mg) at 0° C. and stirred at room temperature for 20 min. To the mixture is added 1-bromomethyl-3,5-bis(trifluoromethyl) benzene (4.29 mmol, 0.79 mL) at 0° C. and stirred at room temperature for 17 hours. To the mixture is added sodium hydride (60% oil suspension, 2.86 mmol, 115 mg) and 1-bromomethyl-3,5-bis(trifluoromethyl)benzene (2.73 mmol, 0.5 mL) at 0° C. and stirred at room temperature for 5 hours. To the mixture is added water, and extracted with EtOAc. The combined organic layer is dried over Na2SO4, filtrated, and concentrated under reduced pressure. The obtained residue is purified by silica gel column chromatography (eluent: n-hexane/EtOAc) to give cis-4-[(5-benzyloxy-pyrimidin-2-yl)-(3,5-bis(trifluoromethyl)benzyl)-amino]-2,6-diethylpiperidine-1-carboxylic acid 4-methoxycarbonyl-cyclohexyl ester (880 mg, 46%); ESI-MS m/z: 667 [M+1]+, Retention time 2.69 min (condition A).

3) Synthesis of cis-4-[[5-(2-Acetoxy-ethoxy]-pyrimidin-2-yl)-(3,5-bis(trifluoromethyl)benzyl)-amino]-2,6-diethyl-piperidine-1-carboxylic acid trans-4-methoxycarbonyl-cyclohexyl ester

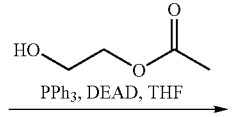

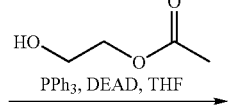

133
-continued

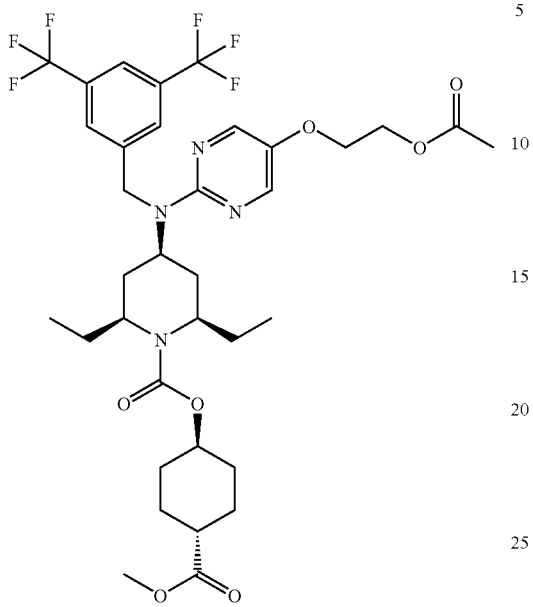

cis-4-[(5-Benzyloxy-pyrimidin-2-yl)-(3,5-bis(trifluoromethyl)benzyl)-amino]-2,6-diethylpiperidine-1-carboxylic acid trans-4-methoxycarbonyl-cyclohexyl ester (0.72 mmol, 540 mg) and 10% Pd/C in MeOH is hydrogenated for 30 min. The solution is concentrated under reduced pressure. The obtained residue is purified by silica gel column chromatography (eluent: hexane/EtOAc) to give cis-4-[[5-(2-acetoxy-ethoxy)-pyrimidin-2-yl]-(3,5-bis(trifluoromethyl)benzyl)-amino]-2,6-diethylpiperidine-1-carboxylic acid trans-4-methoxycarbonyl-cyclohexyl ester (335 mg, 70%); ESI-MS m/z: 661 [M+1]+, Retention time 2.39 min (condition A).

To a mixture of cis-4-[[5-(2-acetoxy-ethoxy]-pyrimidin-2-yl]-(3,5-bistrifluoromethyl)benzyl)-amino]-2,6-diethylpiperidine-1-carboxylic acid trans-4-methoxycarbonyl-cyclohexyl ester (0.15 mmol, 100 mg), acetic acid 2-hydroxy-ethyl ester (0.225 mmol, 21 uL) and triphenylphosphine (0.225 mmol, 59 mg) in THF (0.75 mL) is added DEAD (0.225 mmol, 33 uL) at room temperature and then stirred for 15 hours. To the mixture is added water, and extracted with CH2Cl2. The combined organic layer is dried over Na2SO4, filtrated, and concentrated under reduced pressure. The obtained residue is purified by silica gel column chromatography (eluent: hexane/EtOAc) to give 4-[[5-(2-acetoxy-ethoxy)-pyrimidin-2-yl]-(3,5-bis(trifluoromethyl)benzyl)-amino]-2,6-diethylpiperidine-1-carboxylic acid trans-4-methoxycarbonyl-cyclohexyl ester (45 mg, 40%); ESI-MS m/z: 747 [M+1]+, Retention time 2.54 min (condition A).

134
Example 15

Synthesis of cis-4-{[4-(1-Methylpyrazole-4-yl)pyrimidin-2-yl](3,5-dichlorobenzyl)amino}-2,6-diethylpiperidine-1-carboxylic acid tert-butyl ester

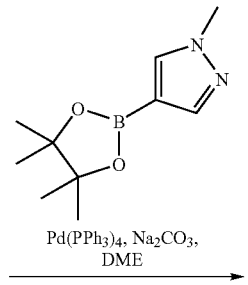

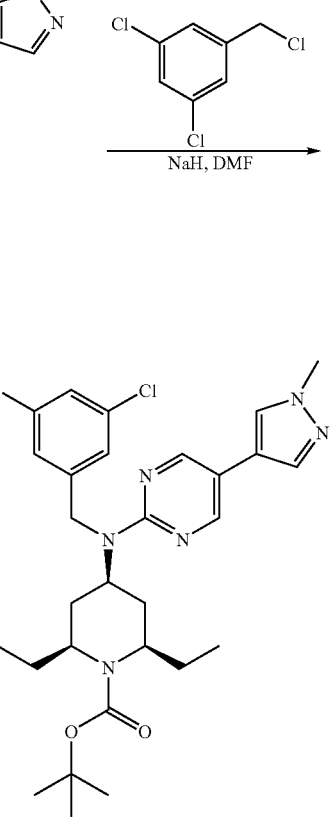

A mixture of cis-4-(5-bromo-pyrimidin-2-ylamino)-2,6-diethyl-piperidine-1-carboxylic acid tert-butyl ester (2.42 mmol, 1.00 g), 1-methyl-pyrazole-4-boronic acid pinacol ester (3.14 mmol, 654 mg), tetrakis(triphenylphosphine)palladium (0.242 mmol, 280 mg), sodium carbonate (3.63 mmol, 385 mg), H2O (1.9 mL) and DME (10 mL) is stirred under N2 atmosphere at 90° C. After stirring for 6 hours, the mixture is cooled to room temperature and diluted with EtOAc. The resulting mixture is washed with H2O and brine, dried over Na2SO4 and concentrated. The obtained residue is purified by flash silica gel column chromatography (eluent; MeOH/ dichloromethane=1/8) and the resulting solid is recrystallized from i-Pr2O and n-hexane to give cis-2,6-diethyl-4-[5-(1-methyl-1H-pyrazol-4-yl)-pyrimidin-2-ylamino]-piperidine-1-carboxylic acid tert-butyl ester (793 mg, 79%) as white solid; ESI-MS m/z: 415 [M+1]+, Retention time 3.12 min. (condition A).

To a solution of NaH (60% in mineral oil, 0.022 g, 0.55 mmol) in dry DMF (1 mL) cooled to 0° C. is added cis-4-[4-(1-methylpyrazole-4-yl)pyrimidin-2-yl]-2,6-diethylpiperidine-1-carboxylic acid tert-butyl ester (0.15 g, 0.36 mmol). After stirring the resulting solution at room temperature for 30 minutes, 3,5-dichlorobenzylchloride (0.13 g, 0.54 mmol) is added, and the resulting mixture is stirred for 2 hours. The mixture is quenched with 1M HCl, then extracted twice with ethyl acetate. The combined organic layer is washed with brine, dried over MgSO4, filtered, concentrated under reduced pressure. The obtained residue is purified by silica gel column chromatography to afford cis-4-{[4-(1-methylpyrazole-4-yl)pyrimidin-2-yl](3,5-dichlorobenzyl)amino}-2,6-diethylpiperidine-1-carboxylic acid tert-butyl ester (0.10 g, 48%). 1H-NMR (400 MHz, CDCl3): 0.85 (t, 6H), 1.40-1.55 (m, 4H), 1.48 (s, 9H), 1.75-1.83 (m, 2H), 2.10-2.19 (m, 2H), 3.95 (s, 3H), 4.07-4.14 (m, 2H), 4.73 (s, 2H), 4.73-4.83 (m, 1H), 7.12 (d, 2H), 7.22 (t, 1H), 7.53 (s, 1H), 7.66 (s, 1H), 8.43 (s, 2H).

The following compounds are prepared following the procedure of Example 15 filtered through a silica gel short column (eluent: diethyl ether). Collected filtrate is concentrated under reduced pressure to give 5-hydroxy-pentanoic acid methyl ester; 1H NMR (400 MHz, chloroform-d) ppm 1.57-1.76 (m, 4H), 2.35 (m, 2H), 3.65 (m, 5H).

2) Synthesis of cis-4-Hydroxy-cyclohexanecarboxylic acid methyl ester

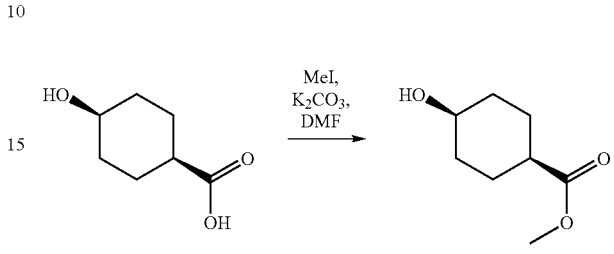

To a solution of trans-4-hydroxycyclohexanecarboxylic acid (5.0 mmol, 721 mg), K2CO3 (15.0 mmol, 2.07 g) in DMF (17 mL) is added iodomethane (6.0 mmol, 0.374 mL). After stirring for 2 h, the mixture is diluted with EtOAc. The mixture is washed with H2O and brine, dried over Na2SO4 and concentrated. The residue is used to next reaction without

| NO. | Product | ESI-MS m/z [M + 1]+ | Retention time (min) | Starting Material |
|---|---|---|---|---|
| 1 | (structure shown) | 591 | 2.39 (condition B). | (structure shown) |

Example 16

Preparation of Alcohol

1) Synthesis of 5-hydroxy-pentanoic acid methyl ester

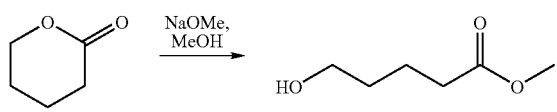

To a solution of sodium methoxide (71.3 mg, 1.32 mmol) in anhydrous MeOH (4 ml), tetrahydro-pyran-2-one (1.32 g, 13.2 mmol) is added dropwise at room temperature under nitrogen. The mixture is stirred at 50° C. for 4 hours and further purification (643 mg, 81%); ESI-MS m/z: 159 [M+1]+, Retention time 1.34 min. (condition A).

3) Synthesis of trans-4-Hydroxy-cyclohexanecarboxylic acid methyl ester

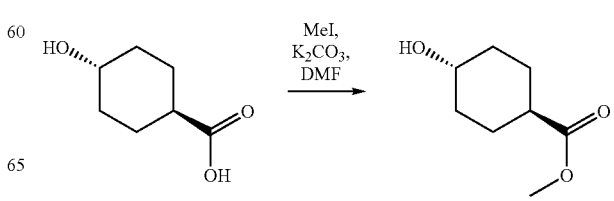

To a solution of trans-4-hydroxycyclohexanecarboxylic acid (14.7 mmol, 2.12 g), K2CO3 (17.6 mmol, 2.44 g) in DMF (15 mL) is added iodomethane (17.6 mmol, 1.10 mL). After stirring for 2 hours, the mixture is diluted with EtOAc. The mixture is washed with H2O and brine, dried over Na2SO4 and concentrated. The obtained residue is used to next reaction without further purification (1.62 g, 70%); 1H-NMR (400 MHz, CDCl$_3$): 1.24-1.33 (m, 2H), 1.45-1.53 (m, 2H), 1.98-2.28 (m, 4H), 2.21-2.29 (m, 1H), 3.57-3.64 (m, 1H), 3.67 (s, 3H).

4) Synthesis of 5-hydroxy-4,4-dimethyl-pentanoic acid methyl ester

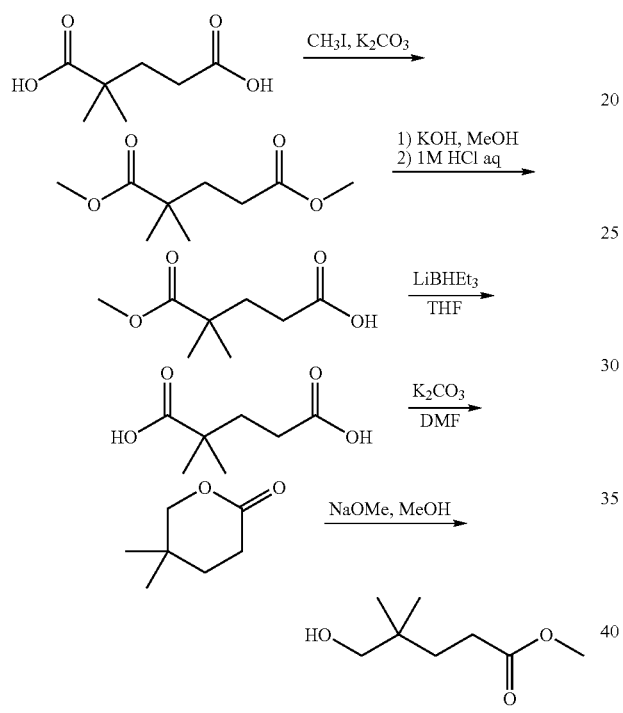

To a solution of 2,2-dimethyl-pentanedioic acid (3.0 g, 19 mmol) is added K2CO3 (6.49 g, 47 mmol) and iodomethane (2.5 ml, 39 mmol) at room temperature. The mixture is stirred at room temperature for 18 hours. To the mixture, H2O is added and the solution is extracted with AcOEt. The organic layer is washed with H2O, saturated aqueous NaHCO3 and brine, and dried over MgSO4. Solvent is removed under reduced pressure to give 2,2-dimethyl-pentanedioic acid dimethyl ester (2.49 g, 70%); TLC (hexane/AcOEt, 3:1) Rf 0.50, 1H NMR (400 MHz, chloroform-d) δ ppm 1.19 (s, 6H), 1.88 (m, 2H), 2.29 (m, 2H), 3.67 (s, 6H).

To a solution of 2,2-dimethyl-pentanedioic acid dimethyl ester (2.40 g, 12.8 mmol) in MeOH (15 ml) is added potassium hydroxide (0.788 g, 14.0 mmol). The mixture is stirred at room temperature for 16 hours and refluxed for 2 hours. The mixture is cooled to room temperature and concentrated under reduced pressure. To the obtained residue, 1M aqueous HCl (14 ml) is added and the solution is extracted with ether. The organic layer is washed with H2O, dried over Na2SO4, and concentrated under reduced pressure to give 2,2-dimethyl-pentanedioic acid 1-methyl ester (1.97 g, 88%); $^1$H NMR (400 MHz, chloroform-d) ppm 1.20 (s, 6H), 1.87-1.91 (m, 2H), 2.32-2.36 (m, 2H), 3.67 (s, 3H).

To a suspension of 2,2-dimethyl-pentanedioic acid 1-methyl ester (1.00 g, 5.75 mmol) in THF (3 mL), 1M LiBHEt3 in THF (38.0 ml, 38.0 mmol) is added dropwise maintaining the temperature below 10° C. under nitrogen. The mixture is stirred at 10° C. for 1 hour. To the mixture, 50% AcOH (4.6 mL) and H2O are added. The solution is extracted with AcOEt, and the organic layer is washed with H2O, dried over MgSO4, and concentrated under reduced pressure to give 5-hydroxy-4,4-dimethyl-pentanoic acid (850 mg, quant.); $^1$H NMR (400 MHz, chloroform-d) ppm 1.06 (s, 6H), 1.70 (t, 2H), 2.56 (t, 2H), 3.98 (s, 2H).

To a solution of 5-hydroxy-4,4-dimethyl-pentanoic acid (300 mg, 2.05 mmol) in DMF (5 ml), K2CO3 (369 mg, 2.87 mmol) and iodomethane (154 ul, 2.47 mmol) are added at room temperature. The mixture is stirred at room temperature for 15 hours. To the mixture, H2O is added and the solution is extracted with AcOEt. The organic layer is washed with H2O, and brine, and dried over MgSO4, and concentrated under reduced pressure. The residue is purified by silica gel column chromatography to give 5,5-dimethyl-tetrahydro-pyran-2-one (150 mg, 47%); TLC (hexane/AcOEt, 2:1) Rf 0.40, $^1$H NMR (400 MHz, chloroform-d) δ ppm 1.06 (s, 6H), 1.70 (t, 2H), 2.56 (t, 2H), 3.97 (s, 2H).

To a solution of sodium methoxide (6.32 mg, 0.117 mmol) in anhydrous MeOH (346 mL), 5,5-dimethyl-tetrahydro-pyran-2-one (150 mg, 1.17 mmol) is added dropwise at room temperature under nitrogen. The mixture is stirred at 50° C. for 4 hours and filtered through a silica gel short column (eluent: diethyl ether). The filtrate is concentrated under reduced pressure to give 5-hydroxy-4,4-dimethyl-pentanoic acid methyl ester (175 mg, 93%); TLC (hexane/AcOEt, 2:1) Rf 0.27, $^1$H NMR (400 MHz, chloroform-d) δ ppm 0.89 (s, 6H), 1.63 (m, 2H), 2.32 (m, 2H), 3.28 (d, 2H), 3.68 (s, 3H).

5) Synthesis of trans-3-hydroxy-cyclobutanecarboxylic acid methyl ester

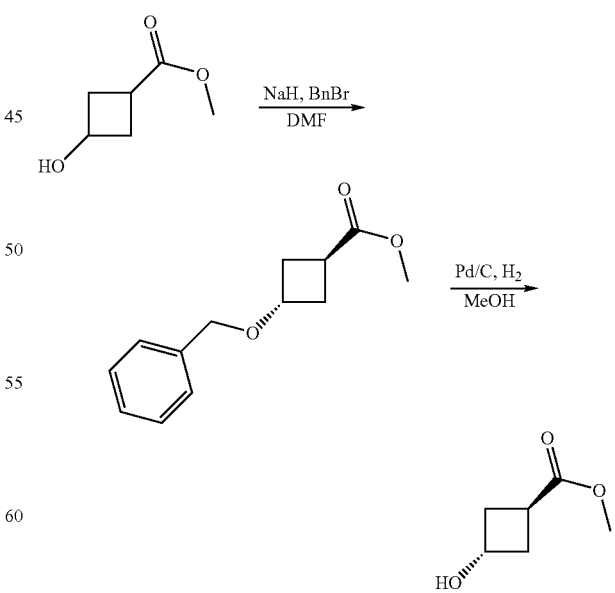

To a solution of cis-trans mixture of 3-hydroxy-cyclobutanecarboxylic acid methyl ester (1.30 g, 10 mmol) in DMF 13 mL, NaH (50% in oil, 720 mg, 15 mmol) is added at 0° C.

After stirring at 0° C. for 15 minutes, benzyl bromide (1.43 ml, 12 mmol) is added at 0° C. The mixture is stirred at room temperature for 2 hours and quenched with H2O. The solution is extracted with AcOEt. The organic layer is washed with H2O and brine, dried over MgSO4 and concentrated under reduced pressure. The residue is purified by silica gel column chromatography to give trans-3-benzyloxy-cyclobutanecarboxylic acid methyl ester (340 mg, 15.4%); TLC (hexane/AcOEt, 5:1) Rf 0.40, $^1$H NMR (400 MHz, chloroform-d) δ ppm 2.26-2.34 (m, 2H), 2.48-2.52 (m, 2H), 3.02-3.06 (m, 1H), 3.69 (s, 3H), 4.26-4.33 (m, 1H), 4.42 (s, 2H), 7.27-7.35 (m, 5H).

A solution of trans-3-benzyloxy-cyclobutanecarboxylic acid methyl ester (680 mg, 3.09 mmol) as a 0.05 M solution in MeOH is pumped through the H-Cube™ flow hydrogenator fitted with a 10 mol % Pd/C catalyst cartridge heated to 40° C. at 10 bar. The flow rate is set at 1 ml/min. The solvent is removed under reduced pressure to give trans 3-hydroxy-cyclobutanecarboxylic acid methyl ester (380 mg, 94.5%); TLC (hexane/AcOEt, 1:1) Rf 0.38, 1H NMR (400 MHz, chloroform-d) δ ppm 2.18-2.25 (m, 2H), 2.55-2.61 (m, 2H), 3.01-3.08 (m, 1H), 3.70 (s, 3H), 4.53-4.61 (m, 1H).

6) Synthesis of cis-4-Hydroxymethyl-cyclohexanecarboxylic acid methyl ester

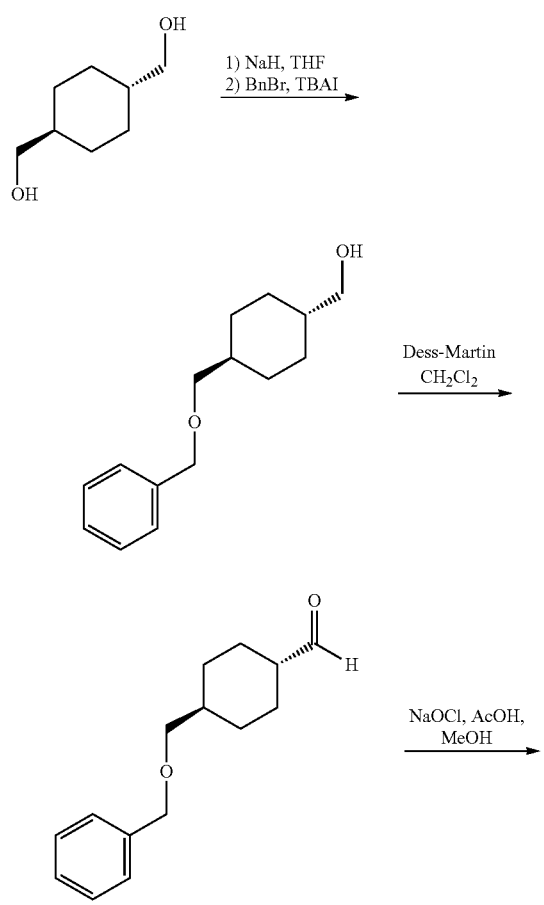

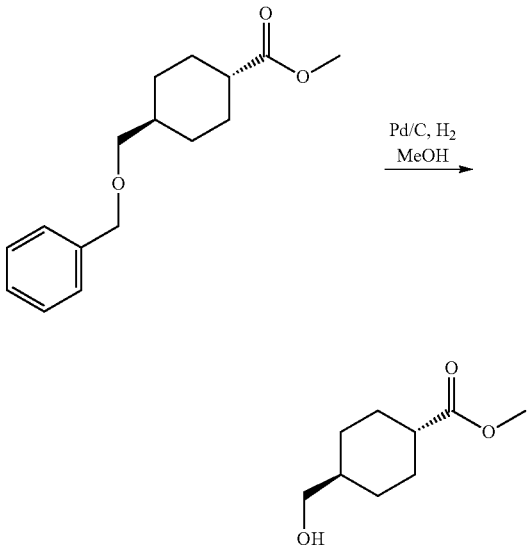

To a slurry of NaH (440 mg, 11 mmol) in THF (22 mL) is added trans-1,4-cyclohexanedimethanol (1.44 g, 10 mmol) at 0° C., and the mixture is stirred for 1 hour while warming to room temperature. Benzyl bromide (1.2 mL, 10 mmol) is added dropwise followed by TBAI (185 mg, 0.5 mmol). The reaction is heated to 60° C. for 15 hours. After cooling to room temperature, H2O is added, and the mixture is extracted with EtOAc. The combined organic layer after dried over MgSO4 is concentrated to obtain (4-benzyloxymethyl-cyclohexyl)-methanol as clear oil (1.40 g, 60%) after purification.

To a mixture of (4-benzyloxymethyl-cyclohexyl)-methanol (1.40 g, 6 mmol) in dichloromethane 28 mL is added Dess-Martin periodinate (2.53 g, 6 mmol) at 0° C., and the mixture is stirred for 0.5 hour while warming to room temperature. After addition of saturated aqueous NaHCO3, the mixture is extracted with EtOAc. The combined organic layer after dried over MgSO4 is concentrated to obtain 4-benzyloxymethyl-cyclohexanecarbaldehyde as clear oil (1.07 g, 79%) after purification.

4-Benzyloxymethyl-cyclohexanecarbaldehyde (1.70 g, 2.0 mmol) is dissolved in acetic acid (0.24 mL) and 2 mL of methanol. The reaction mixture is cooled to 0° C. to 5° C. and stirred while 10% NaOCl solution (2.5 mL, 4 mmol) is added dropwise over 20 minutes. The cooling bath is removed, and the mixture is allowed to come to room temperature. After addition of saturated aqueous NaHCO3, the mixture is extracted with EtOAc. The combined organic layer after dried over MgSO4 is concentrated to obtain 4-benzyloxymethyl-cyclohexanecarboxylic acid methyl ester as clear oil (343 mg, 65%) after purification.

4-Benzyloxymethyl-cyclohexanecarboxylic acid methyl ester (340 mg, 1.30 mmol) is dissolved in MeOH (15 mL). In presence of catalytic amount of 10% Pd/C, the reaction mixture is stirred for 3 hours under hydrogen (10 bar). After removing 10% Pd/C, solvent is evaporated to obtain trans-4-hydroxymethyl-cyclohexanecarboxylic acid methyl ester as colorless oil (160 mg, 72%) after purification. 1H-NMR (400 MHz, CDCl3), δ (ppm): 0.99 (m, 2H), 1.47 (m, 3H), 1.88 (m, 2H), 2.02 (m, 2H), 2.23 (m, 1H), 3.46 (d, 2H), 3.66 (s, 3H).

7) Synthesis of 1-Hydroxymethyl-cyclopentanecarboxylic acid methyl ester

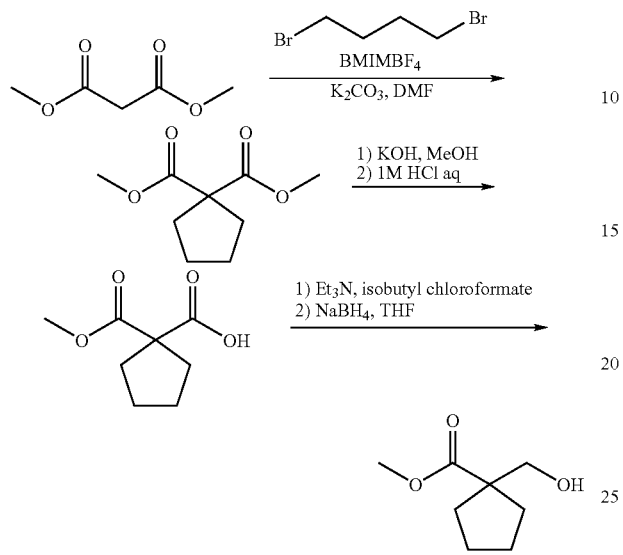

To a solution of malonic acid dimethyl ester (5.28 g, 40 mmol) in DMF (100 ml), 1,4-dibromo-butane (5.26 ml, 44 mmol), K2CO3 (13.8 g, 100 mmol), 1-butyl-3-methylimidazolium tetrafluoroborate (0.904 g, 4.0 mmol) are added at room temperature. The mixture is stirred at room temperature for 15 hours. To the mixture, water is added and the solution is extracted with AcOEt. The organic layer is washed with H2O and brine, dried over MgSO4, and concentrated under reduced pressure. The residue is purified by silica gel column chromatography to give cyclopentane-1,1-dicarboxylic acid dimethyl ester (6.13 g, 82%); TLC (hexane/AcOEt, 5:1) Rf 0.48, $^1$H NMR (400 MHz, chloroform-d) δ ppm 1.67-1.71 (m, 4H), 2.17-2.21 (m, 4H), 3.72 (s, 6H).

To a solution of cyclopentane-1,1-dicarboxylic acid dimethyl ester (4.0 g, 21.5 mmol) in MeOH (25 mL) is added potassium hydroxide (1.32 g, 23.7 mmol). The mixture is stirred at room temperature for 15 hours and concentrated under reduced pressure. To the obtained residue, aqueous 1M HCl (50 mL) is added and the solution is extracted with AcOEt. The organic layer is washed with H2O, dried over Na2SO4, and concentrated under reduced pressure to give cyclopentane-1,1-dicarboxylic acid methyl ester (3.72 g, quant.); TLC (dichloromethane/MeOH, 10:1) Rf 0.25, $^1$H NMR (400 MHz, chloroform-d) δ ppm 1.67-1.74 (m, 4H), 2.17-2.25 (m, 4H), 3.75 (s, 3H).

To a solution of cyclopentane-1,1-dicarboxylic acid methyl ester (1.00 g, 5.81 mmol) and triethylamine (808 uL, 5.81 mmol) in THF (15 mL) is added isobutyl chloroformate (750 uL, 5.81 mmol) at 0° C. The mixture is stirred at 0° C. for 20 minutes. The mixture is filtrated, and the filtrate is added to a suspension of NaBH4 (242 mg) in THF (15 ml) at 0° C. The mixture is stirred at 0° C. for 3 hours and at room temperature for 12 hours. To the mixture, H2O is added and the mixture is extracted with AcOEt. The organic layer is dried over MgSO4, and concentrated under reduced pressure. The obtained residue is purified by silica gel column chromatography to give 1-hydroxymethyl-cyclopentanecarboxylic acid methyl ester (433 mg, 47%); TLC (hexane/AcOEt, 1:1) Rf 0.43, $^1$H NMR (400 MHz, chloroform-d) δ ppm 1.61-1.77 (m, 6H), 1.93-2.00 (m, 2H), 2.53 (m, 1H), 3.57 (d, 2H), 3.72 (s, 3H).

8) Synthesis of trans-(3-hydroxy-cyclobutyl)-acetic acid methyl ester

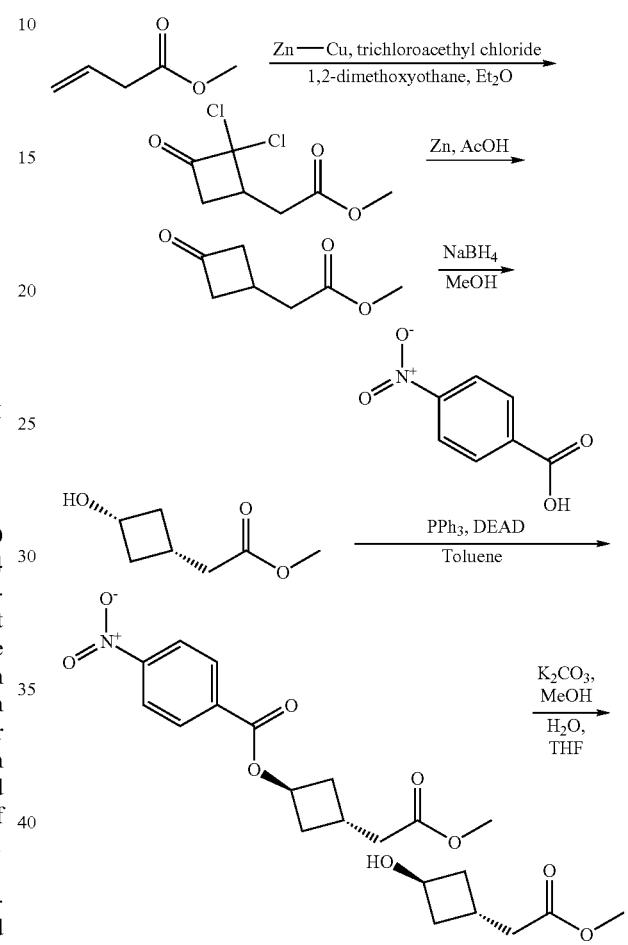

To a mixture of but-3-enoic acid methyl ester (1.00 g, 10 mmol) and zinc-copper couple (1.97 g) in 1,2-dimethoxyethane (4.89 ml) and diethyl ether (37 ml), trichloroacetyl chloride (2.98 ml, 26.7 mmol) is added at room temperature under nitrogen. The mixture is stirred at room temperature for 3 days. The mixture is filtrated and washed with diethyl ether. The filtrate is concentrated under reduced pressure, and the obtained residue is purified by silica gel column chromatography to give (2,2-dichloro-3-oxo-cyclobutyl)-acetic acid methyl ester (2.93 g, quant.); TLC (hexane/AcOEt, 3:1) Rf 0.35, $^1$H NMR (400 MHz, chloroform-d) δ ppm 2.68-2.74 (m, 1H), 2.94-3.00 (m, 1H), 3.06-3.13 (m, 1H), 3.33-3.41 (m, 1H), 3.51-3.57 (m, 1H), 3.75 (s, 3H).

To a solution of (2,2-dichloro-3-oxo-cyclobutyl)-acetic acid methyl ester (2.93 g, 13.8 mmol) in AcOH (100 ml), zinc powder (4.51 g, 69.0 mmol) is added. The mixture is stirred at 100° C. for 15 hours. The mixture is filtrated and washed with AcOH. The filtrate is concentrated under reduced pressure, and the residue is dissolved in AcOEt, and washed with saturated aqueous NaHCO3 and brine. The organic layer is dried over MgSO4, and concentrated under reduced pressure to give (3-oxo-cyclobutyl)-acetic acid methyl ester (710 mg, 36%); 1H NMR (400 MHz, chloroform-d) δ ppm 2.64-2.66 (m, 2H), 2.78-2.86 (m, 3H), 3.22-3.32 (m, 2H), 3.70 (s, 3H).

To a solution of (3-oxo-cyclobutyl)-acetic acid methyl ester (700 mg, 4.92 mmol) in MeOH (20 ml), NaBH4 (205 mg, 5.41 mmol) is added at 0° C. The mixture is stirred at room temperature for 5 hours. To the mixture, H2O is added and a portion of MeOH is removed under reduced pressure. The mixture is extracted with AcOEt and the organic layer is dried over MgSO4, and concentrated under reduced pressure. The obtained residue is purified by silica gel column chromatography to give cis (3-hydroxy-cyclobutyl)-acetic acid methyl ester (578 mg, 80%); TLC (hexane/AcOEt, 1:1) Rf 0.38, 1H NMR (400 MHz, chloroform-d) δ ppm 1.56-1.65 (m, 1H), 1.76 (m, 1H), 2.08-2.16 (m, 2H), 2.44 (d, 2H), 2.51-2.59 (m, 2H), 3.66 (s, 3H), 4.16 (m, 1H).

To a solution of cis-(3-hydroxy-cyclobutyl)-acetic acid methyl ester (570 mg, 3.96 mmol), triphenylphosphine (2.08 g, 7.92 mmol), and 4-nitrobenzoic acid (1.32 g, 7.92 mmol) in dry THF (50 mL), 40% diethyl azodicarboxylate in toluene (1.42 mL, 7.92 mmol) is added at room temperature. The mixture is stirred at room temperature for 15 hours. The solvent is removed under reduced pressure, and the obtained residue is purified by silica gel column chromatography to give trans-4-nitro-benzoic acid 3-methoxycarbonylmethyl-cyclobutyl ester (558 mg, 48%); TLC (hexane/AcOEt, 3:1) Rf 0.31, 1H NMR (400 MHz, chloroform-d) δ ppm 2.28-2.35 (m, 2H), 2.44-2.51 (m, 2H), 2.56 (d, 2H), 2.82-2.87 (m, 1H), 3.69 (s, 3H), 5.33-5.40 (m, 1H). 8.18-8.30 (m, 4H).

To a solution of trans-4-nitro-benzoic acid 3-methoxycarbonylmethyl-cyclobutyl ester (540 mg, 1.84 mmol) in MeOH (20 mL) is added H2O (2.4 mL), THF (10 mL), and K2CO3 (255 mg, 1.84 mmol) at room temperature. The mixture is stirred at room temperature for 45 minutes. The solvent is removed under reduced pressure. Water is added to the obtained residue, and the mixture is extracted with dichloromethane. The organic layer is concentrated under reduced pressure then purified by silica gel column chromatography to give trans-(3-hydroxy-cyclobutyl)-acetic acid methyl ester (230 mg, 87%); TLC (hexane/AcOEt, 1:1) Rf 0.40, 1H NMR (400 MHz, chloroform-d) δ ppm 1.69-1.70 (m, 1H), 2.07-2.19 (m, 4H), 2.44-2.46 (d, 2H), 2.41-2.69 (m, 1H), 3.66 (s, 3H), 4.39-4.47 (m, 1H).

9) Synthesis of trans-2-(3-hydroxy-cyclobutyl)-2-methyl-propionic acid methyl ester

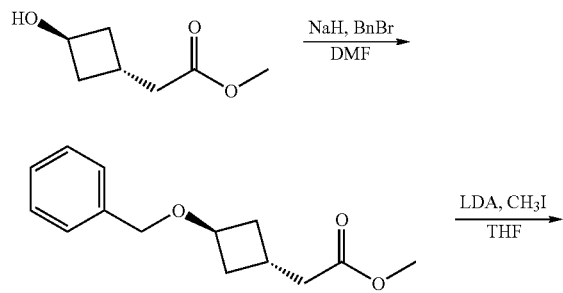

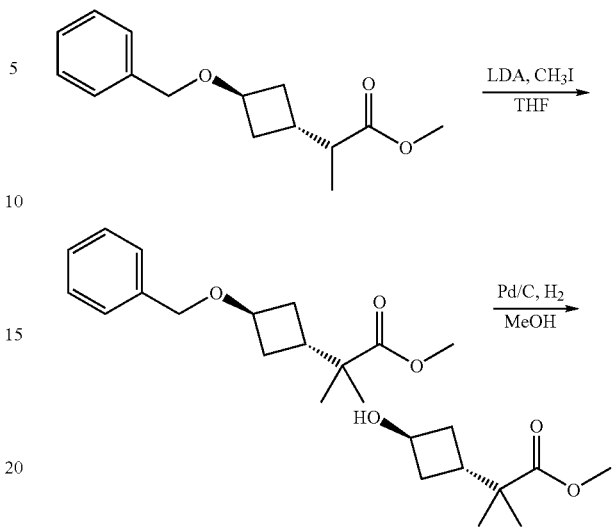

To a solution trans-(3-hydroxy-cyclobutyl)-acetic acid methyl ester (168 mg, 1.17 mmol) in DMF (1.5 mL) is added, NaH (60% in oil, 70 mg, 1.75 mmol) at 0° C. After stirring at 0° C. for 15 minutes, benzyl bromide (167 uL, 1.40 mmol) is added at 0° C. The mixture is stirred at room temperature for 2 hours and quenched with H2O. The mixture is extracted with dichloromethane, and the organic layer is concentrated under reduced pressure. The obtained residue is purified by silica gel column chromatography to give trans-(3-benzyloxy-cyclobutyl)-acetic acid methyl ester (110 mg, 40%); ESI-MS m/z 235 [M+1]+, retention time 1.97 min (condition A).

To a solution of trans-(3-benzyloxy-cyclobutyl)-acetic acid methyl ester (110 mg, 0.47 mmol) in THF (1 mL) is added 1.09M LDA in THF and hexane (1.51 mL, 1.65 mmol) at −78° C. under nitrogen, and stirred at −78° C. for 30 min. To the mixture, iodomethane (232 ul, 3.76 mmol) is added, and the mixture is stirred at −78° C. for 30 min. The temperature is slowly warmed to room temperature for 3 hours. To the mixture, H2O is added and extracted with AcOEt. The organic layer is dried over MgSO4 and concentrated under reduced pressure to give trans-2-(3-benzyloxy-cyclobutyl)-propionic acid methyl ester (94 mg, 80%); ESI-MS m/z 249 [M+1]+, retention time 2.07 min (condition A).

To a solution of trans-2-(3-benzyloxy-cyclobutyl)-propionic acid methyl ester (94 mg, 0.38 mmol) in THF (1 mL) is added 1.09M LDA in THF and hexane (1.51 mL, 1.65 mmol) at −78° C. under nitrogen, and stirred at −78° C. for 30 minutes. To the mixture, iodomethane (232 uL, 3.76 mmol) is added, and stirred at −78° C. for 30 minutes. The temperature is slowly warmed to room temperature for 3 hours. To the mixture, H2O is added and extracted with AcOEt. The organic layer is dried over MgSO4 and concentrated under reduced pressure to give trans-2-(3-benzyloxy-cyclobutyl)-2-methyl-propionic acid methyl ester (70 mg, 70%); ESI-MS m/z 263 [M+1]+, retention time 2.17 min (condition A).

A solution of trans-2-(3-benzyloxy-cyclobutyl)-2-methyl-propionic acid methyl ester (70 mg, 0.26 mmol) as 0.05 M solution in MeOH is pumped through the H-Cube™ flow hydrogenator fitted with 10 mol % Pd/C catalyst cartridge heated to 40° C. at 10 bar. The flow rate is set at 1 mL/min. The solvent is removed under reduced pressure to give trans-2-(3-hydroxy-cyclobutyl)-2-methyl-propionic acid methyl ester (54 mg, quant.); TLC (hexane/AcOEt, 1:1) Rf 0.45, 1H NMR (400 MHz, chloroform-d) δ ppm 1.12 (s, 6H), 1.92-2.03 (m, 2H), 2.18-2.24 (m, 2H), 2.63-2.71 (m, 1H), 3.65 (s, 3H), 4.25-4.31 (m, 1H).

10) Synthesis of 4-Hydroxy-butyric acid methyl ester

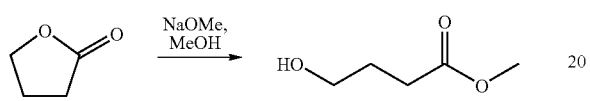

To a solution of sodium methoxide (71.3 mg, 1.32 mmol) in anhydrous MeOH (4 mL) dihydro-furan-2-one (1.14 g, 13.2 mmol) is added dropwise at room temperature under nitrogen. The mixture is stirred at 50° C. for 4 hours and filtered through a silica gel short column (eluent: diethyl ether). The filtrate is concentrated under reduced pressure to give 4-hydroxy-butyric acid methyl ester; $^1$H NMR (400 MHz, chloroform-d). δ ppm 1.85-1.92 (m, 2H), 2.45 (t, 2H), 3.69 (m, 5H).

Example 17

1) Synthesis of cis-4-{[3,5-Bis(trifluoromethyl)benzyl]-[5-(1-methyl-1H-pyrazol-4-yl)-pyrimidin-2-yl]-mino}-2,6-diethyl-piperidine-1-carboxylic acid 1-tert-butoxycarbonyl-azetidin-3-yl ester

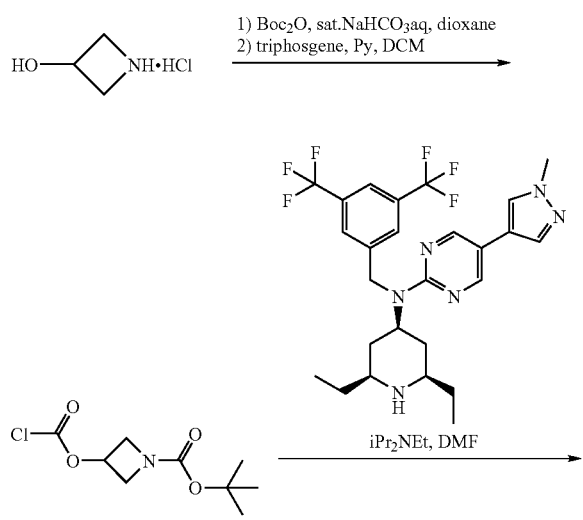

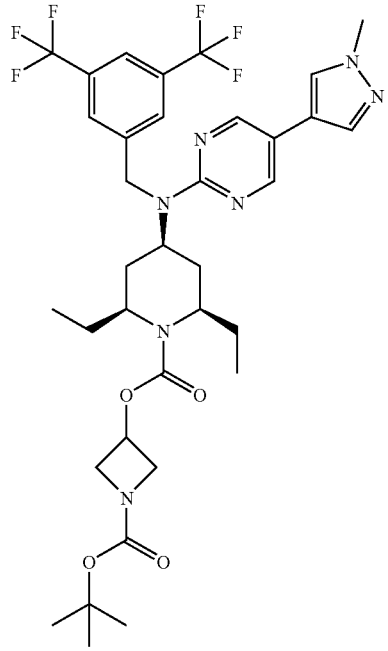

A mixture of 4-hydroxyazetidine hydrochloride (4.66 mmol, 510 mg), Boc2O (5.12 mmol, 1.12 g), saturated aqueous NaHCO3 solution (5 mL) and 1,4-dioxane (5 mL) is stirred at room temperature for 1.5 hours. The mixture is diluted with EtOAc, washed with H2O and brine, dried over Na2SO4 and concentrated. To a solution of the obtained residue in CH2Cl2 (10 mL) is added pyridine (2.35 mmol, 0.19 mL) and triphosgene (1.12 mmol, 332 mg) at 0° C. The mixture is warmed to room temperature and stirred for 1 hour. After cooling to 0° C., the reaction is quenched with saturated aqueous NH4Cl solution. The resulting mixture is extracted with CH2Cl2, washed with brine, dried over Na2SO4 and concentrated. A mixture of the crude material (0.403 mmol, 95 mg), cis-2,6-diethyl-piperidin-4-yl)-[3,5-bis(trifluoromethyl)benzyl]-[5-(1-methyl-1H-pyrazol-4-yl)-pyrimidin-2-yl]-amine (0.202 mmol, 109 mg), i-Pr2NEt (1.61 mmol, 0.28 mL) is dissolved in DMF (0.5 mL). After stirring for 0.5 hours, the additional crude material (0.170 mmol, 40 mg) is added. The reaction mixture is diluted with EtOAc, washed with H2O and brine, dried over Na2SO4 and concentrated. The obtained residue is purified by silica gel column chromatography to give cis-4-{[3,5-bis(trifluoromethyl)benzyl]-[5-(1-methyl-1H-pyrazol-4-yl)-pyrimidin-2-yl]-amino}-2,6-diethyl-piperidine-1-carboxylic acid 1-tert-butoxycarbonyl-azetidin-3-yl ester (94 mg, 63%); 1H-NMR (400 MHz, CDCl3): 0.86 (t, 6H), 1.45 (s, 9H), 1.45-1.62 (m, 4H), 1.76-1.84 (sept, 2H), 2.13-2.21 (m, 2H), 3.90 (dd, 2H), 3.95 (s, 3H), 4.13-4.21 (m, 2H), 4.23-4.28 (m, 2H), 4.76-4.84 (m, 1H), 4.87 (s, 2H), 5.11-5.14 (m, 1H), 7.53 (s, 1H), 7.66 (d, 1H), 7.70 (s, 1H), 7.75 (s, 1H), 8.44 (s, 2H).

2) Synthesis of cis-4-{[3,5-Bis(trifluoromethyl)benzyl]-[5-(1-methyl-1H-pyrazol-4-yl)-pyrimidin-2-yl]-amino}-2,6-diethylpiperidine-1-carboxylic acid 1-methoxycarbonylmethyl-azetidin-3-yl ester

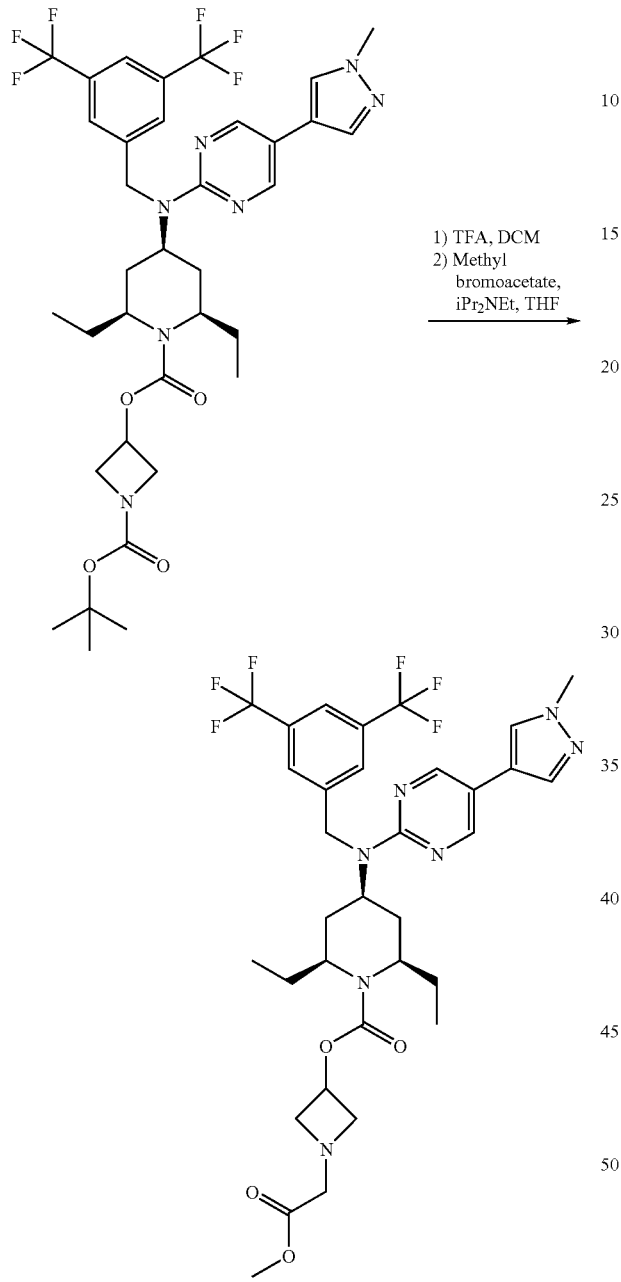

To a solution of cis-4-{[3,5-bis(trifluoromethyl)benzyl]-[5-(1-methyl-1H-pyrazol-4-yl)-pyrimidin-2-yl]-amino}-2,6-diethyl-piperidine-1-carboxylic acid 1-tert-butoxycarbonyl-azetidin-3-yl ester (0.0578 mmol, 37 mg) and i-Pr2NEt (0.116 mmol, 0.020 mL) in THF (1 mL) is added methyl bromoacetate (0.0867 mmol, 0.0082 mL). The reaction mixture is gradually warmed to 60° C. After stirring for 0.5 hours, the reaction mixture is diluted with EtOAc, washed with H2O and brine, dried over Na2SO4, and concentrated. The obtained residue is purified by silica gel column chromatography to give cis-4-{[3,5-bis(trifluoromethyl)benzyl]-[5-(1-methyl-1H-pyrazol-4-yl)-pyrimidin-2-yl]-amino}-2,6-diethylpiperidine-1-carboxylic acid 1-methoxycarbonylmethyl-azetidin-3-yl ester (22 mg, 54%) as colorless oil; ESI-MS m/z: 712 [M+1]+, Retention time 1.95 min. (condition A).

Example 18

Synthesis of (S)-(−)-3-benzoyloxypyrrolidine

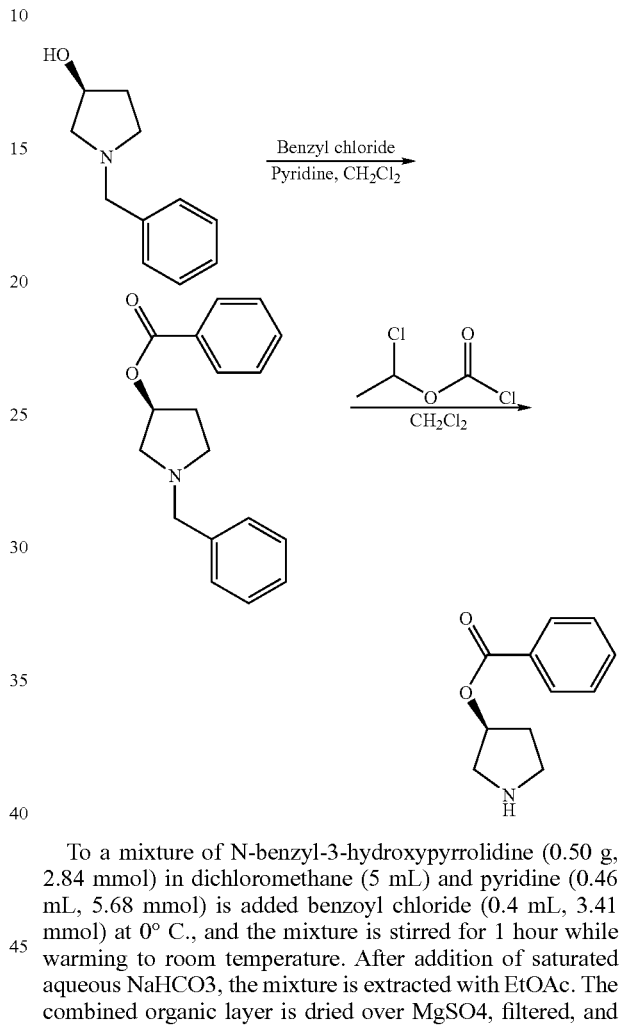

To a mixture of N-benzyl-3-hydroxypyrrolidine (0.50 g, 2.84 mmol) in dichloromethane (5 mL) and pyridine (0.46 mL, 5.68 mmol) is added benzoyl chloride (0.4 mL, 3.41 mmol) at 0° C., and the mixture is stirred for 1 hour while warming to room temperature. After addition of saturated aqueous NaHCO3, the mixture is extracted with EtOAc. The combined organic layer is dried over MgSO4, filtered, and concentrated. The resulting N-benzyl-3-benzoyloxypyrrolidine is used for next step without further purification.

To a crude mixture of N-benzyl-3-benzoyloxypyrrolidine (114 mg, 0.41 mmol) in dichloromethane (1 mL) is added α-chloroethyl chloroformate (57 μL, 0.49 mmol) at 0° C., and the mixture is stirred for 1 hour while warming to room temperature. After removing dichloromethane, resulting mixture is diluted with MeOH. The reaction mixture is heated to 80° C. for 0.5 hour. After cooling to room temperature, solvent is evaporated under reduced pressure to obtain (S)-(−)-3-benzoyloxypyrrolidine which is used for next reaction without further purification.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A compound of formula (I)

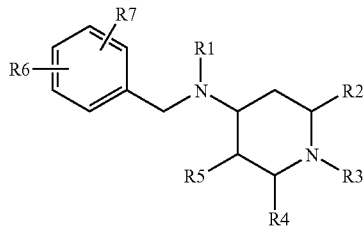

wherein:

R1 is heteroaryl, wherein said heteroaryl is optionally substituted with one to three substituents selected from halogen, dialkylamino, alkoxy, heterocyclyl, wherein said heterocyclyl is further optionally substituted with one to three substituents selected from alkyl, hydroxy or alkanoyl, R2 is alkyl;

R3 is HOC(O)—R9—O—C(O)—;

R4 is alkyl or aryl-alkyl- optionally substituted by one to three alkyl or halogen;

R5 is hydrogen;

R6 and R7 are independently halogen, alkyl or alkoxy, wherein said alkyl is optionally substituted with one to three halogen; and R9 is (C1-C4) alkyl, (C3-C6) cycloalkyl, (C1-C4) alkyl-C3-6cycloalkyl or (C3-C6) cycloalkyl-alkyl; or a pharmaceutically acceptable salt thereof, or an optical isomer thereof; or a mixture of optical isomers thereof.

2. The compound according to claim 1, wherein in formula (I) R1 is 5 or 6-membered heteroaryl, wherein said heteroaryl is optionally substituted with one to three substituents selected from halogen, dialkylamino, (C1-C7) alkoxy, or 5- or 6-membered heterocyclyl, wherein said heterocyclyl is further optionally substituted with one to three substituents selected from (C1-4)alkyl, (C1-C7)alkanoyl or hydroxy;

R2 is (C1-C7) alkyl;

R4 is (C1-C7) alkyl or 6-membered aryl alkyl, wherein aryl is optionally substituted by one to three substituents selected from alkyl or halogen;

R5 is hydrogen;

R6 and R7 are independently halogen, (C1-C7) alkyl or (C1-C7) alkoxy, wherein said alkyl is substituted with one to three halogens; and R9 is

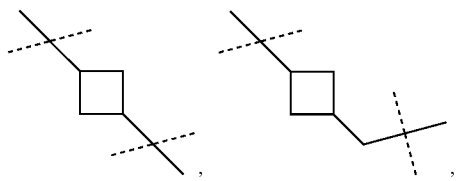

—CH₂C(CH₃)₂CH₂CH₂—,

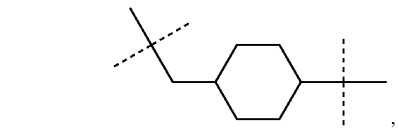

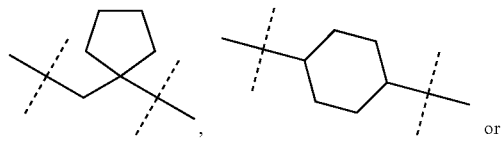 or

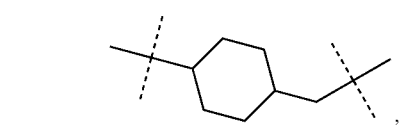

or a pharmaceutically acceptable salt thereof.

3. A pharmaceutical composition, comprising:

a therapeutically effective amount of a compound of formula (I) according to claim 1, or a pharmaceutically acceptable salt thereof, and one or more pharmaceutically acceptable carriers.

4. The pharmaceutical composition according to claim 3, further comprising one or more therapeutically active agents selected from the group consisting of a:

(i) HMG-Co-A reductase inhibitor or a pharmaceutically acceptable salt thereof, (ii) angiotensin II receptor antagonist or a pharmaceutically acceptable salt thereof, (ii) angiotensin converting enzyme (ACE) Inhibitor or a pharmaceutically acceptable salt thereof, (iv) calcium channel blocker or a pharmaceutically acceptable salt thereof, (v) aldosterone synthase inhibitor or a pharmaceutically acceptable salt thereof, (vi) aldosterone antagonist or a pharmaceutically acceptable salt thereof, (vii) dual angiotensin converting enzyme/neutral endopeptidase (ACE/NEP) inhibitor or a pharmaceutically acceptable salt thereof, (viii) endothelin antagonist or a pharmaceutically acceptable salt thereof, (ix) renin inhibitor or a pharmaceutically acceptable salt thereof, (x) diuretic or a pharmaceutically acceptable salt thereof, and (xi) an ApoA-I mimic.

5. A compound according to claim 1 selected from:
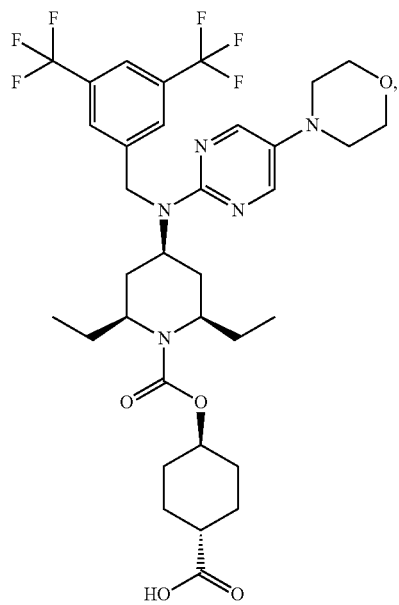
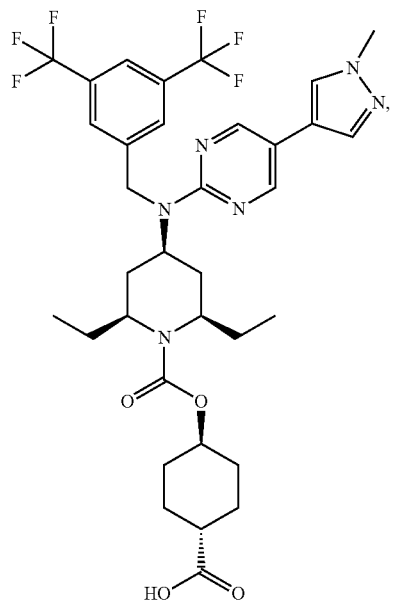
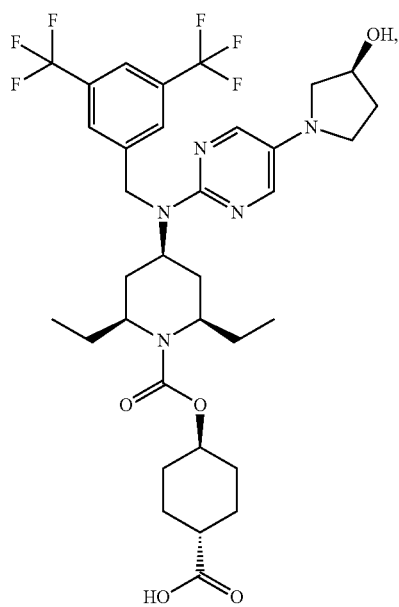
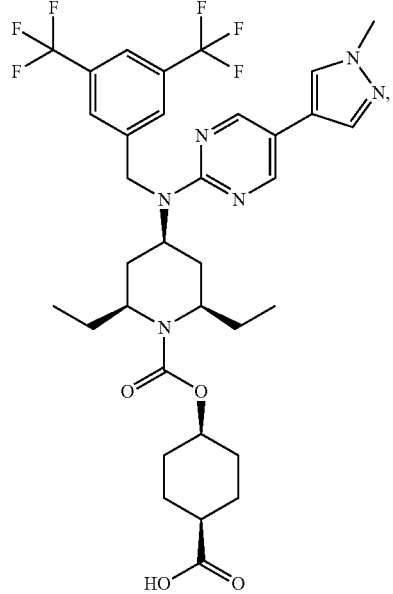

153
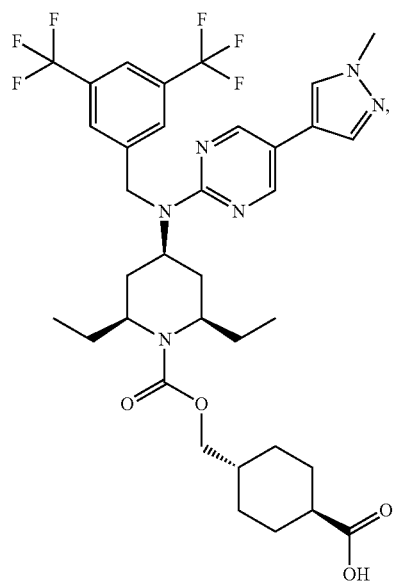
154
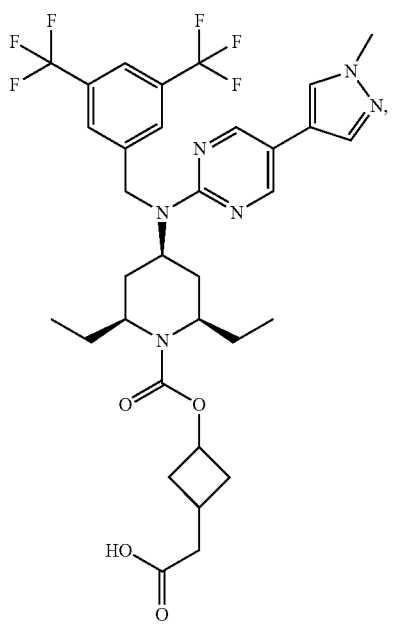
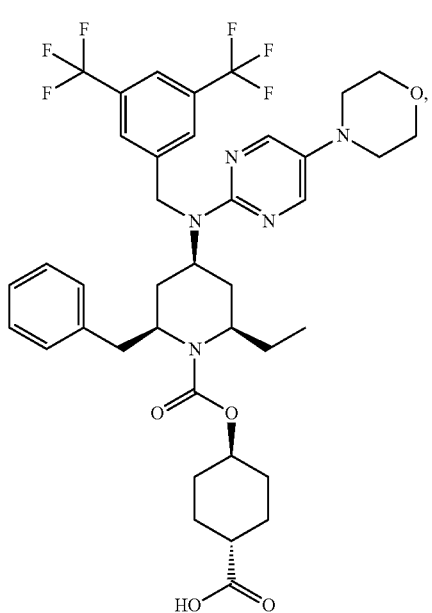
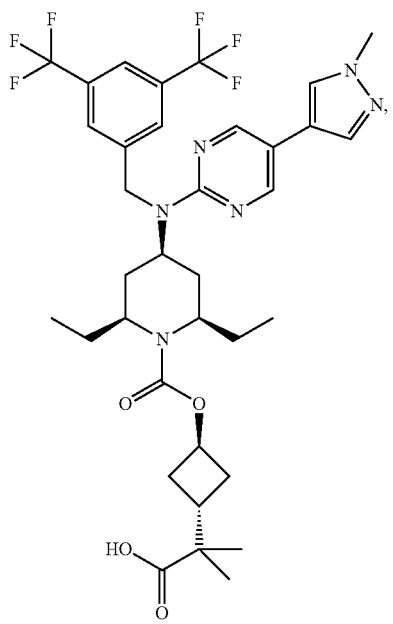

155
-continued
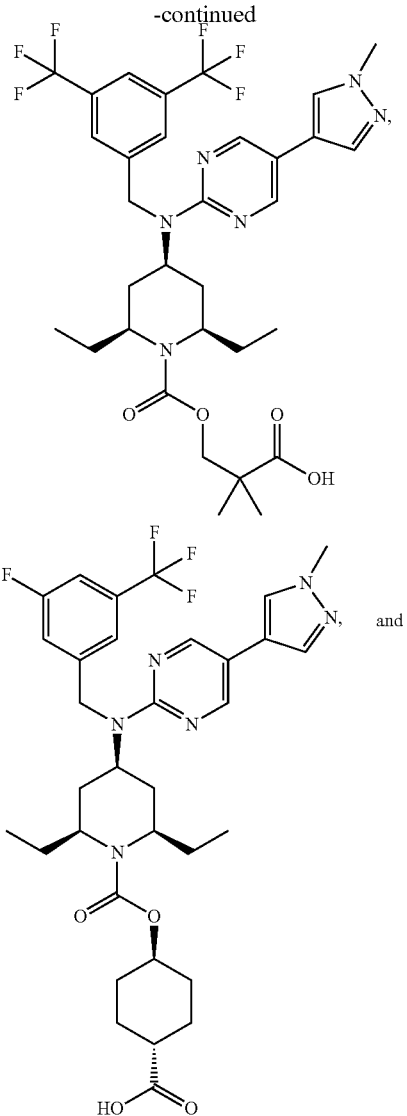
and
156
-continued
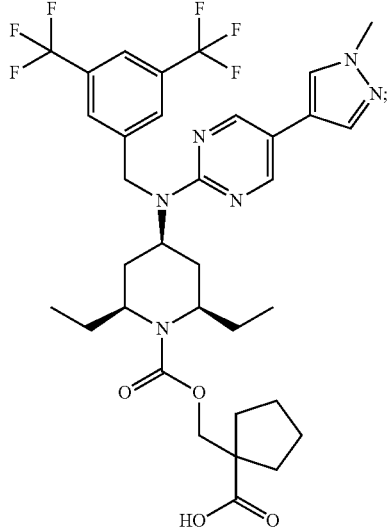
or a pharmaceutically acceptable salt thereof.
6. A pharmaceutical composition, comprising:
a therapeutically effective amount of a compound of formula (I) according to claim 5, or a pharmaceutically acceptable salt thereof, and one or more pharmaceutically acceptable carriers.
* * * * *

UNITED STATES PATENT AND TRADEMARK OFFICE
CERTIFICATE OF CORRECTION

| | | |
|---|---|---|
| PATENT NO. | : 8,193,349 B2 | Page 1 of 1 |
| APPLICATION NO. | : 12/265369 | |
| DATED | : June 5, 2012 | |
| INVENTOR(S) | : Mogi et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 658 days.

Signed and Sealed this
Twenty-eighth Day of August, 2012

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 8,193,349 B2 |
| APPLICATION NO. | : 12/265369 |
| DATED | : June 5, 2012 |
| INVENTOR(S) | : Mogi et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 671 days.

Signed and Sealed this
Twelfth Day of August, 2014

Michelle K. Lee
*Deputy Director of the United States Patent and Trademark Office*